United States Patent
Dai

(10) Patent No.: US 10,783,999 B2
(45) Date of Patent: Sep. 22, 2020

(54) BASIS DATA EVALUATION SYSTEMS AND METHODS

(71) Applicant: AMO Development, LLC, Santa Ana, CA (US)

(72) Inventor: Guang-ming Dai, Fremont, CA (US)

(73) Assignee: AMO Development, LLC, Santa Ana, CA (US)

( * ) Notice: Subject to any disclaimer, the term of this patent is extended or adjusted under 35 U.S.C. 154(b) by 204 days.

(21) Appl. No.: 14/728,638

(22) Filed: Jun. 2, 2015

(65) Prior Publication Data

US 2015/0359602 A1 Dec. 17, 2015

Related U.S. Application Data

(60) Provisional application No. 62/010,925, filed on Jun. 11, 2014.

(51) Int. Cl.
| | |
|---|---|
| *G16H 50/50* | (2018.01) |
| *A61F 9/008* | (2006.01) |
| *A61B 34/10* | (2016.01) |
| *G06F 19/00* | (2018.01) |

(52) U.S. Cl.
CPC ......... *G16H 50/50* (2018.01); *A61F 9/00802* (2013.01); *G06F 19/00* (2013.01); *A61B 2034/105* (2016.02); *A61F 2009/0088* (2013.01); *A61F 2009/00848* (2013.01); *A61F 2009/00851* (2013.01); *A61F 2009/00882* (2013.01)

(58) Field of Classification Search
CPC ... A61B 19/50; A61B 34/10; A61B 2034/101; A61F 9/00802; A61F 2009/00848; A61F 2009/00851; A61F 2009/0088; A61F 2009/00882; G06F 19/3437
USPC ........... 606/4; 703/11, 6; 600/427, 416, 411; 434/262; 705/3
See application file for complete search history.

(56) References Cited

U.S. PATENT DOCUMENTS 7,926,490 B2 * 4/2011 Dai ..................... A61F 9/008
  128/898
8,585,687 B2  11/2013 Campbell
(Continued)

FOREIGN PATENT DOCUMENTS

WO  2015/191386  12/2015

OTHER PUBLICATIONS

Huang et al., Mathematical Model of Corneal Surface Smoothing After Laser Refractive Surgery, Mar. 2003, American Journal of Ophthalmology, vol. 135, No. 3, pp. 267-278 (Year: 2003).*

(Continued)

*Primary Examiner* — Michael W Kahelin
*Assistant Examiner* — Vynn V Huh
(74) *Attorney, Agent, or Firm* — Johnson & Johnson Surgical Vision, Inc.

(57) ABSTRACT

Systems, methods, and computer program products are provided for the administration of ablation profiles during refractive surgery treatments. Basis data framework techniques enable the implementation of ablation profiles having various shapes, resulting in increased ablation accuracy when treating certain vision conditions. Exemplary basis data architecture approaches are configured to efficiently operate with annular, elliptical, and slit laser beam shapes.

5 Claims, 36 Drawing Sheets

(56) References Cited

U.S. PATENT DOCUMENTS

| | | | |
|---|---|---|---|
| 2002/0035359 A1* | 3/2002 | Yee | A61F 9/008 606/9 |
| 2006/0015090 A1* | 1/2006 | Roberts | A61F 9/008 606/5 |
| 2008/0287929 A1 | 11/2008 | Holliday et al. | |
| 2012/0083776 A1 | 4/2012 | Dai et al. | |
| 2012/0172854 A1* | 7/2012 | Raymond | A61F 9/008 606/5 |
| 2012/0173468 A1* | 7/2012 | Gillam | G06F 19/345 706/13 |
| 2013/0190736 A1 | 7/2013 | Fabrikant et al. | |
| 2014/0095137 A1 | 4/2014 | Dai et al. | |
| 2014/0135748 A1 | 5/2014 | Dai et al. | |
| 2014/0163535 A1 | 6/2014 | Dai et al. | |

OTHER PUBLICATIONS

Munnerlyn, C.R., et al., "Theory concerning the ablation of corneal tissue with large-area, 193-nm excimer laser beams." *Journal of Biomedical Optics*, vol. 11, (Nov./Dec. 2006): pp. 1-8.

Munnerlyn, C.R., et al., "Photorefractive keratectomy: A technique for laser refractive surgery." *Journal of Cataract Refractive Surgery*, vol. 14, (Jan. 1988): pp. 46-51.

Zadnik, K., et al., "The Repeatability of Measurement of the Ocular Components." *Investigative Ophthalmology & Visual Science*, vol. 33, No. 7 (Jun. 1992): pp. 2325-2333.

Huang, D., et al., "Mathematical model of corneal surface smoothing after laser refractive surgery." *American Journal of Ophthalmology*, vol. 135, No. 3 (Mar. 1, 2003): pp. 274-277.

International Search Report and Written Opinion dated Aug. 28, 2015 for International Patent Application No. PCT/US2015/034421 filed Jun. 5, 2015, 12 pages.

* cited by examiner

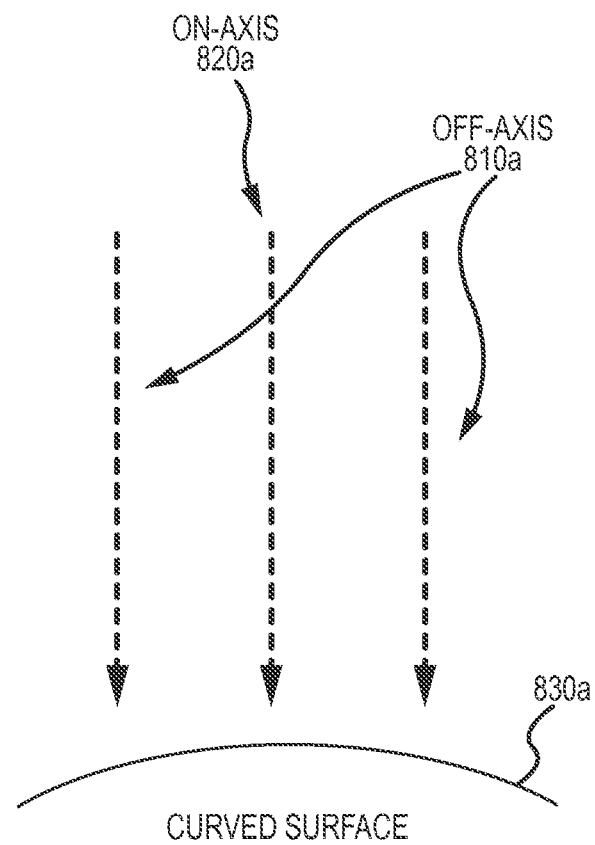
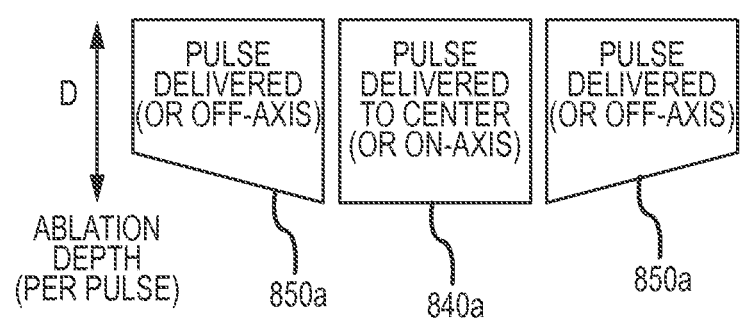
FIG. 8A

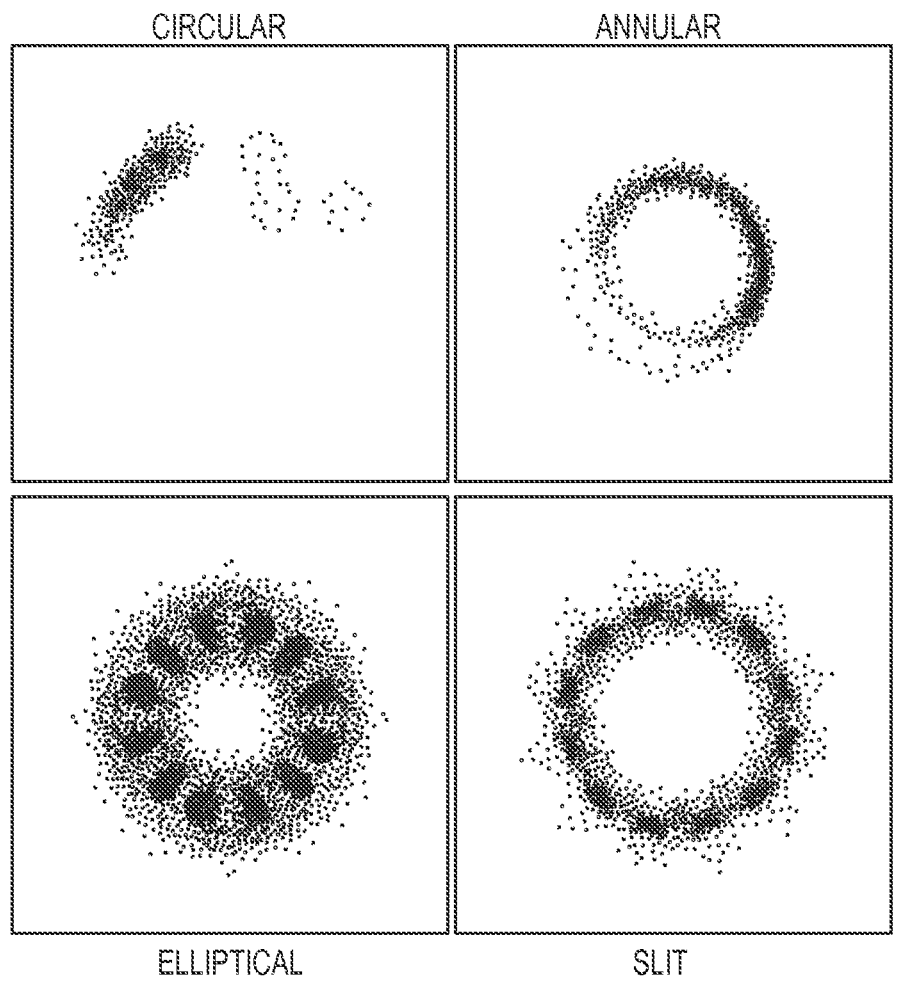
FIG.13A
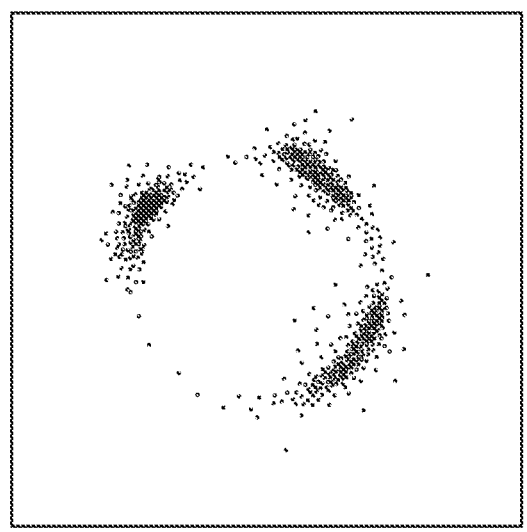
COMBINATION OF VARIOUS SHAPES    FIG.13B

FITTING QUALITY - #PULSES, RMS AND PV

| SHAPES | # PULSES | RMS (um) | PV (um) |
|---|---|---|---|
| CIRCULAR* | 752 | 0.166 | 1.097 |
| ANNULAR | 520 | 1.163 | 5.952 |
| ELLIPTICAL | 376 | 1.067 | 4.217 |
| SLIT | 470 | 1.152 | 4.816 |

*OPTIMIZED USING SIMULATED ANNEALING ALGORITHM

FIG.13E

CORNEAL ABLATION DATA

BASIS DATA EVALUATION SYSTEMS AND METHODS

CROSS-REFERENCES TO RELATED APPLICATIONS

This application is a non-provisional of and claims the benefit of priority to U.S. Provisional Patent Application No. 62/010,925, filed Jun. 11, 2014. This application is related to U.S. Provisional Patent Application No. 61/708,815, filed Oct. 2, 2012, U.S. Provisional Patent Application No. 61/724,111, filed Nov. 8, 2012, U.S. Provisional Patent Application No. 61/734,030, filed Dec. 6, 2012, and U.S. Provisional Patent Application No. 61/765,567, filed Feb. 15, 2013. Further, this application is related to U.S. patent application Ser. No. 14/044,650 filed Oct. 2, 2013, U.S. patent application Ser. No. 14/073,583 filed Nov. 6, 2013, and U.S. patent application Ser. No. 14/097,841 filed Dec. 5, 2013. This application is also related to U.S. patent application Ser. Nos. 12/897,946 and 13/554,276 filed Oct. 5, 2010 and Jul. 20, 2012, respectively, and to U.S. Pat. No. 7,926,490. The content of each of the above patent filings is incorporated herein by reference.

BACKGROUND OF THE INVENTION

Embodiments of the present invention relate to vision treatment systems and methods, and in particular to basis data techniques for use with ophthalmolgical laser ablation systems and methods.

Many current laser correction techniques use small spot scanning systems or broad beam lasers for treating a wide variety of vision conditions, such as myopia and hyperopia. Although these and other proposed treatment devices and methods may provide real benefits to patients in need thereof, still further advances would be desirable. For example, there continues to be a need for improved treatment systems and methods that provide enhanced accuracy of treatment. Embodiments of the present invention provide solutions that address certain inefficiencies or shortcomings which may be associated with known techniques, and hence provide answers to at least some of these outstanding needs.

BRIEF SUMMARY OF THE INVENTION

Embodiments of the present invention encompass systems and methods for developing basis data refinements and improvements for refractive surgical laser procedures. Basis data approaches currently used in excimer laser applications are observed to deliver excellent results, for example in myopia treatments and the like. In some instances, however, presently known basis data techniques may result in the inducement of high order aberrations. Relatedly, in some instances results observed in hyperopic clinical outcomes may be less than optimal. Embodiments of the present invention provide improved basis data techniques which may not require the re-measurement and/or re-determination of basis data.

The use of a basis data framework allows the implementation of various ablation profile shapes when treating certain vision conditions. Often, the basis data can provide a representation or description of the ablation profile created by a single pulse. Basis data can vary according to certain operational parameters. For example, basis data may vary based on the diameter of an iris of a laser ablation system. Embodiments of the present invention provide techniques for using laser basis data during refractive surgery treatment procedures. These techniques can be implemented in a variety of laser devices, including without limitation the WaveScan® System and the STAR S4® Excimer Laser System both by Abbott Medical Optics Inc., the WaveLight® Allegretto Wave® Eye-Q laser, the Schwind Amaris™ lasers, the 217P excimer workstation by Technolas PerfectVision GmbH, the Mel 80™ laser by Carl Zeiss Meditec, Inc., and the like.

In one aspect, embodiments of the present invention encompass methods for determining a treatment basis data for use in a laser ablation vision procedure for a patient. Exemplary methods can include inputting an initial basis data, where the initial basis data includes a set of pulse profiles. Methods can further include inputting a first treatment target for a first individual, where the first treatment target is based on measurement information for the individual and the initial basis data. The measurement information for the individual can include a wavefront measurement, a topography measurement, or both. Methods can also include generating a predicted surgery outcome for the first individual, where the predicted surgery outcome is based on the first treatment target and a healing kernel. Methods can also include comparing the predicted surgery outcome with an actual surgery outcome for the first individual. Methods can also include determining, via a processing module having a tangible medium embodying machine-readable code, the treatment basis data for use in the laser ablation vision procedure, where the treatment basis data is based on the initial basis data and the comparison between the predicted surgery outcome and the actual surgery outcome for the first individual, and where the treatment basis data includes a set of pulse profiles that differs from the set of pulse profiles of the initial basis data. In some cases, methods can include determining a patient treatment target for the patient, where the patient treatment target is based on the treatment basis data and a wavefront measurement for the patient. In some cases, methods can include delivering the patient treatment target to the patient. In some cases, the step of comparing the predicted surgery outcome with the actual surgery outcome for the first individual is based on a least mean squares comparison. In some cases, methods can include inputting a second treatment target for a second individual, where the second treatment target is based on a wavefront measurement for the second individual and the initial basis data, generating a predicted surgery outcome for the second individual, where the predicted surgery outcome is based on the second treatment target and the healing kernel, comparing the predicted surgery outcome with an actual surgery outcome for the second individual, and determining, via the processing module having the tangible medium embodying machine-readable code, the treatment basis data for use in the laser ablation vision procedure, where the treatment basis data is based on the initial basis data and the comparison between the predicted surgery outcome and the actual surgery outcome for the second individual.

In another aspect, embodiments of the present invention encompass systems for determining a treatment basis data for use in a laser ablation vision procedure for a patient. Exemplary systems include a processor, and a storage medium having a computer application that, when executed by the processor, is configured to cause the system to access an initial basis data, where the initial basis data has a set of pulse profiles, to access a first treatment target for a first individual, where the first treatment target is based on a wavefront measurement, a topography measurement, or both for the first individual and the initial basis data, to generate a predicted surgery outcome for the first individual, where the predicted surgery outcome is based on the first treatment target and a healing kernel, to compare the predicted surgery outcome with an actual surgery outcome for the first individual, and to determine the treatment basis data for use in the laser ablation vision procedure, where the treatment basis data is based on the initial basis data and the comparison between the predicted surgery outcome and the actual surgery outcome for the first individual, and where the treatment basis data comprises a set of pulse profiles that differs from the set of pulse profiles of the initial basis data. In some cases, the processor is configured to receive the initial basis data as input. In some cases, the computer application, when executed by the processor, is configured to cause the system to determine a patient treatment target for the patient, where the patient treatment target is based on the treatment basis data and a wavefront measurement for the patient. In some cases, systems include a laser ablation delivery module configured to deliver the patient treatment target to the patient. In some cases, the computer application, when executed on the processor, is configured to cause the system to compare the predicted surgery outcome with the actual surgery outcome for the first individual based on a least mean squares comparison. In some cases, the computer application, when executed on the processor, is configured to cause the system to access a second treatment target for a second individual, where the second treatment target is based on a wavefront measurement for the second individual and the initial basis data, to generate a predicted surgery outcome for the second individual, where the predicted surgery outcome is based on the second treatment target and the healing kernel, to compare the predicted surgery outcome with an actual surgery outcome for the second individual, and to determine, via the processing module having the tangible medium embodying machine-readable code, the treatment basis data for use in the laser ablation vision procedure, where the treatment basis data is based on the initial basis data and the comparison between the predicted surgery outcome and the actual surgery outcome for the second individual.

In still another aspect, embodiments of the present invention encompass methods for determining a treatment basis data for use in a laser ablation vision procedure for a patient. Exemplary methods can include inputting an initial basis data, where the initial basis data includes a set of pulse profiles, inputting a first treatment target for a first individual, where the first treatment target is based on a wavefront measurement, a topography measurement, or both for the first individual and the initial basis data, generating a predicted surgery outcome for the first individual, where the predicted surgery outcome is based on the first treatment target, comparing the predicted surgery outcome with an actual surgery outcome for the first individual, where the actual surgery outcome is based on an optical coherence tomography analysis of an eye of the first individual treated with the first treatment target, and determining, via a processing module having a tangible medium embodying machine-readable code, the treatment basis data for use in the laser ablation vision procedure, where the treatment basis data is based on the initial basis data and the comparison between the predicted surgery outcome and the actual surgery outcome for the first individual, and where the treatment basis data includes a set of pulse profiles that differs from the set of pulse profiles of the initial basis data. In some cases, methods can include determining a patient treatment target for the patient, where the patient treatment target is based on the treatment basis data and a wavefront measurement for the patient. In some cases, methods can include delivering the patient treatment target to the patient. In some cases, the step of comparing the predicted surgery outcome with the actual surgery outcome for the first individual is based on a least mean squares comparison. In some cases, methods can include inputting a second treatment target for a second individual, where the second treatment target is based on a wavefront measurement, a topography measurement, or both for the second individual and the initial basis data, generating a predicted surgery outcome for the second individual, where the predicted surgery outcome is based on the second treatment target, comparing the predicted surgery outcome with an actual surgery outcome for the second individual, where the actual surgery outcome is based on an optical coherence tomography analysis of an eye of the second individual treated with the second treatment target, and determining, via the processing module having the tangible medium embodying machine-readable code, the treatment basis data for use in the laser ablation vision procedure, where the treatment basis data is based on the initial basis data and the comparison between the predicted surgery outcome and the actual surgery outcome for the second individual.

In yet another aspect, embodiments of the present invention encompass systems for determining a treatment basis data for use in a laser ablation vision procedure for a patient. Exemplary systems can include a processor, and a storage medium having a computer application that, when executed by the processor, is configured to cause the system to access an initial basis data, where the initial basis data includes a set of pulse profiles, to access a first treatment target for a first individual, where the first treatment target is based on a wavefront measurement, a topography measurement, or both for the first individual and the initial basis data, to generate a predicted surgery outcome for the first individual, where the predicted surgery outcome is based on the first treatment target, to compare the predicted surgery outcome with an actual surgery outcome for the first individual, where the actual surgery outcome is based on an optical coherence tomography analysis of an eye of the first individual treated with the first treatment target, and to determine the treatment basis data for use in the laser ablation vision procedure, where the treatment basis data is based on the initial basis data and the comparison between the predicted surgery outcome and the actual surgery outcome for the first individual, and where the treatment basis data comprises a set of pulse profiles that differs from the set of pulse profiles of the initial basis data. In some cases, the processor is configured to receive the initial basis data as input. In some cases, the computer application, when executed by the processor, is configured to cause the system to determine a patient treatment target for the patient, where the patient treatment target is based on the treatment basis data and a wavefront measurement for the patient. In some cases, systems can include a laser ablation delivery module configured to deliver the patient treatment target to the patient. In some cases, the computer application, when executed on the processor, is configured to cause the system to compare the predicted surgery outcome with the actual surgery outcome for the first individual based on a least mean squares comparison. In some cases, the computer application, when executed on the processor, is configured to cause the system to access a second treatment target for a second individual, where the second treatment target is based on a wavefront measurement, a topography measurement, or both for the second individual and the initial basis data, to generate a predicted surgery outcome for the second individual, where the predicted surgery outcome is based on the second treatment target, to compare the predicted surgery outcome with an actual surgery outcome for the second individual, where the actual surgery outcome is based on an optical coherence tomography analysis of an eye of the second individual treated with the second treatment target, and to determine, via the processing module having the tangible medium embodying machine-readable code, the treatment basis data for use in the laser ablation vision procedure, where the treatment basis data is based on the initial basis data and the comparison between the predicted surgery outcome and the actual surgery outcome for the second individual.

In another aspect, embodiments of the present invention encompass methods for determining an adjusted basis data for use in a laser ablation vision procedure for a patient. Exemplary methods can include inputting an initial basis data, where the initial basis data includes a set of pulse profiles, inputting a treatment target for the patient, where the treatment target is based on a wavefront measurement, a topography measurement, or both for the patient and the initial basis data, generating a predicted surgery outcome for the patient, where the predicted surgery outcome is based on the treatment target, comparing the predicted surgery outcome with an actual surgery outcome for the patient, where the actual surgery outcome is based on an optical coherence tomography analysis of an eye of the patient treated with the treatment target as part of a laser ablation vision procedure, and determining, via a processing module having a tangible medium embodying machine-readable code, an adjusted basis data, where the adjusted basis data is based on the initial basis data and the comparison between the predicted surgery outcome and the actual surgery outcome for the patient, and where the adjusted basis data comprises a set of pulse profiles that differs from the set of pulse profiles of the initial basis data. In some cases, methods include determining an adjusted patient treatment target for the patient, where the adjusted patient treatment target is based on the adjusted basis data and the wavefront measurement for the patient. In some cases, methods can include delivering the adjusted patient treatment target to the patient. In some cases, the step of comparing the predicted surgery outcome with the actual surgery outcome for the patient is based on a least mean squares comparison.

In still yet another aspect, embodiments of the present invention encompass systems for determining an adjusted basis data for use in a laser ablation vision procedure for a patient. Exemplary systems can include a processor, and a storage medium having a computer application that, when executed by the processor, is configured to cause the system to access an initial basis data, where the initial basis data includes a set of pulse profiles, to generate a treatment target for the patient, where the treatment target is based on a wavefront measurement, a topography measurement, or both for the patient and the initial basis data, to generate a predicted surgery outcome for the patient, where the predicted surgery outcome is based on the treatment target, to compare the predicted surgery outcome with an actual surgery outcome for the patient, where the actual surgery outcome is based on an optical coherence tomography analysis of an eye of the patient treated with the treatment target, and to determine the adjusted basis data for use in the laser ablation vision procedure, where the adjusted basis data is based on the initial basis data and the comparison between the predicted surgery outcome and the actual surgery outcome for the patient, and where the adjusted basis data includes a set of pulse profiles that differs from the set of pulse profiles of the initial basis data. In some cases, the processor is configured to receive the initial basis data as input. In some cases, systems can include a laser ablation delivery module configured to deliver the treatment target and the adjusted treatment target to the patient. In some cases, the computer application, when executed on the processor, is configured to cause the system to compare the predicted surgery outcome with the actual surgery outcome for the patient based on a least mean squares comparison.

For a fuller understanding of the nature and advantages of the present invention, reference should be had to the ensuing detailed description taken in conjunction with the accompanying drawings.

BRIEF DESCRIPTION OF THE DRAWINGS

FIGS. 8A and 8B depict aspects of a treatment patterns or protocols having ablation pulses, according to embodiments of the present invention.

FIGS. 13A, 13B, 13C, 13D, 13E, 13F, and 13G depict representations of basis data and related treatment table features, according to embodiments of the present invention.

DETAILED DESCRIPTION OF THE INVENTION

Figure 1:
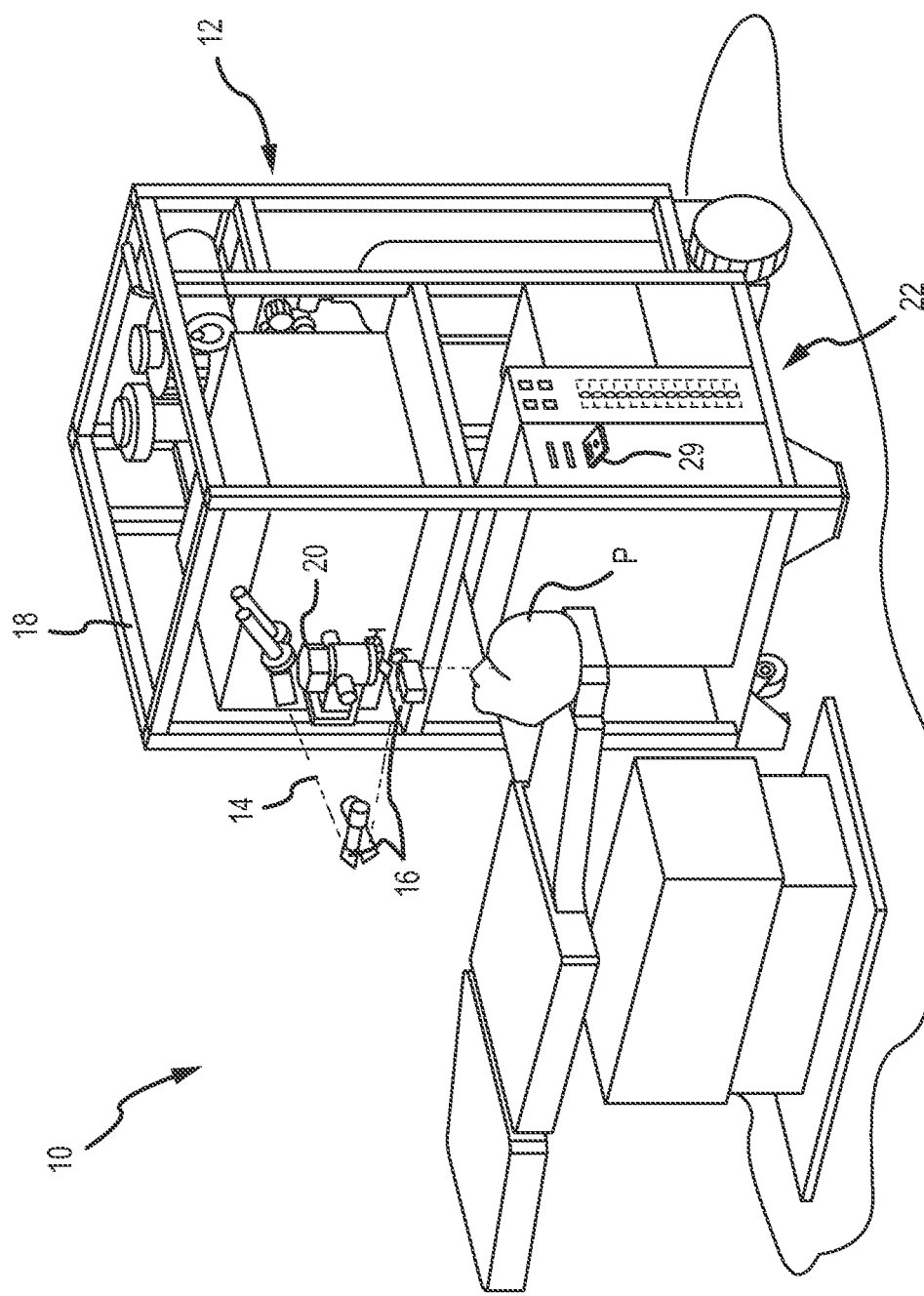
FIG. 1 illustrates a laser ablation system according to embodiments of the present invention.

Although the methods, devices, and systems of the present invention are described primarily in the context of a laser eye surgery system, it should be understood that the techniques of the present invention may be adapted for use in other eye treatment procedures and systems such as contact lenses, intra-ocular lenses, radial keratotomy, collagenous corneal tissue thermal remodeling, removable corneal lens structures, glass spectacles, corneal ring implants, and the like.

Exemplary systems and methods disclosed herein can be implemented via a variety of ophthalmic devices or solutions. For example, treatment techniques may be used for any of a variety of surgery modalities, including excimer laser surgery, femtosecond surgery, and the like. A variety of forms of lasers and laser energy can be used to effect a correction or treatment, including infrared lasers, ultraviolet lasers, femtosecond lasers, wavelength multiplied solid-state lasers, and the like. By way of non-limiting example, ophthalmic corrections can involve a cornea or lens reshaping procedure, such as, for example using a picosecond or femtosecond laser. Laser ablation procedures can remove a targeted amount stroma of a cornea to change a cornea's contour and adjust for aberrations. In some cases, a treatment protocol can involve the delivery of a series of discrete pulses of laser light energy, with a total shape and amount of tissue removed being determined by a shape, size, location, and/or number of laser energy pulses impinging on or focused within a cornea. In some cases, a surgical laser, such as a non-ultraviolet, ultra-short pulsed laser that emits radiation with pulse durations as short as nanoseconds and femtoseconds (e.g., a femtosecond laser, or a picosecond laser) can be used to treat the eye of a patient. Other pulse widths may be suitable as well. The laser systems can be configured to deliver near infrared light. Other wavelengths may be used as well. The laser systems can be configured to deliver laser light focused at a focus depth (e.g. within corneal or other ophthalmologic tissue) which may be controlled by the system. Laser surgery with ultra-short pulse lasers such as femtosecond lasers can be used to treat the eye. These pulsed lasers can make very accurate incisions of the eye and can be used in many ways to treat the eye. Additional types of incisions that can be performed with the short pulse lasers include incisions for paracentesis, limbal relaxing incisions, and refractive incisions to shape the cornea, for example.

In some cases, vision treatments can include focusing femtosecond laser energy within the stroma so as to ablate a volume of intrastromal tissue. By scanning the focal spot within an appropriate volume of the stromal tissue, it is possible to vaporize the volume so as to achieve a desired refractive alteration. Hence, embodiments of the present invention encompass laser surgical techniques that involve femtosecond laser photodisruption or photoalteration treatments. In some cases, a femtosecond laser can be used to perform the photodisruption, thus providing an easy, precise, and effective approach to refractive surgery According to some embodiments, a femtosecond laser (or other laser) of the optical system can be used to incise the cornea or to cut a flap. A femtosecond laser may be used to make arcuate or other incisions in the cornea, which incisions may be customized, intrastromal, stable, predictable, and the like. Likewise, corneal entry incisions may be made, which are custom, multi-plane, and self-sealing.

Pulsed laser beams include bursts or pulses of light. Pulsed lasers, such as non-ultraviolet, ultra-short pulsed lasers with pulse durations measured in the nanoseconds to femtoseconds range, can be used in ophthalmic surgical procedures as disclosed herein. For example, a pulsed laser beam can be focused onto a desired area of ophthalmologic material or tissue, such as the cornea, the capsular bag, or the lens of the eye, to photoalter the material in this area and, in some instances, the associated peripheral area. Examples of photoalteration of the material include, but are not necessarily limited to, chemical and physical alterations, chemical and physical breakdown, disintegration, ablation, photodisruption, vaporization, a the like. Exemplary treatment systems can include a focusing mechanism (e.g. lens) and/or a scanning mechanism so as to guide or direct a focus of femtosecond energy along a path within the patient's eye (e.g. at one or more corneal subsurface locations).

According to some embodiments, the vergence weighting systems and methods disclosed herein can be implemented in connection with software residing in a diagnostic device such as WaveScan® and iDesign™ devices.

The broad beam top hat laser profile of ablation systems such as the STAR S4® Excimer Laser System by Abbott Medical Optics Inc. is highly effective in ablating myopic shapes, due to the high efficiency of material removal in unit time. Similar efficiencies can be achieved for the ablation of hyperopic shapes. For example reducing the maximum spot size from 6.5 mm to about 4 mm, can effectively reducing the maximum efficiency to $4^2/6.5^2=38\%$. Furthermore, the solution accuracy tolerance, which may be defined as the root mean squares (RMS) error between a target shape and an ablated shape, can involve the use of more small pulses, bringing such an efficiency reduction in practice to the level of nearly 15% for hyperopia. For example, a typical −4 D treatment may involve an ablation of 20 seconds, and a typical +4 treatment may involve an ablation of 120 seconds to ablation, with a 20 Hz laser. The use of other ablation shapes optionally combined with basis data adjustment techniques can improve the treatment time for hyperopia and other vision conditions.

Embodiments of the present invention can be readily adapted for use with existing laser systems and other optical treatment devices. Although system, software, and method embodiments of the present invention are described primarily in the context of a laser eye surgery system, it should be understood that embodiments of the present invention may be adapted for use in alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom intraocular lenses, custom contact lenses, custom corneal implants, and the like, which can be configured to treat or ameliorate any of a variety of vision conditions in a particular patient based on their unique ocular characteristics or anatomy. Additionally, the ablation target or target shape may be implemented via other non-ablative laser therapies, such as laser-incised custom lenticule shapes and subsequent extraction and laser-based corneal incision patterns.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with a input device of processor 22, the storage media may also be remotely operatively coupled with processor by means of network connections such as the internet, and by wireless methods such as infrared. Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
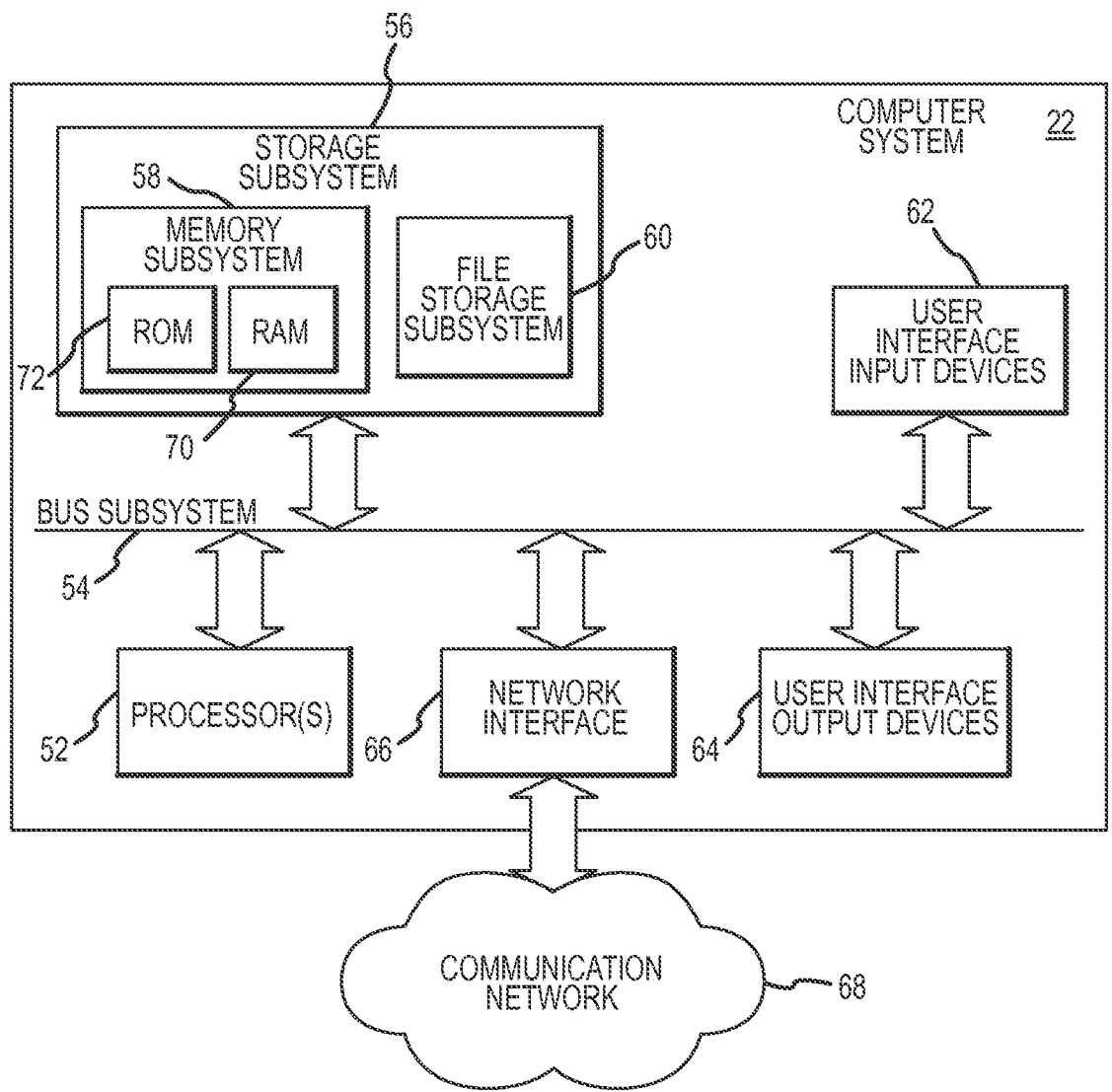
FIG. 2 illustrates a simplified computer system according to embodiments of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
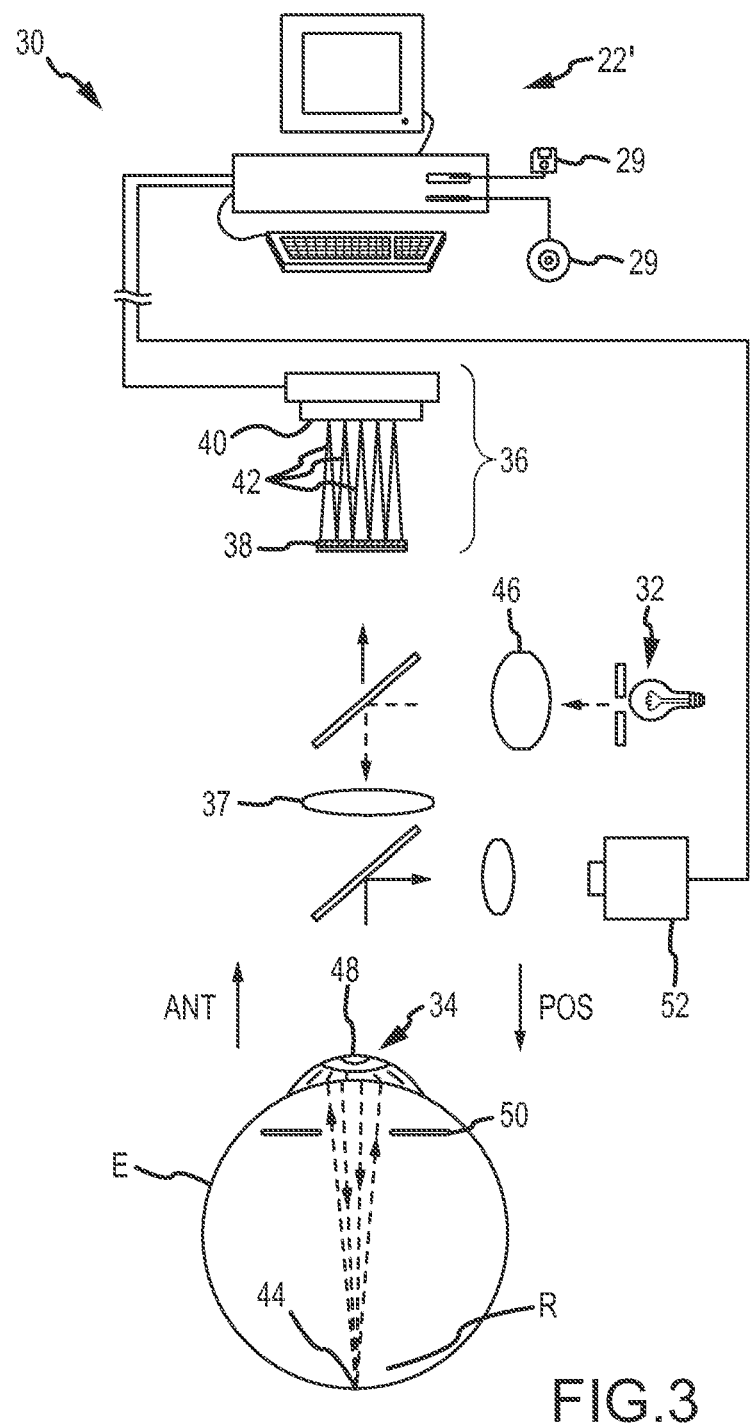
FIG. 3 illustrates a wavefront measurement system according to embodiments of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
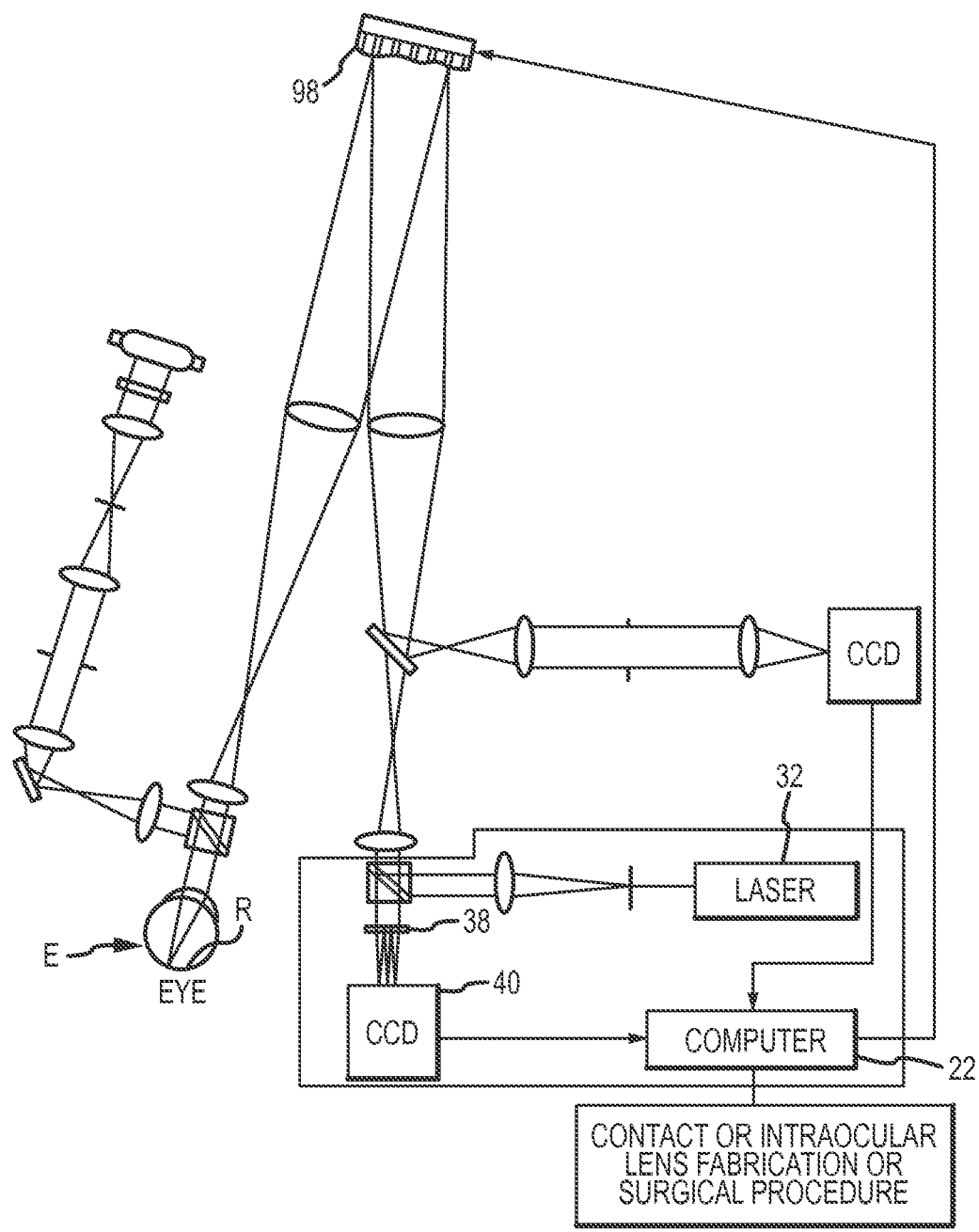
FIG. 3A illustrates another wavefront measurement system according to embodiments of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from AMO MANUFACTURING USA, LLC. MILPITAS, California. One embodiment includes a WaveScan system with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention. Relatedly, embodiments of the present invention encompass the implementation of any of a variety of optical instruments provided by AMO WaveFront Sciences, LLC, including the COAS wavefront aberrometer, the ClearWave contact lens aberrometer, the CrystalWave IOL aberrometer, and the like.

Relatedly, embodiments of the present invention encompass the implementation of any of a variety of optical instruments provided by WaveFront Sciences, Inc., including the COAS wavefront aberrometer, the ClearWave contact lens aberrometer, the CrystalWave IOL aberrometer, and the like. Embodiments of the present invention may also involve wavefront measurement schemes such as a Tscherning-based system, which may be provided by Alcon, Inc. Embodiments of the present invention may also involve wavefront measurement schemes such as a ray tracing-based system, which may be provided by Tracey Technologies, Corp.

The present invention is useful for enhancing the accuracy and efficacy of photorefractive keratectomy (PRK), laser in situ keratomileusis (LASIK), laser assisted epithelium keratomileusis (LASEK), and the like.

The techniques of the present invention can be readily adapted for use with existing laser systems, including the Excimer laser eye surgery systems commercially available from AMO Manufacturing USA, LLC in Milpitas, Calif.

Other suitable laser systems are manufactured by Alcon, Bausch & Lomb, Wavelight, Schwind, Zeiss-Meditec, Lasersight, Nidek and the like. By providing improved corneal ablation profiles for treating optical defects, the present invention may allow enhanced treatment of patients who have heretofore presented difficult or complicated treatment problems. When used for determining, deriving, and/or optimizing prescriptions for a particular patient, the systems and methods may be implemented by calculating prescriptions for a range of patients, for example, by calculating discrete table entries throughout a range of patient characteristics, deriving or empirically generating parametric patient characteristic/prescription correlations, and the like, for subsequent use in generating patient-specific prescriptions.

Ocular wavefront transformation is suitable for use in wavefront optics for vision correction because the pupil size of a human eye often changes due to accommodation or the change of lighting, and because the pupil constriction is commonly not concentric. Certain features of these ocular effects are discussed in, for example, Wilson, M. A. et al., *Optom. Vis. Sci.*, 69:129-136 (1992), Yang, Y. et al., *Invest. Ophthal. Vis. Sci.*, 43:2508-2512 (2002), and Donnenfeld, E. J., *Refract. Surg.*, 20:593-596 (2004). For example, in laser vision correction, the pupil size of an eye is relatively large when an ocular wavefront is captured under an aberrometer. To obtain the entire ocular wavefront, it is often recommended that the ambient light be kept low so as to dilate the pupil size during the wavefront exam. A larger wavefront map can provide surgeons the flexibility for treatment over a smaller zone, because the wavefront information over any smaller zone within a larger zone is known. When a smaller wavefront map is captured, however, it is also useful to devise an accurate treatment over a larger zone. When the patient is under the laser, the pupil size can change due to changes in the ambient light. In many cases, the surgery room is brighter than a wavefront examination room, in particular when the patient is under the hood. Furthermore, the cyclorotation of the eye due to the change from a sitting position to a laying position can make the pupil center change between the wavefront capture and the laser ablation, for example as discussed in Chernyak, D. A., *J. Cataract. Refract. Surg.*, 30:633-638 (2004). Theoretically, it has been reported that correction of error due to rotation and translation of the pupil can provide significant benefits in vision correction. Certain aspects of these ocular effects are discussed in Bari, S. et al., *Appl. Opt.*, 39:3413-3420 (2000) and Guirao, A. et al., *J. Opt. Soc. Am. A*, 18:1003-1015 (2001).

Basis Data Techniques

Embodiments of the present invention encompass basis data architectures that are configured to efficiently operate with annular, elliptical, and slit laser beam shapes, and to account for position-dependent ablation features.

Beam Pulse Size and Shape

Variable Spot Scanning (VSS) refers to an excimer laser technique for scanning beams at variable pulse diameters at different locations (e.g. x,y position) over an entire treatment area. Variable Repetition Rate (VRR) refers to a pulse-packing technique, whereby the repetition rate of a laser can be varied, for example from 6 Hz to 20 Hz.

Figure 4:
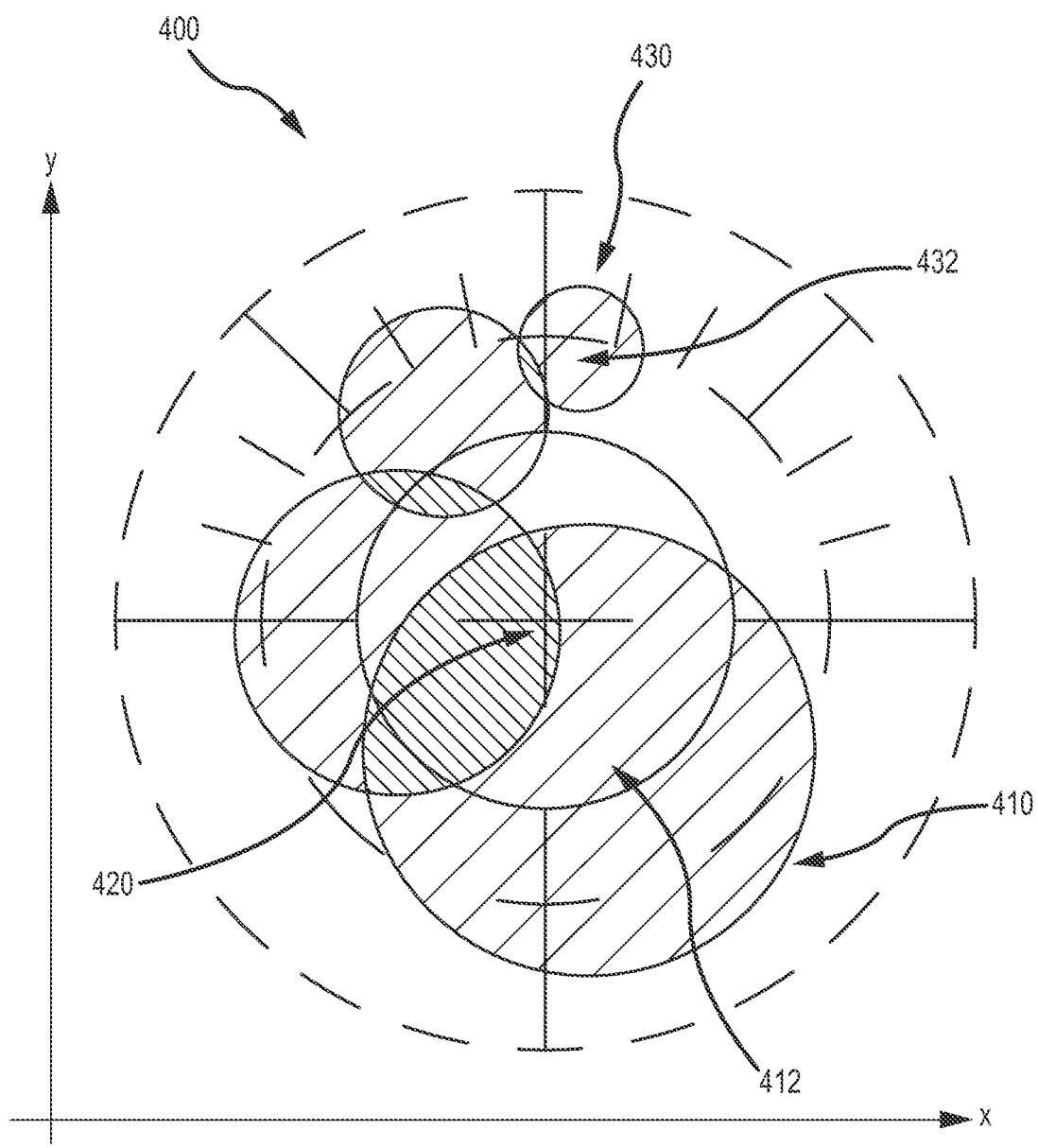
FIG. 4 depicts aspects of a treatment pattern or protocol having ablation pulses, according to embodiments of the present invention.

An exemplary illustration of the VSS technique is shown in FIG. 4. As depicted here, a treatment pattern 400 may include a larger ablation pulse 410 having a center 412 that is near to the treatment center 420, and a smaller ablation pulse 430 having a center 432 that is distant from the treatment center. In some instance, the beam diameter during a treatment may range in size from 0.65 mm to 6.5 mm. As the beam is directed to different x,y locations on the cornea, it may be assumed that the eye remains relatively fixed with regard to the treatment center, because eye movements during the laser ablation may be compensated by the tracking system. Embodiments of the present invention encompass systems and methods for refractive surgery which take into account variations in laser pulse depth and pulse shape which are dependent upon the pulse position.

Figure 4A:
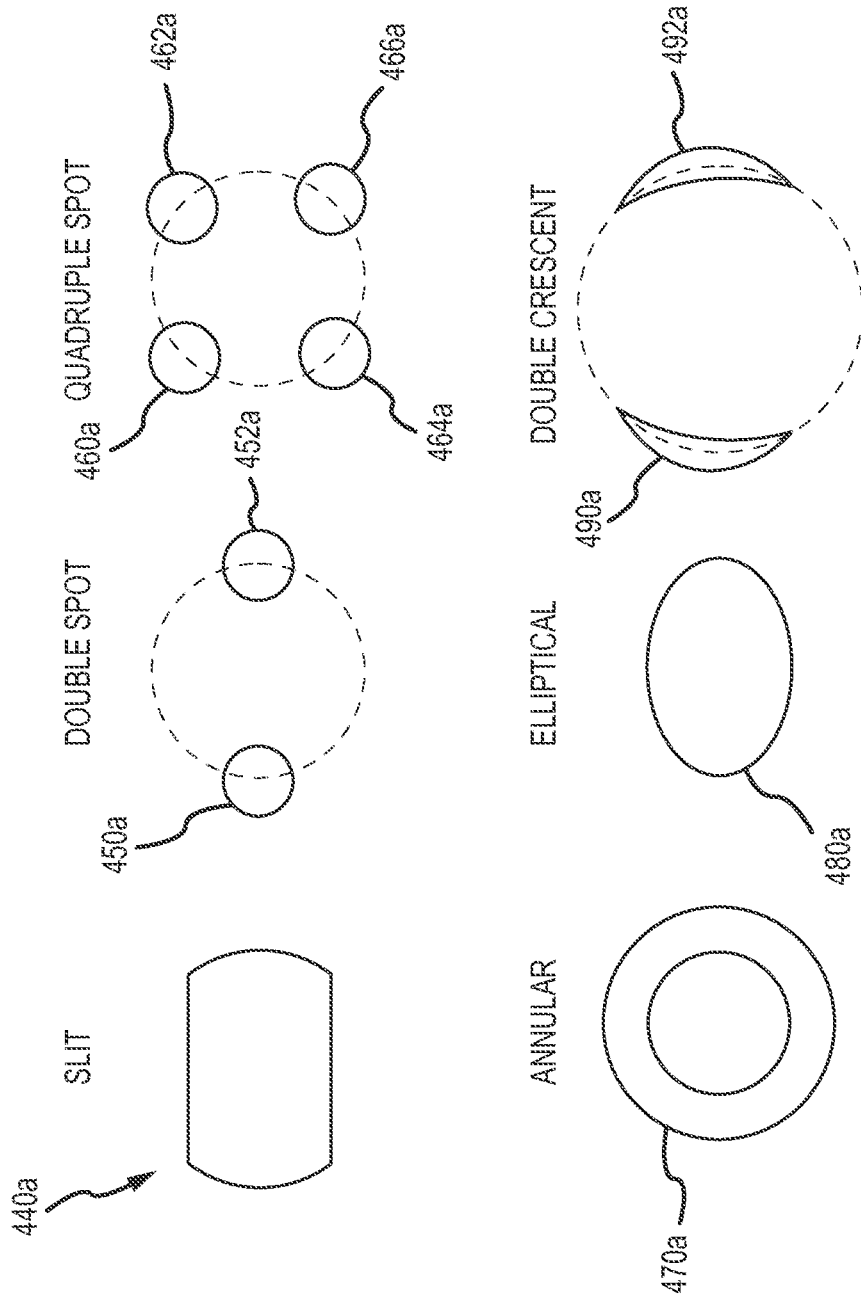
FIGS. 4A, 4B, 4C, and 4D depict aspects of vision condition treatments and related system and method elements for providing such treatments, according to embodiments of the present invention.

FIG. 4A illustrates various types of spot shapes, according to embodiments of the present invention. As shown here, in addition to single spots, pulse shapes can be provided as a slit 440a, as multiple spots such as double spots 450a and 452a or as quadruple spots 460a, 462a, 464a, and 466a, as an annulus or annular shape 470a, as an ellipse or elliptical shape 480a, as double crescents 490a and 492a, and the like.

Figure 4B:
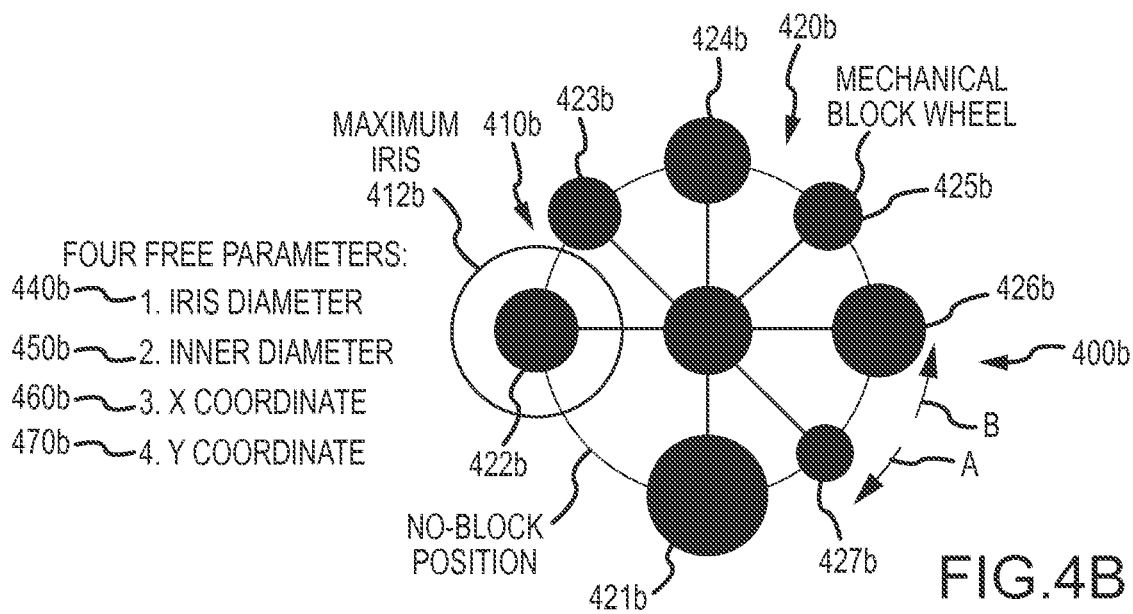

FIG. 4B depicts aspects of a technique or mechanism for realizing annular spot shapes, according to embodiments of the present invention. As shown here, a mechanical block assembly 400b includes an adjustable iris mechanism 410b that provides an outer or maximum iris diameter 412b, and a central block mechanism 420b that can rotate about an axis in a clockwise direction as indicated by arrow A or a counterclockwise direction as indicated by arrow B. Central block mechanism 420b can include one or more obscuration elements. For example, central block mechanism 420b can include a first obscuration element 421b, a second obscuration element 422b, a third obscuration element 423b, a fourth obscuration element 424b, a fifth obscuration element 425b, a sixth obscuration element 426b, and a seventh obscuration element 427b. Central block mechanism 420b can be rotatably adjusted such that an obscuration element is positioned along the path of the laser beam and aligned with iris mechanism 410b. As shown here, second obscuration element 422b is positioned relative to iris mechanism 410b, such that an annular portion of the laser beam is transmitted through an annular shaped passage while the central portion of the laser beam is blocked by the obscuration element. In this way, the outer diameter of the annular beam shape corresponds to the maximum or outer iris diameter 412b and the inner diameter of the annular beam shape corresponds to the diameter of the obscuration element 422b.

The mechanical block assembly 400b may operate with four free parameters, including iris diameter 440b, inner diameter 450b, X coordinate 460b, and Y coordinate 470b. With regard to the first parameter, the iris mechanism 410b can be adjusted to any dimension as desired, so as to provide the outer diameter of the annular shape. For example, iris mechanism 410b can be adjusted to a 6.5 mm outer diameter, a 6.0 mm outer diameter, a 5.5 mm outer diameter, and the like. With regard to the second parameter, the central block mechanism 420b can provide a 4.875 mm obscuration block, a 4.5 mm obscuration block, a 4.125 obscuration block, and the like, for the inner diameter dimension of the annular shape. In some cases where a circular ablation pulse or shape is desired, central block mechanisms can be adjusted, for example so that an obscuration blank is aligned with the iris 410b, so that a laser beam can pass through the iris without obscuration of a central portion of the laser beam. Related annular and other spot shape techniques are further described in US 2012/0083776, the content of which is incorporated herein by reference.

Figure 4C:
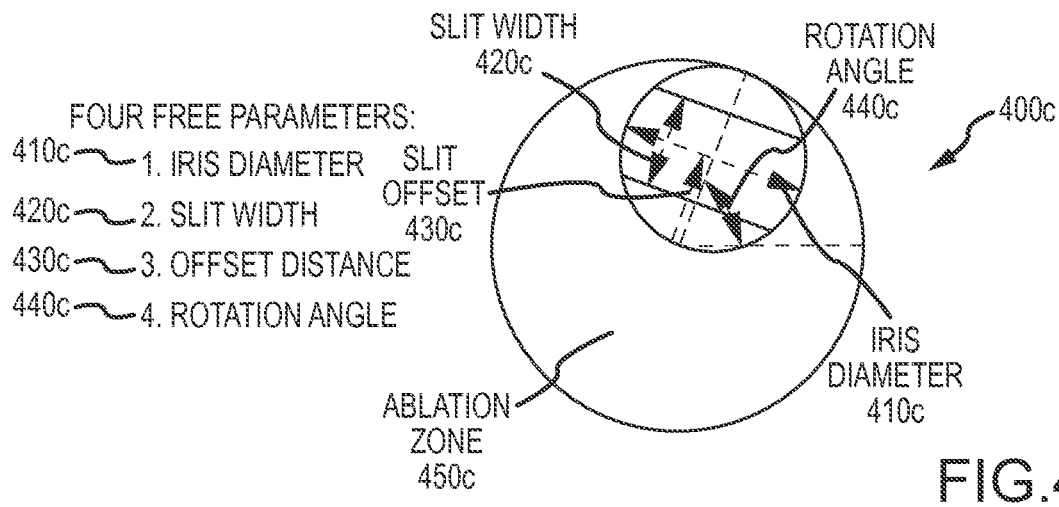

FIG. 4C depicts aspects of a technique or mechanism for realizing slit spot shapes. As shown here, the slit mechanism 400c can be configured to operate with four parameters, including iris diameter 410c, slit width 420c, offset distance 430c, and rotation angle 440c. Beam pulse shapes can be delivered at various locations within an ablation zone 450c. Related slit and other spot shape techniques are further described in U.S. Pat. Nos. 6,193,710 and 6,203,539, the contents of which are incorporated herein by reference.

Figure 4D:
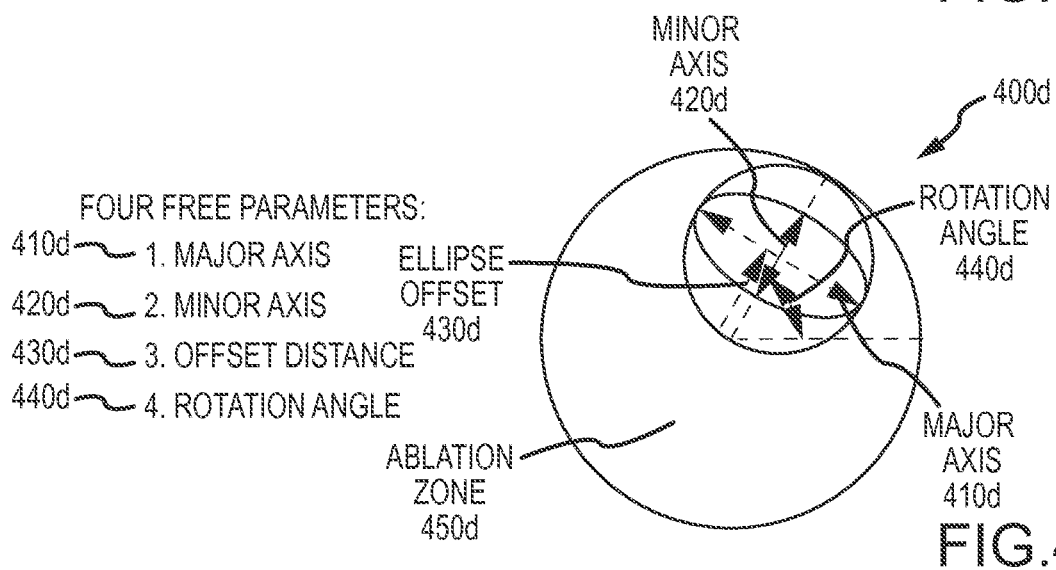

FIG. 4D depicts aspects of a technique for realizing elliptical spot shapes. As shown here, the ellipse mechanism 400d can be configured to operate with four parameters, including major axis 410d, minor axis 420d, offset distance 430d, and rotation angle 440d. Beam pulse shapes can be delivered at various locations within an ablation zone 450d.

Figure 5A:
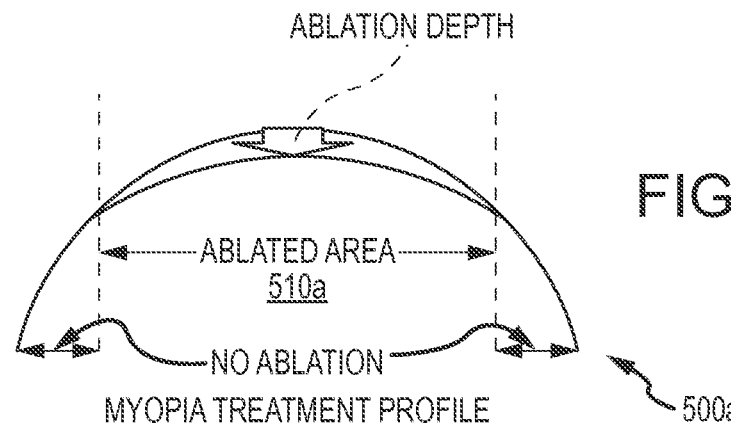
FIGS. 5A, 5B, 5C, and 5D depict aspects of vision condition treatments and related system and method elements for providing such treatments, according to embodiments of the present invention.
Figure 5B:
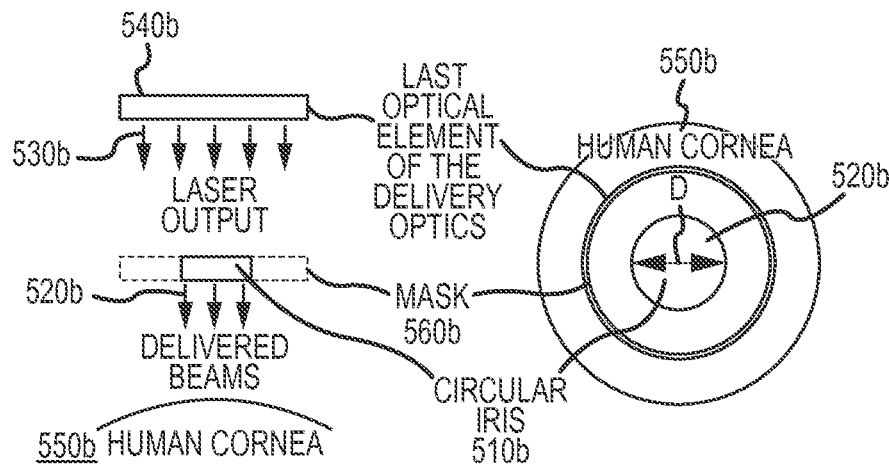

As depicted in FIG. 5A, a myopia treatment can involve administering a myopia treatment profile 500a, for example by ablating a central area 510a of the patient corneal surface. For refractive surgery using VSS Refractive™ technology, relatively large (e.g. up to 6.5 mm in diameter) circularly-shaped laser beams can be used. Hence, because a single large circular pulse can cover most of all of the treatment area (e.g. ablated area 510a), VSS with circular pulses provide an extremely efficient approach for delivering myopic treatment ablations. For example, a VSS myopia surgery can be performed within a minute. Relatedly, FIG. 5B provides a side view and a top view of a circular iris 510b that can be used to form a circular laser beam pulse 520b. In operation, the mask 560b can be considered as part of the laser delivery apparatus, such that the mask 560b remains stationary relative to the laser output beam 530b, as the beam is scanned at various locations on the eye. Hence, the mask 560b and laser beam 530b move or translate in the x,y plane, relative to the eye. The mask 560b can operate to define or otherwise influence the shape of the iris 510b, and can be positioned between the laser delivery optics 540b and the patient eye 550b. The size of the mask 560b can be adjusted in small increments so as to vary the size of the iris 510b accordingly. In this way, a mask 560b can be used to generate a circular beam pulse 520b, and the circular beam pulse 520a can have a variable diameter D and a variable location (e.g. x,y).

Figure 5C:
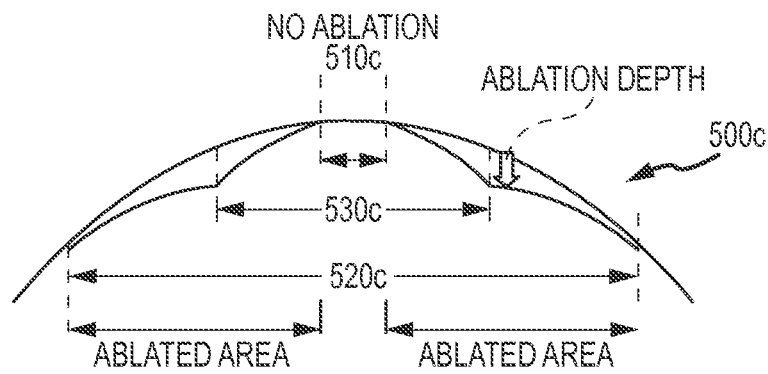

In contrast to a typical myopia treatment, a typical hyperopia treatment involves creating a donut-like ablation shape or treatment profile 500c, such as that shown in FIG. 5C, where there is little or no ablation at the central part 510c of the cornea. The treatment may involve an 8 to 9 mm diameter ablation zone 520c and a 6 mm optical zone 530c, for example.

Figure 5D:
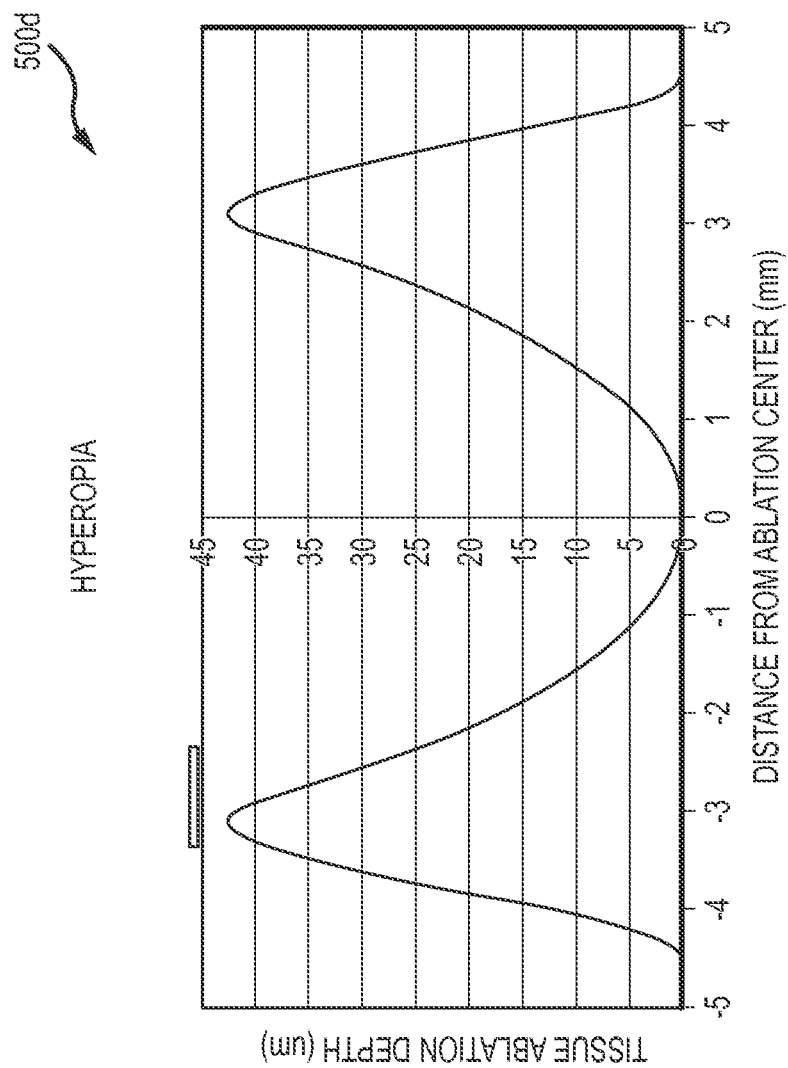

FIG. 5D depicts aspects of an exemplary hyperopic ablation shape 500d according to embodiments of the present invention. Such a hyperopic shape can be configured to provide, for example, a +3 Diopter treatment.

For hyperopia treatments, it may be difficult to make extensive use of a large circular pulse (e.g. 6.5 mm in diameter). Accordingly, smaller circular pulse sizes can be used (e.g. maximum of 4.5 mm in diameter), although the efficiency of the ablation will likely be diminished. Similarly, for a mixed astigmatism treatment where one principal meridian is hyperopic and the other myopic, the efficiency is diminished when using smaller circular pulses to fit the target shape, due to the hyperopic meridian in the mixed astigmatic eye, and the ablation time is increased.

Embodiments of the present invention encompass annular, elliptical, and slit laser beam shape techniques for use with hyperopic and mixed astigmatism treatments. Exemplary aspects of such annular, elliptical, and slit pulse shapes are depicted in the side and top views provided in FIGS. 6A, 6B, and 6C, respectively. As depicted here, different iris types can be used to produce different pulse beam shapes.

Figure 6A:
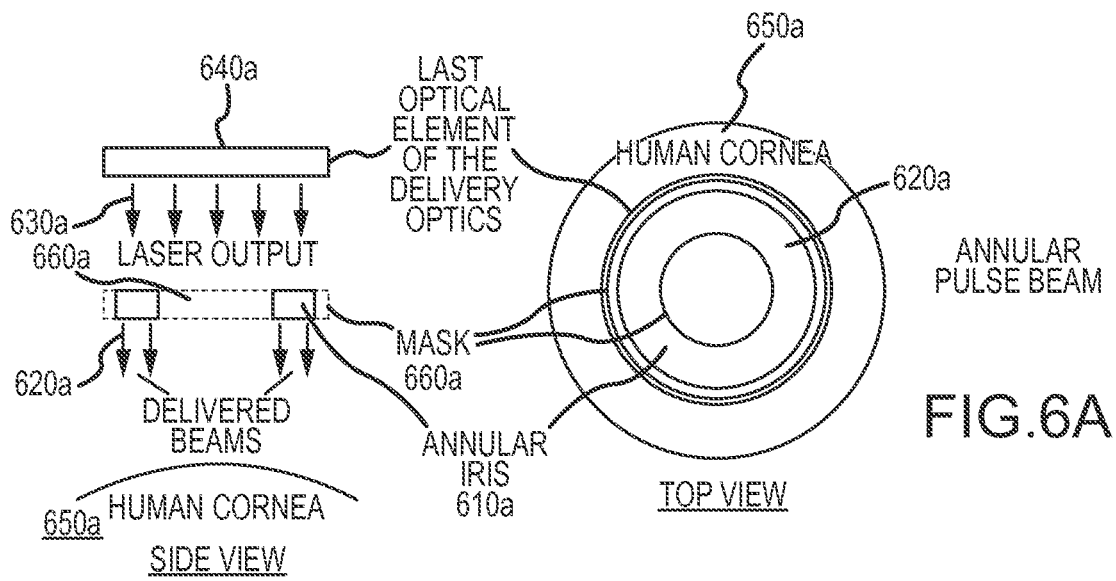
FIGS. 6A, 6B, and 6C depict aspects of vision condition treatments and related system and method elements for providing such treatments, according to embodiments of the present invention.

For example, FIG. 6A provides a side view and a top view of an annular iris 610a that can be used to form an annular laser beam pulse 620a. In operation, the mask 660a can be considered as part of the laser delivery apparatus, such that the mask 660a remains stationary relative to the laser output beam 630a, as the beam is scanned at various locations on the eye. Hence, the mask 660a and laser beam 630a move or translate in the x,y plane, relative to the eye. The mask 660a can operate to define or otherwise influence the shape of the iris 610a, and can be positioned between the laser delivery optics 640a and the patient eye 650a. The size of the mask 660a can be adjusted in small increments so as to vary the size of the iris 610a accordingly. In this way, a mask 660a can be used to generate an annular beam pulse 620a, and the annular beam pulse 620a can have a variable inner diameter, a variable outer diameter, and a variable location (e.g. x,y).

Figure 6B:
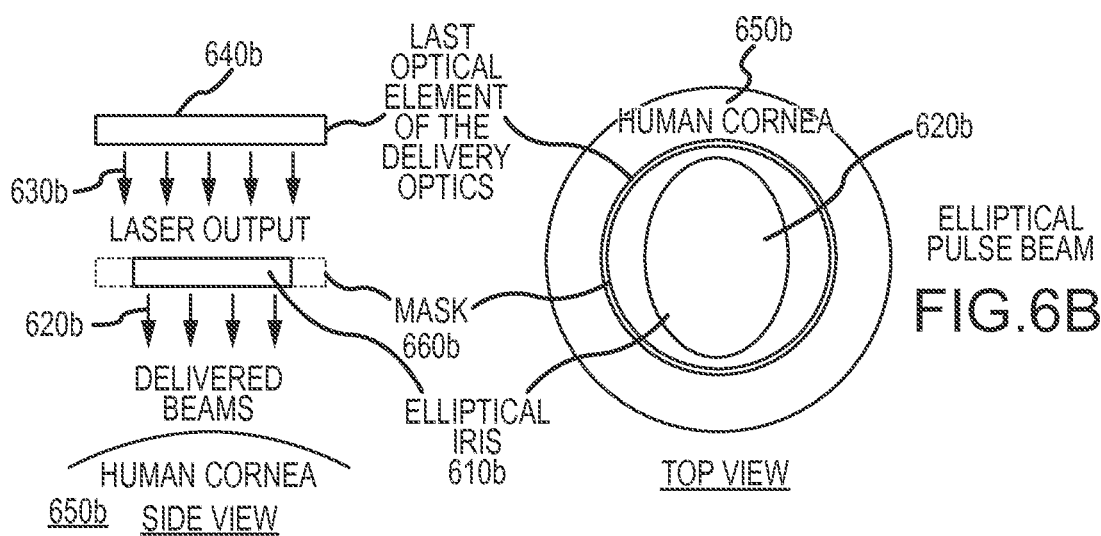

FIG. 6B provides a side view and a top view of an elliptical iris 610b that can be used to form an elliptical laser beam pulse 620b. In operation, the mask 660b can be considered as part of the laser delivery apparatus, such that the mask 660b remains stationary relative to the laser output beam 630b, as the beam is scanned at various locations on the eye. Hence, the mask 660b and laser beam 630b move or translate in the x,y plane, relative to the eye. The mask 660b can operate to define or otherwise influence the shape of the iris 610b, and can be positioned between the laser delivery optics 640b and the patient eye 650b. The size of the mask 660b can be adjusted in small increments so as to vary the size of the iris 610b accordingly. In this way, a mask 660b can be used to generate an elliptical beam pulse 620b. The elliptical beam pulse 620b can have a desired major axis, minor axis, offset distance, and rotation angle.

Figure 6C:
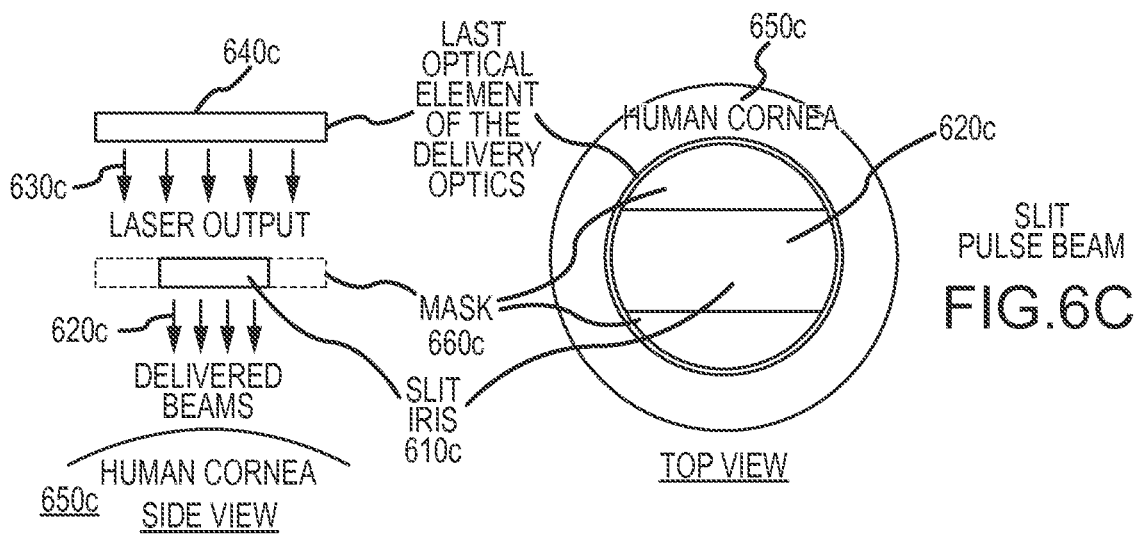

FIG. 6C provides a side view and a top view of a slit iris 610c that can be used to form a slit laser beam pulse 620c. In operation, the mask 660c can be considered as part of the laser delivery apparatus, such that the mask 660c remains stationary relative to the laser output beam 630c, as the beam is scanned at various locations on the eye. Hence, the mask 660c and laser beam 630c move or translate in the x,y plane, relative to the eye. The mask 660c can operate to define or otherwise influence the shape of the iris 610c, and can be positioned between the laser delivery optics 640c and the patient eye 650c. The size of the mask 660c can be adjusted in small increments so as to vary the size of the iris 610c accordingly. In this way, a mask 660c can be used to generate a slit beam pulse 620c. The slit beam pulse 620b can have a desired iris diameter, slit width, offset distance, and rotation angle.

Beam Pulse Position (Ablation Depth and Shape)

Figure 7:
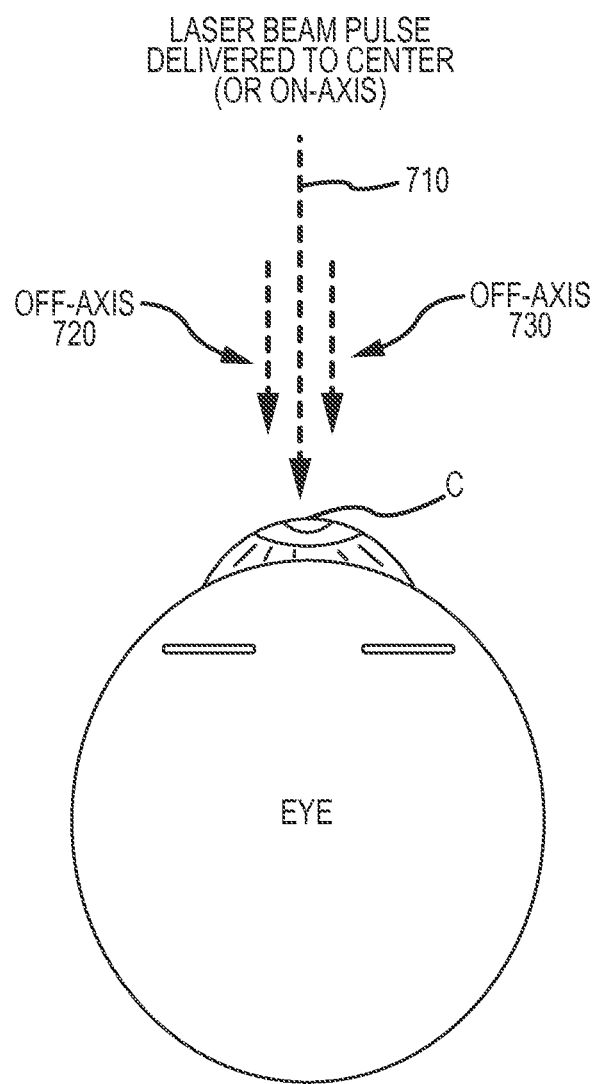
FIG. 7 depicts aspects of a treatment pattern or protocol having ablation pulses, according to embodiments of the present invention.

As depicted in FIG. 7, during an ablation treatment the beam pulses may be directed to various locations on the cornea. Some pulses 710 may be centered about or otherwise directed to the center of the cornea C. Other pulses 720, 730 may be delivered at an off-axis location.

In some instances, the ablation depth of an off-center pulse (on a curved ablation surface) can be non-uniform, for example with the inner edge of the profile being deeper than the outer edge. For example, as shown in FIG. 8A, regardless of whether the beam is off centered (e.g. off-axis 810a) or not (e.g. on-axis 820a), the laser delivery can be perpendicular to the curved surface 830a (e.g. parallel pulse delivery paths). Yet the ablation depth can vary according to the positioning of the beam pulse. In some instances, a greater amount of offset may correspond to a greater variability in the pulse depth profile. An ablation center can correspond to particular x,y scanning location (e.g. 0,0). At such a location, the system can be configured to direct the laser beam directly toward the surface of the eye. For example, the on-axis beam pulse 820a shown here can produce an ablation profile of uniform depth D. In contrast, an off-axis beam pulse 810a can produce an ablation profile 850a that varies in depth D (e.g. more depth toward the center of the curved surface, and less depth away from the center).

As discussed elsewhere herein (e.g. with respect to FIGS. 9A and 9B) in some cases, when the laser beam is directed to an off-center position (e.g. decentered relative to the 0,0 scanning position), the laser beam may be slightly tilted. According to some embodiments, the term "on-axis" refers to a main or central ray propagated by or through the optical system as a straight line.

Figure 8B:
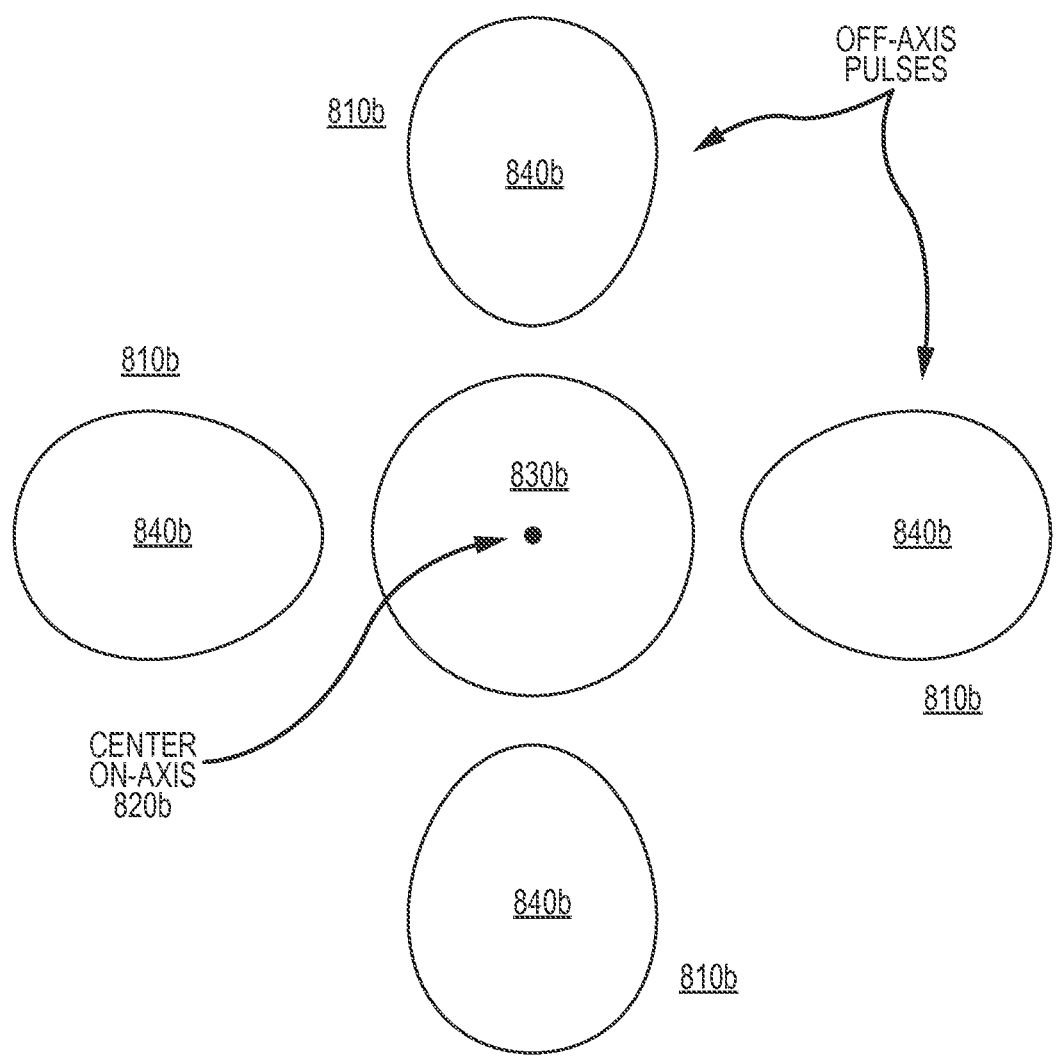

Similarly, as depicted in FIG. 8B, when the laser beam is delivered off-center (again, considering a curved ablation surface) to an off-center location 810b, the spot profile can become skewed in a tear-drop or egg shape. It has been observed that when the laser pulse is sufficiently decentered from the optical axis 820b, the ablation spot may no longer be rotationally symmetrical. This may be referred to as a "cosine effect" with the loss of energy due to the curved corneal surface. In some instances, the skewed shape can be referred to as a rotational asymmetry. In some instances, both on-axis 830b and off-axis 840b ablation pulses will retain their shape as formed by the mask or iris. The depiction of FIG. 8B represents a situation where circular beam shapes are directed onto a spherical or curved surface, such that when viewed from the beam origination location, the ablation spots appear circular in shape. However, as the curved surface is flattened (e.g. similar to a map projection technique where a cartographer flattens the globe to form a flat map), the tear-drop or irregular shapes of the off-axis ablation pulses become apparent.

Hence, as illustrated in FIGS. 8A and 8B, laser beam offset can have an effect in terms of ablation pulse depth and/or shape, relative to a curved surface such as the cornea. Embodiments of the present invention encompass apodization or other compensation techniques that account for such effects.

Figure 9A:
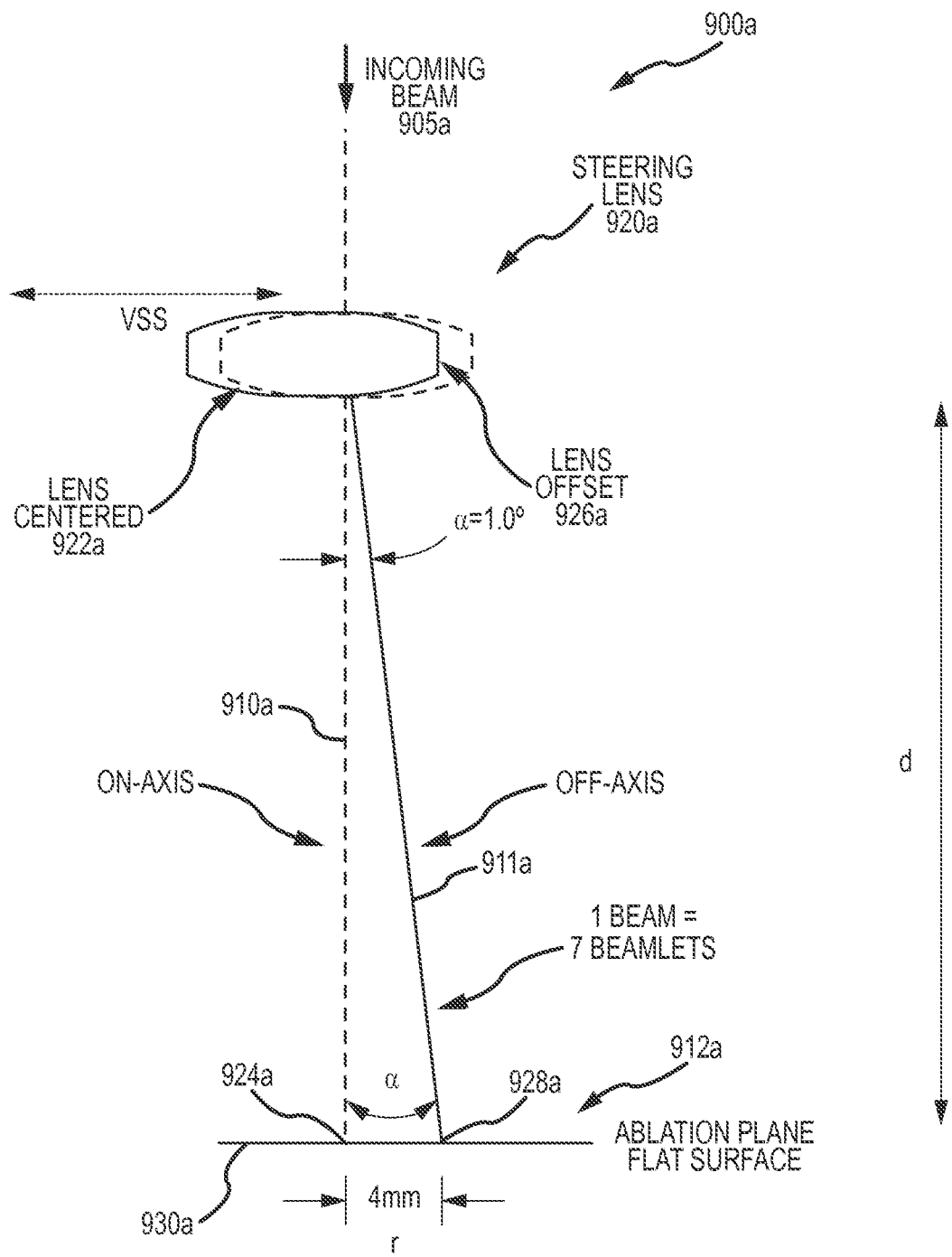
FIGS. 9A and 9B depict aspects of a treatment patterns or protocols having ablation pulses, according to embodiments of the present invention.

As depicted in FIG. 9A, a laser beam directing mechanism 900a can operate to scan a beam 910a toward various locations. For example, a biconvex lens can be used to steer the beam as desired. As shown here, when moved toward the left, a biconvex lens 920a can steer the beam toward the right. In some embodiments, such scanning can be implemented with VSS Refractive™ technology. For illustrative purposes, the ablation plane 912a is depicted here as a flat surface or configuration, however in use the beam is typically directed toward a curved corneal surface. Where an optical or steering lens 920a is disposed at a first location 922a (dashed lines) such as a centered or on-axis orientation, the beam 910a is directed toward a first scanning location 924a (e.g. 0, 0). Similarly, where the optical lens 920a is disposed at a second location 926a (solid lines) such as an offset or off-axis orientation, the beam 911a is directed toward a second scanning location 928a (e.g. 0, 4 mm). Hence, a steering or moveable lens 920a can be used to direct an incoming beam 905a toward various locations across the ablation surface 930a. In some instances, the scanning locations (e.g. locations 924a and 928a) can be characterized as occurring at a radial distance r relative to a central location (0, 0). In the embodiment shown here, the beams can be steered from a common point or element (e.g. corresponding to the steering lens 920a), which is a distance d from the ablation surface 930a. In some instances, distance d can be about 10 inches. As discussed elsewhere herein (e.g. with regard to FIGS. 5B and 6A to 6C), a beam delivery system may also include a mask. The mask is typically disposed between the ablation surface and the steering lens, and the mask may or may not be fixed relative to the steering lens. With return reference to FIG. 9A, the off-axis beam 911a may be oriented at an angle α relative to the on-axis beam 910a. For example, where the radial distance r is about 4 mm, the angle α can be about 1 degree. In some cases, the beam (e.g. 910a or 911a) can be composed of multiple beamlets. For example, seven beamlets can be combined to form a beam.

Figure 9B:
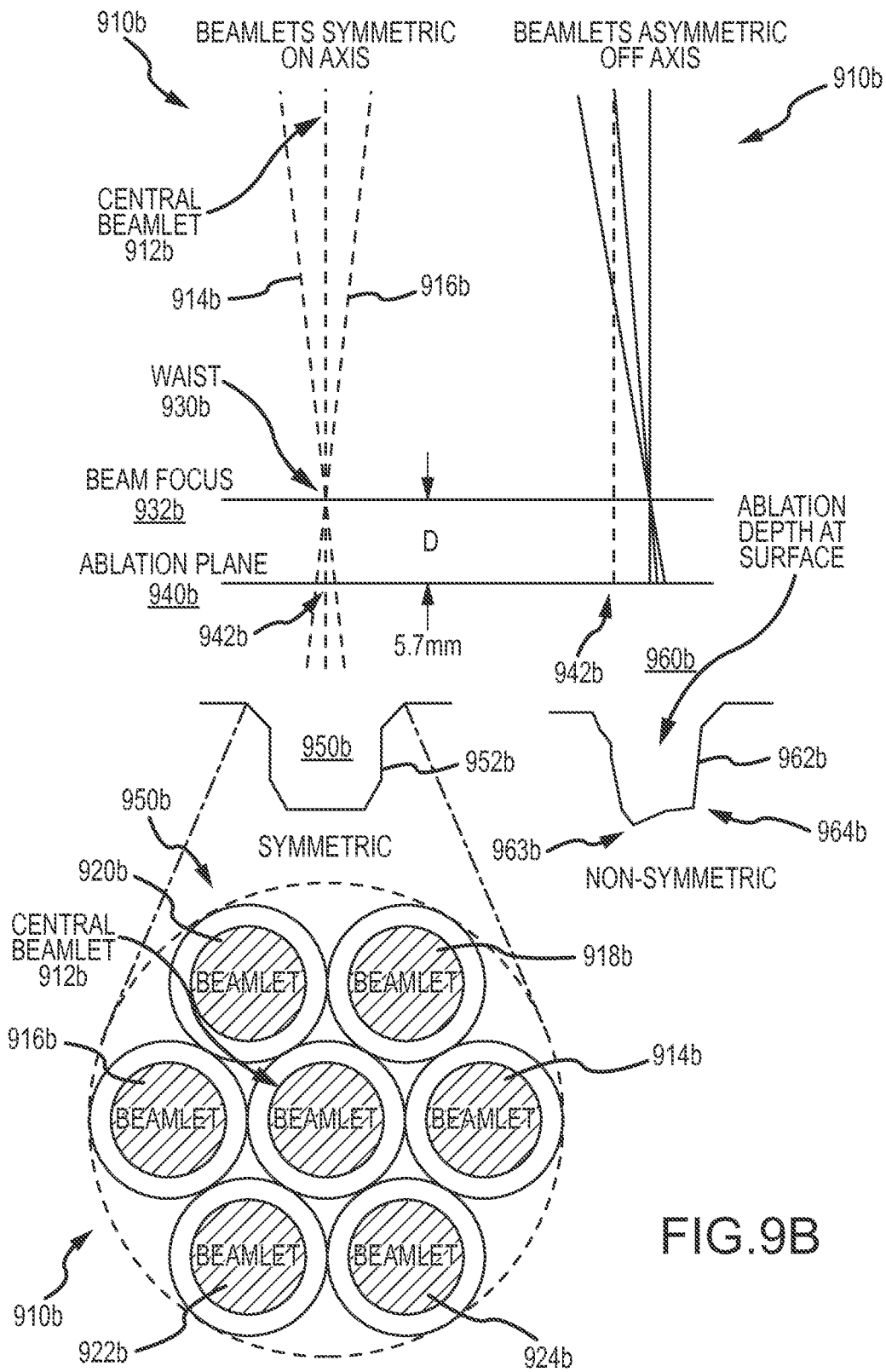

As depicted in FIG. 9B, an incoming beam 910b may include multiple beamlets 912b, 914b, 916b. For example, a laser beam 910b may include seven beamlets (912b, 914b, 916b, 918b, 920b, 922b, 924b). The left panel depicts the laser beam as it is steered at an on-axis orientation. The beamlets can overlap at a beam waist 930b or beam focus plane 932b. The overlapping beams at the waist 930b can form or approach a single circle shape. As shown here, the beam focus plane 932b is at a distance from the treatment or ablation plane 940b. Again, for illustrative purposes, the ablation plane 940b is depicted here as a flat configuration, however in use the beam is typically directed toward a curved corneal surface. In some instances, the beam focus plane or surface 932b can be separated from the treatment plane or surface 940b by a distance D, for example of about 5.7 mm. As shown here, the beamlets are slightly diverged at the ablation plane or surface 940b. The beamlets may or may not be overlapping at the ablation surface 940b. As depicted here, the combined effect of the seven beamlets at the ablation surface 940b can be considered to create a circular ablation spot 950b. When ablating on-axis, there may be one central beamlet 912b that is perpendicular to the ablation surface 940b, and six other beamlets (914b, 916b, 918b, 920b, 922b, 924b) that are each oriented at a common angle relative to the central beamlet 912b. In this way, the beamlets of the beam 910b operate to form a symmetric pulse ablation pattern or spot 950b. As shown here, ablation spot 950b may have a uniform or symmetric ablation depth, or a uniform or symmetric shape profile 965b.

When the beam 910b is steered at an off-axis orientation, as depicted in the right panel, the symmetry of the beamlets within the beam is affected. For example, as shown here, some beamlets may become more perpendicular relative to the ablation surface, and other beamlets may be oriented at a lower incidence angle. Due to the combination of beamlets oriented at various angles non-uniform angles or steepness relative to the ablation surface 940b, the ablation spot 960b is non-symmetric. For example, the ablation spot may have a non-uniform or non-symmetric ablation depth, or a non-uniform or non-symmetric shape profile 962b. Put another way, the uniformity of the pulse shape deviates as the beam is delivered off-axis (e.g. relative to a flat ablation surface). This is because the ablation is created by multiple beamlets, which are symmetric when on-axis, but when steered in an off-axis orientation, the intersection of the beamlets at the ablation surface 940b no longer forms a symmetric pattern. This asymmetry as the beamlets impinge upon the ablation surface 940b can lead to hotter and colder positions in the beam profile. In some instances, the degree or extent of the asymmetry or non-uniformity can increase as the beam pulse is directed at further distances from the on-axis or central location 942b. For example, there may a significant asymmetry within the orientation of the beamlets at or near a transition zone (e.g. toward outer periphery) of an ablation pattern. A mask may be disposed between the beam focal plane 940b and the beam delivery optics.

Accordingly, in some instances, the ablation depth of an off-center pulse (on a flat ablation surface) can be non-uniform, for example with the inner edge 963b of the profile being deeper than the outer edge 964b. Hence, the ablation depth can vary according to the positioning of the beam pulse. In some instances, a greater amount of offset may correspond to a greater variability in the pulse depth profile. An ablation center can correspond to particular x,y scanning location (e.g. 0,0). At such a location, the system can be configured to direct the laser beam directly toward the surface of the eye (e.g. left panel of FIG. 9B). When the laser beam is directed to an off-center position (e.g. decentered relative to the 0,0 scanning position), the laser beam may be slightly tilted (e.g. right panel of FIG. 9B). According to some embodiments, the term "on-axis" refers to a main or central ray propagated by or through the optical system as a straight line. When the laser beam is delivered off-center (again, considering a flat ablation surface), the spot profile can become skewed or asymmetric. As illustrated in the left panel, the ablation spot 950b is aligned with the on-axis or central location 942b. In contrast, as illustrated in the right panel, the ablation spot 960b is offset from the on-axis or central location 942b.

Hence, as illustrated in FIGS. 9A and 9B, laser beam offset can have an effect in terms of ablation pulse depth and/or shape, relative to a flat ablation surface. Embodiments of the present invention encompass apodization or other compensation techniques that account for such effects, particularly when applied to a curved ablation surface such a patient cornea.

Basis Data Architecture

Embodiments of the present invention encompass basis data architectures that are configured to efficiently operate with annular, elliptical, and slit laser beam shapes, and to account for position-dependent ablation features.

Figure 10:
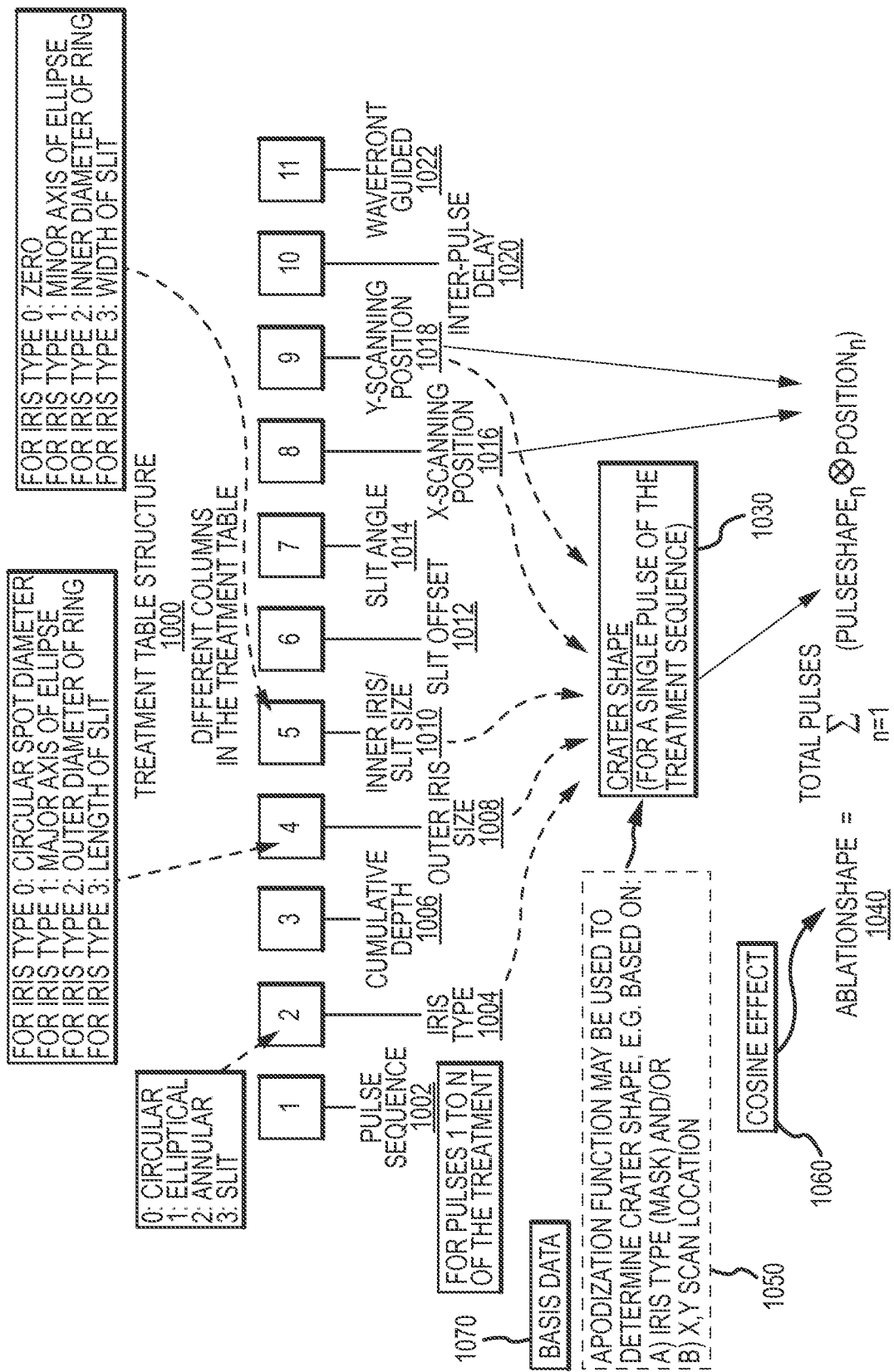
FIG. 10 depicts aspects of treatment target ablation shape development, according to embodiments of the present invention.

FIG. 10 illustrates an exemplary architectural structure 1000 for a treatment table. In general, a treatment file or treatment table stores or contains commands for an excimer laser to control various aspects of the corneal ablation process, such as the size of the laser pulses, the relative scanning locations and rotation angles, the delay between subsequent pulses (e.g. interpulse delay), and the like. In operation, the laser control software can read the treatment file into the memory, and the laser system can deliver each of the pulses according to the commands. A treatment table can be generated by treatment table engine, for example, using VSS Refractive™ and/or VRR technology. As depicted here, the treatment table includes a set of instructions or information (e.g. row entries) for an individual pulse of an ablation treatment.

In the treatment table architecture structure of FIG. 10, Column 1 provides the pulse sequence number 1002 (e.g. for a treatment protocol that includes n pulses). Column 2 shows the iris type 1004 (e.g. 0 for circular, 1 for elliptical, 2 for annular, and 3 for slit). For example, these iris types correspond to the iris shapes shown in FIGS. 5B and 6A-C. If there are other iris types, the number can be extended. Column 3 is for the cumulative depth 1006 (tissue depth in microns). This column represents the total depth of the treatment, or the sum of the pulse ablation depths.

Relative to the treatment table, the basis data can be defined or stored in a separate file. According to some embodiments, certain features of the treatment table can be used to select information from a basis data file. For example, data associated with Column 4 (outer iris size 1008) of the treatment table can be used to determine which values can be selected from the basis data file. The information obtained from the basis data file can be read into a memory, for example during start up of the treatment software. According to some embodiments, the basis data is read in with respect to a treatment table feature (e.g. circular iris size), and mask and/or apodization techniques can be applied to the basis data, for example during the assembly of the entire ablation profile.

Column 4 is for the outer iris size 1008 (diameter in mm). For the general circular pulse (e.g. iris type 0), this will be the spot size. For the elliptical iris type (e.g. iris type 1), this will be the (major) long axis length of the ellipse. For the annular iris (e.g. iris type 2), this will be the outer iris size. For the slit iris type (e.g. iris type 3), this will be the length of the slit.

Column 5 is for the inner iris size or the slit width 1010. For the general circular iris type (e.g. iris type 0), this will be zero. For the elliptical iris type (e.g. iris type 1), this will be the minor (short) axis length of the ellipse. For the annular iris type (e.g. iris type 2), this will be the inner iris size. That is, the laser beam will pass the energy between the two circles having the outer boundary of the outer iris size and the inner boundary of the inner iris size. For the slit iris type (e.g. iris type 3), this will be the width of the slit.

Hence, it can be seen that certain Column combinations can inference a particular mask or iris configuration. For example, the annular mask can correspond to the outer iris size or diameter of Column 4 and the inner iris size or diameter of Column 5. Similarly, the elliptical mask can correspond to the major axis length of Column 4 and the minor axis length of Column 5. Further, the slit mask can correspond to the slit length of Column 4 and the slit width of Column 5. Accordingly, Columns 2, 4, and 5 can be used to determine characteristics of a mask.

Column 6 is for the slit offset 1012. For both the circular and the annular iris types (e.g. iris types 0 and 2), this will be zero. For the elliptical and the slit iris types (e.g. iris types 1 and 3), this will be the offset of the pulse. According to some embodiments, the elliptical and/or slit pulse shapes can be used to ablate the hyperopia shape.

Column 7 is for the slit angle 1014, which is used for the elliptical and slit iris types (e.g. types 1 and 3). Columns 8 and 9 are for the x- and y-scanning locations, 1016 and 1018, respectively. They can be used for all iris types (e.g. iris types 0, 1, 2, and 3). In a Variable Spot Scanning system, individual pulses can be directed to associated x,y locations. In some cases, Columns 8 and 9 may be used primarily for the circular and annular pulses (e.g. iris types 0 and 2). Column 10 is for the laser repetition rate or inter-pulse delay 1020, and can correspond to the delay that is used between consecutive pulses, which may be measured in mini-seconds. Column 11 is for indicating whether the treatment is wavefront guided 1022.

Figure 10A:
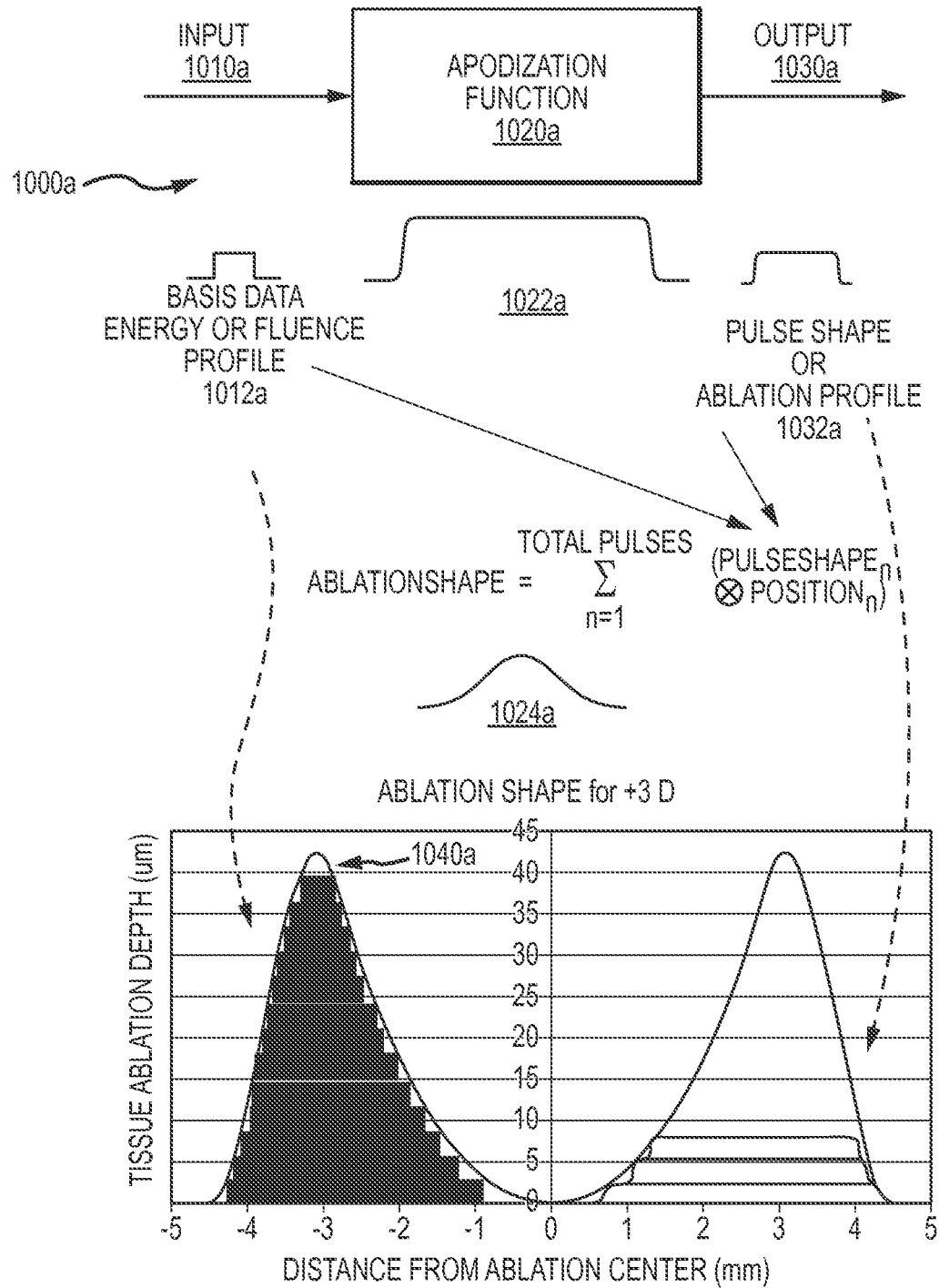
FIGS. 10A and 10B depicts aspects of apodization functions and treatment target ablation shape development, according to embodiments of the present invention.

As shown here, aspects of Columns 2, 4, 5, 8, and/or 9 can be used to determine a crater or pulse shape 1030, which is then used to determine an ablation or target shape 1040 of a treatment. For example, an apodization or adjustment function 1050 can be applied to a pulse basis data profile 1070, to determine the crater or pulse shape 1030. As discussed elsewhere herein, the basis data 1070 can include or correspond to a basis data energy (or fluence) profile, and the pulse shape 1030 can include or correspond to a pulse ablation profile. The adjustment can be performed on individual pulse spots of the treatment, and in some cases can be specific to the particular pulse spot. In some cases, the adjustment function can account for position dependent asymmetry associated with the basis data. For example, an adjustment function may include a weighting function, such that the basis data is modified based on a radial distance from the treatment center, or that is based on a x,y scanning position. Exemplary position dependent asymmetry features are discussed elsewhere herein, relative to FIGS. 9A and 9B, for example. FIG. 10A depicts aspects of an apodization method 1000a according to embodiments of the present invention. As shown here, input data 1010a, which may include or correspond to a pulse basis data profile 1012a, can be processed with an apodization function 1020a. In some cases, the apodization function 1020a can be applied to the pulse data profile 1012a to reflect a smoothing or transition effect. For example, as discussed elsewhere herein, an aperture, mask edge, or some other optical feature of a laser system may produce an energy transition or ablation depth transition on the output 1030a that is not precisely sharp. The input 1010a or pulse basis data profile 1012a can include or correspond to a basis data energy (or fluence) profile, and the output 1030a or pulse shape 1032a can include or correspond to a pulse ablation profile. For example, the energy profile or ablation depth corresponding to a pulse shape 1032a does not exhibit an abrupt change to zero at the edge of the pulse. The apodization function or adjustment 1020a can be applied to the basis data 1012a, so as to account for this smoothing effect. In some cases, an aperture can produce an edge effect, such that the energy distribution corresponding to the aperture edge is not sharp, but rather is smooth. Here, the apodization function 1022a has a smooth edge or transition. In a corresponding manner, the pulse shape 1032a that is based on the basis data profile 1012a and the apodization function 1022a also has a smooth edge or transition. Embodiment of the present invention encompass the implementation of any of a variety of apodization functions. For example, in some cases pulse basis data profiles can be adjusted using an apodization function 1024a having a Gaussian curve, a normal curve, or a bell curve, for example where the laser energy has a Gaussian distribution.

According to some embodiments, pulse shapes such as shape 1032a, rather than pulse basis data profiles such as profile 1012a, can be used to generate a target ablation shape. For example, as shown in the lower panel of FIG. 10A, a target ablation shape 1040a can be generated by combining multiple pulse basis data profiles (e.g. having sharp cut-offs or delta functions at the edge) as shown on the left side of the ablation shape. In comparison, a target ablation shape can be generated by combining multiple apodized pulse shapes as shown on the right side of the ablation shape. Using pulse or crater shapes, however, it is possible to more closely approximate the target ablation shape. Relatedly, the apodized pulse or crater shapes can more closely approximate the actual effect of the ablation, and therefore treatment targets can be generated which take into account such actual effects. Hence, an exemplary method for generating a target ablation shape for use in a refractive treatment for an eye of a patient may include obtaining a basis data profile 1012a, determining a pulse shape 1032a based on the basis data 1012a and an apodization function 1022a, and generating the target ablation shape 1040a based on the pulse shape 1032a. The basis data profile may correspond to any of a variety of iris type shapes, such as a circular shape, an elliptical shape, an annular shape, a slit shape, and the like. According to some embodiments, the input 1010b or matrix 1012b can include or correspond to a basis data energy (or fluence) profile, and the output 1030b or matrix 1032b can include or correspond to a pulse ablation profile.

Any of a variety of factors associated with the laser or optical path of a beam may contribute to apodization of a pulse shape. For example, a lens, an aperture edge, a laser cavity, a laser beam energy, an off-axis beam orientation, or the like, can have an impact on the pulse shape. In some cases, an apodization function can be associated with a single factor, or with a combination of factors. For example, an apodization function can be associated with a lens at the exit pupil of a laser device. Relatedly, an apodization function can be associated with an aperture edge taken in combination with a lens. In some cases, an apodization function can be determined using an empirical approach. In some cases, an apodization function can be determined using a theoretical approach.

Figure 10B:
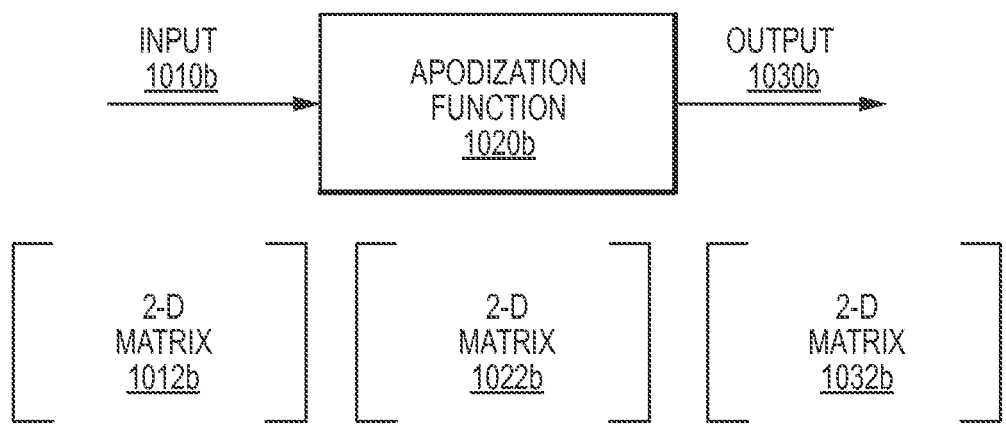

As depicted in FIG. 10B, the input data 1010b, which may include or correspond to a two dimensional matrix 1012b, can be processed with an apodization function 1020b, which itself may include a two dimensional matrix 1022b, so as to provide output data 1030b, which may include or correspond to a two dimensional matrix 1032b. In some cases, the output 1030b can be obtained by processing the input 1010b and the apodization function 1020b with a mathematical operation such as a dot product operation, a matrix multiplication operation, a point by point multiplication, or the like. For example, an input matrix and an apodization function matrix can be multiplied, so as to produce an output matrix. In some cases, for example where the input 1010b is provided as a constant, the output 1030b can be generated as a scaled version of the apodization function 1020b.

In some cases, the apodization or adjustment function can be calculated on the fly, for example to account for situations which may occur during the ablation procedure. For example, where a closed-loop system is used to monitor the ablation progression, and under-ablation or over-ablation is realized, an apodization function may be applied to adjust each of the subsequent basis data to compensate for the deviation. According to some embodiments, the deviation can be represented by or related to the difference between the intended ablation depth or profile (or shape) and the measured ablation depth or profile (or shape). According to some embodiments, the deviation can be represented by or related to the difference between the intended ablation depth or profile (or shape) and the measured ablation depth or profile (or shape) of the summation of pulses laid down up until that time. In some cases, the apodization function can be determined based on the under-ablation, over-ablation, or other deviation. As another example, if a similar monitoring system detects a deviation of the basis data itself, which may be affected by certain environmental factors (e.g. temperature, humidity, and the like), particularly associated with transition of the edge of the mask, a different apodization function may be used. In some instances, it may be desirable to not apply a weighting function to basis data. In some instances, a weighting function can be set to "1" or some other number or value, such that no adjustment or apodization is applied to the basis data. In some instances, it may be desirable to only apply an adjustment where the beam is decentered, and to not apply an adjustment where the beam is centered. In some instances, a decision whether to apply an adjustment can be based on the iris shape. In some instances, a weighting function can depend on the iris shape. In some cases, a weighting function can be provided as a two dimensional matrix.

In some cases, a particular iris type configuration can be achieved using an optical transformation technique, instead of using a mask. For example, an elliptical iris type can be achieved using an optical transform mechanism, such as a tilted cone type object. Such optical transform hardware elements can be used to impart various shapes to the ablation pulse beam.

As depicted in FIG. 10, in some cases the calculation of an ablation shape may account for a cosine effect 1060, such as that which is described in Dai, Wavefront Optics for Vision Correction (SPIE Press Monograph Vol. PM 179; 2008), the content of which is incorporated herein by reference. Related cosine effect features are discussed in U.S. Pat. Nos. 5,219,344 and 7,892,227, and in US Patent Publication No. 2008/0287928. The content of each of these filing is incorporated herein by reference. The cosine effect can be applied as a global function to the ablation target or shape, and is different from a function that is applied to a basis data profile, for example.

Figure 11:
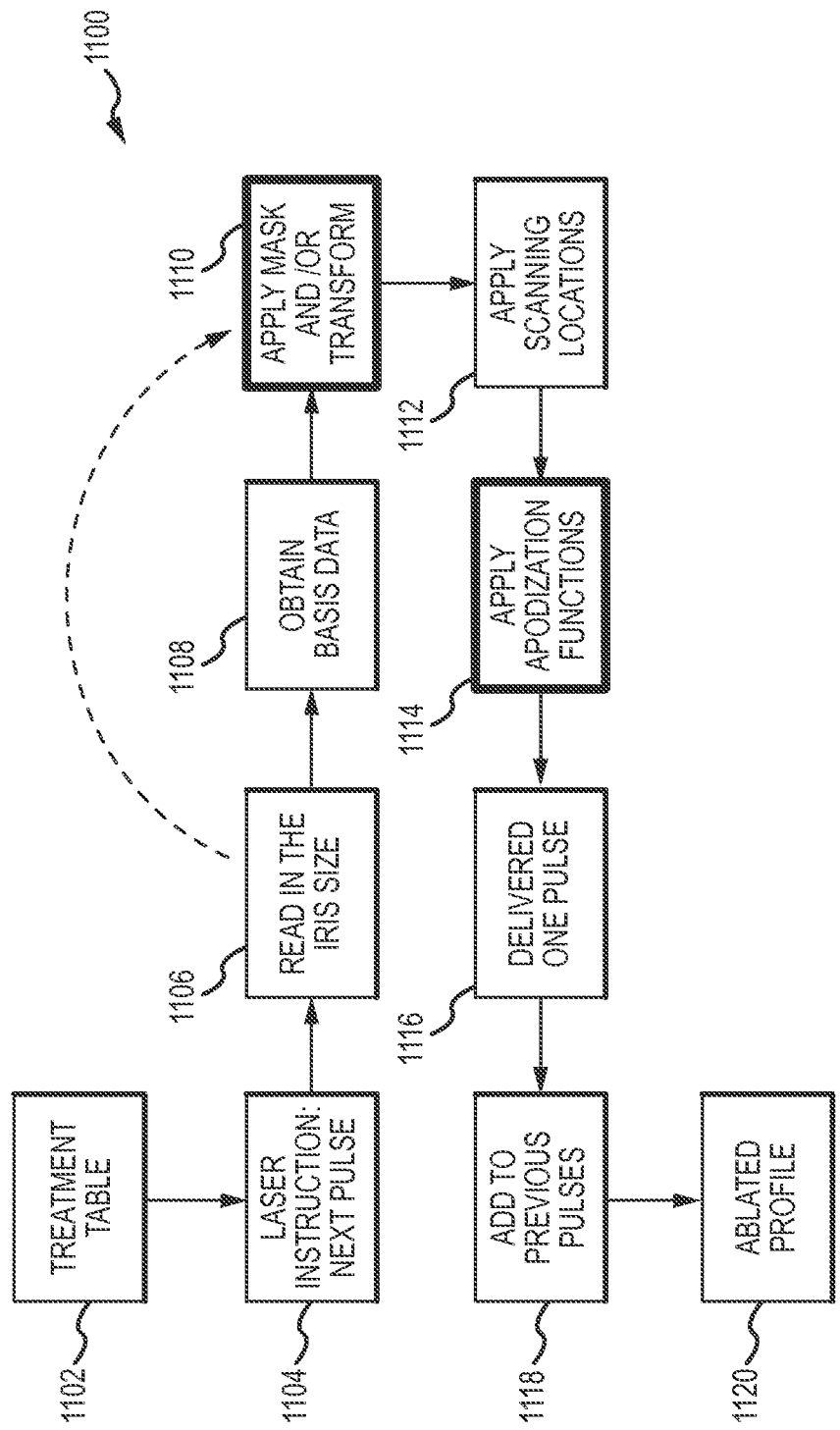
FIG. 11 depicts aspects of treatment table implementation, using apodization functions, according to embodiments of the present invention.

FIG. 11 depicts aspects of an ablation profile generation process 1100, according to embodiments of the present invention. As shown here, the process of assembling a set of laser pulses into a cumulative ablation volume can involve a number of steps. The process can involve a treatment table 1102 (e.g. a file containing lines of information for instructing the laser to perform certain operations) which is read and then executed so as to produce the ablated profile or target shape 1120. For example, the treatment table 1102 can be used to generate a laser pulse instruction 1104. An iris size 1106 can also be incorporated, and a mask 1110 can be applied, optionally based on the iris size 1106 and/or the basis data 1108. In some instances, techniques may involve the use of existing basis data files 1108, which are adjusted to account for mask 1110 and/or x,y positioning factors 1112.

Embodiments of the present invention encompass techniques which account for smoothing or transition effects associated with basis data for particular pulse shape. Similarly, embodiments encompass techniques which account for effects related to decentering or x,y scanning locations 1112 of the pulse beam. To account for such effects, a new basis data architecture is proposed. In some instances, this architecture may be used with existing basis data files without modifying them. As depicted here, the basis data assembly process may include steps such as introducing a mask 1110 to account for different iris shapes, and using an apodization function 1114 to account for position-dependent ablation features. Individual pulses 1116 can be added to previous pulses 1118, so as to provide the ablated profile 1120.

Figure 12A:
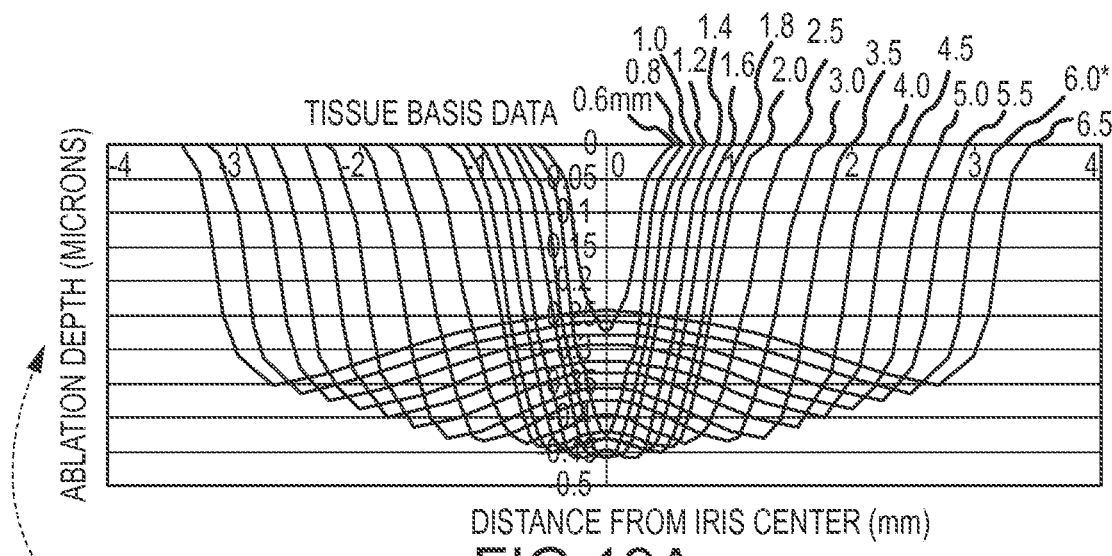
FIGS. 12A, 12B, and 12C depict aspects of basis data characteristics, according to embodiments of the present invention.

FIG. 12A illustrates basis data profiles or cross-sections for circular ablation pulses, according to embodiments of the present invention. This chart shows the relationship between the ablation depth and radial distance from the iris center, for circular shapes created with various iris sizes (e.g. the iris diameter ranges between 0.6 mm and 6.5 mm). In this sense, the x-axis of the graph corresponds to the radial distance from the iris center or optical center. The basis data profile (*) for the ablation pulse corresponding to an iris size of 6.0 mm, for example, presents a deeper peripheral portion (e.g. at about 2.5 mm) and a shallower central portion (e.g. at 0 mm). The size of the iris and/or the pulse can be based on the mask configuration. As depicted here, the ablation depth profile can vary according to the iris size. Relatedly, the ablation depth profile may not change proportionally to changes in the iris size. For example, larger iris sizes can provide ablation depth profiles with deeper peripheries and shallower centers, whereas smaller iris sizes can provide ablation depth profiles with shallower peripheries and deeper centers.

In general terms, basis data can correspond to or be defined by the volumetric profile of material removed for a single laser pulse. There may be different sets of basis data corresponding to different types of material. For example, basis data can correspond to human corneal tissue material. Such basis data can be generated based on ablation studies using human eyes, including clinical trials and the like. As discussed elsewhere herein, a pulse ablation profile can be determined based on a basis data energy (or fluence) profile and an apodization function. In some cases, a measured pulse ablation profile obtained from a treated tissue reflects the effects of apodization. In this sense, the measured pulse ablation profile data can be considered to account for or incorporate certain apodization effects, such as off-axis orientation, lens effects, aperture edge effects, and the like.

Figure 12B:
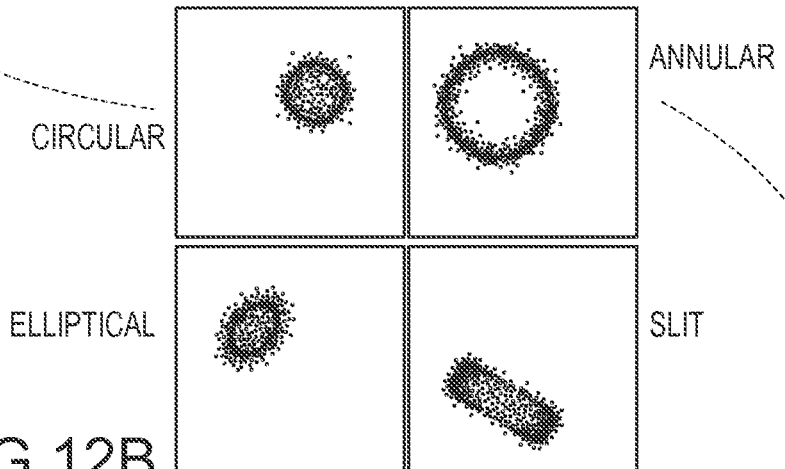

As depicted in FIG. 12A, the basis data profile (*) for the ablation pulse corresponding to an iris size of 6.0 mm has a diameter that is slightly larger than 6.0 mm. This difference can represent a smoothing effect, which is also shown in FIG. 12B. Hence, when there is a mask edge (e.g. such as the inner mask edge shown in FIG. 5B), the energy transition or ablation depth transition associated with the mask edge is not exactly sharp. That is, there is some transition, and the ablation depth does not immediately go to zero at the edge. Hence, an apodization function or adjustment can be applied to the basis data, so as to account for this smoothing effect. This approach is different from some currently used techniques, where it is assumed there is a sharp edge for basis data. Relatedly, diffraction and/or refraction effects may contribute to the smoothing. Similarly, biological effects or tissue response (e.g. heat transfer or associated breakage of chemical bonds in the collagen molecules of the corneal stroma) may contribute to the smoothing or transition effect depicted here. In some instances, smoothing or transition effects may be the result of semi-coherency in the laser beam.

In the basis data profiles shown in FIG. 12A, it can be seen the ablation depth varies across the entire ablation pulse, and when going from the center to the peripheral edge of the ablation pulse. As noted elsewhere herein, this ablation depth profile may be skewed for off-center pulse beams.

FIG. 12B provides representations of basis data for a circular pulse shape (top left panel), an annular pulse shape (top right panel), an elliptical pulse shape (bottom left panel), and a slit pulse shape (bottom right panel). The area of these panels is 10 mm×10 mm. Each of these representations corresponds to a different iris shape or type, and provides an indication of the energy distribution of a single pulse. The circular pulse shape in the top left panel can correspond to an iris diameter of about 4 mm, for example. Similarly, the annular pulse shape in the top right left panel can correspond to an outer iris diameter of about 6.5 mm and an inner iris diameter of about 4 mm, for example. As shown here, there is a smoothing or transition effect associated with the inner and outer boundaries of the annular iris shape, similar to the smoothing/transition effect described above for the circular iris shape. The smoothing or transition effects are also seen at the outer boundaries of the elliptical and slit iris shapes.

Figure 12C:
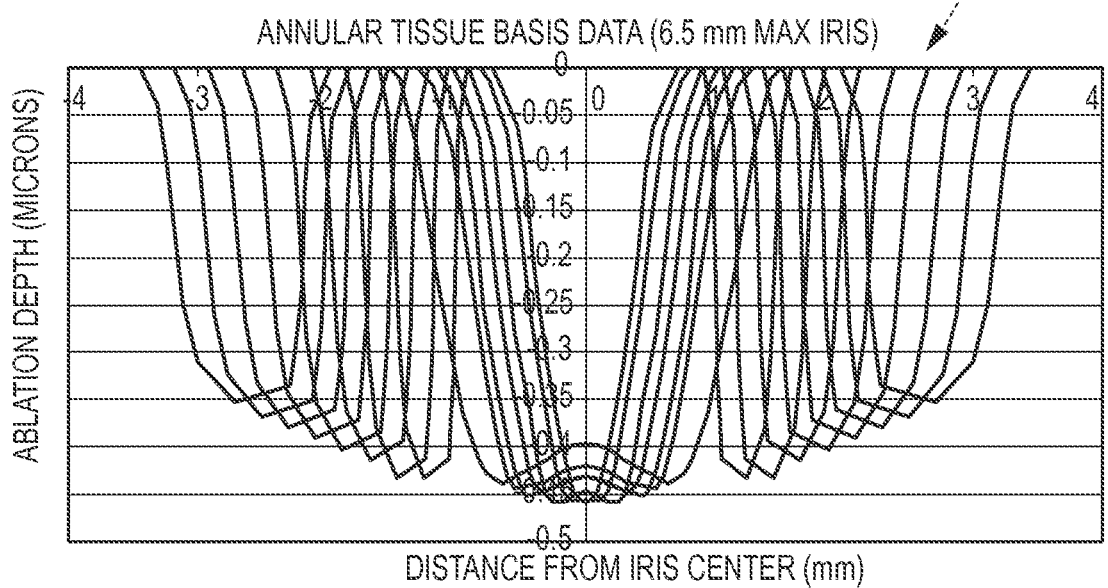

FIG. 12C illustrates basis data profiles or cross-sections for annular ablation pulses, according to embodiments of the present invention. Here, a block may be used to create an annular shape by obscuring a central part of the pulse, for example as described in US Patent Publication No. 2012/0083776, which is incorporated herein by reference. Again, as depicted here, there may be a smoothing or transition at the inner and outer boundaries of the annular ring ablation.

With regard to the smoothing or transition effects depicted in FIGS. 12A to 12C, embodiments of the present invention encompass apodization or adjustment functions which account for this feature. Because the smoothing may be a result of a mask and/or block, apodization functions may in part be based on such mechanisms. In some instances, such smoothing or transition effects can be addressed using cubic spline techniques.

FIG. 13A provides representations of basis data for a circular pulse shape (top left panel), an annular pulse shape (top right panel), an elliptical pulse shape (bottom left panel), and a slit pulse shape (bottom right panel). The area of these panels is 10 mm×10 mm. Each of these representations can correspond to the energy distribution of a collection of multiple pulses. Thus, for example, the top left panel represents the accumulation of several circular pulse beam pulses, directed at various x,y locations. Similarly, the top right panel represents the accumulation of several annular pulse beam pulses, directed at various x,y locations. As shown here, the different size pulses were provided using the same iris type. For example, the size of the circular pulses in top left panel vary throughout a range. FIG. 13B provides a representation of accumulated basis data for multiple ablation pulses of various shapes. Here, a combination of differently sized circular, annular, and elliptical pulses were used. The area of this panel is 10 mm×10 mm. As depicted here, unique and irregular ablation shapes can be achieved by combining various pulse shapes.

Figure 13C:
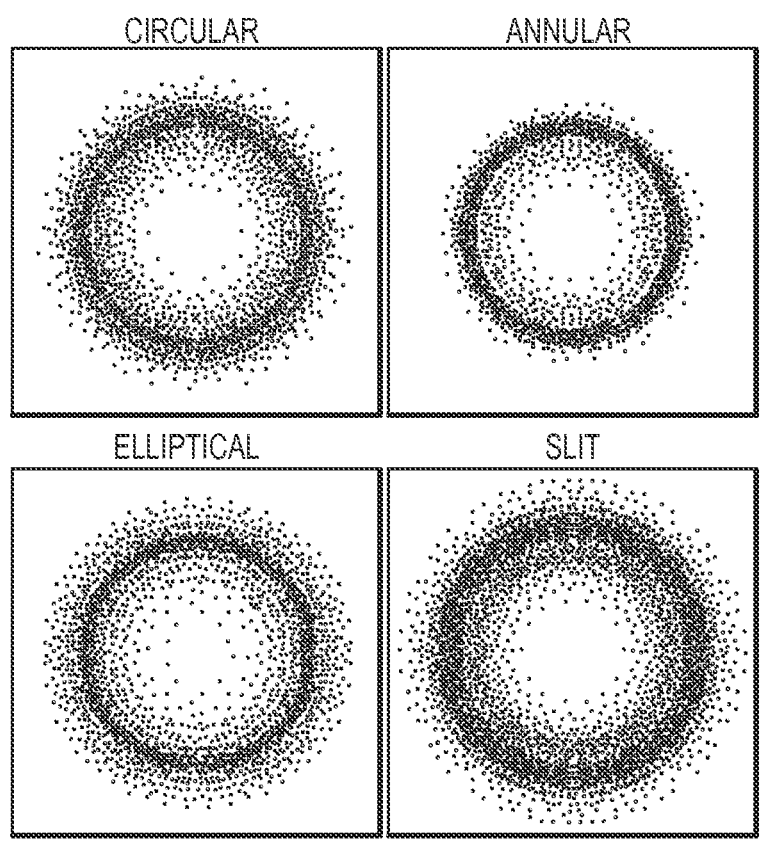
Figure 13D:
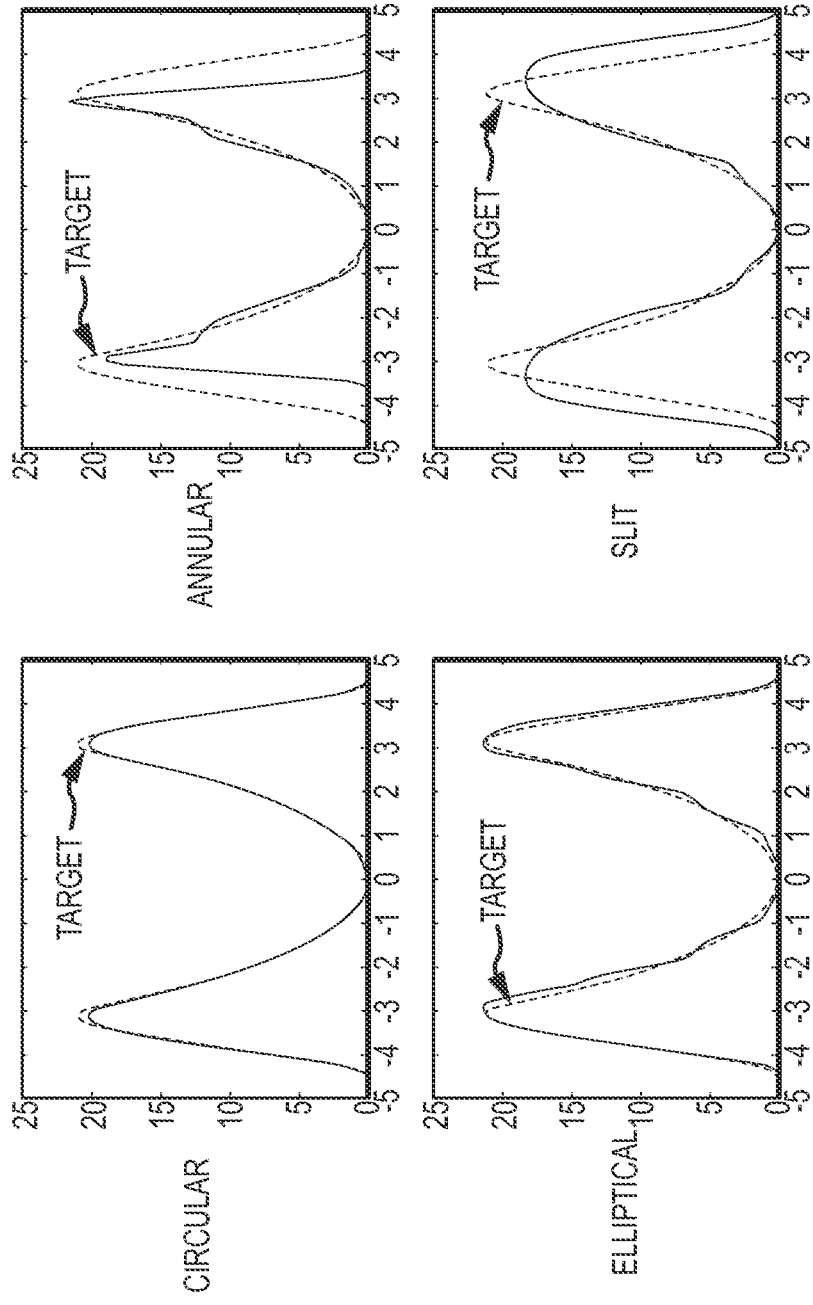

FIG. 13C provides representations of basis data for a circular pulse shape (top left panel), an annular pulse shape (top right panel), an elliptical pulse shape (bottom left panel), and a slit pulse shape (bottom right panel). The area of the individual panels is 10 mm×10 mm. Each of these representations can correspond to the energy distribution of a collection of multiple pulses. As shown here, the ablation maps can be used for fitting a 1.5 D hyperopic target with circular, annular, elliptical, and slit shapes, and thus can correspond to a simulation of a +1.5 D ablation. FIGS. 13D and 13E show aspects of fitting quality with a target hyperopia shape. As illustrated here, the different pulse shapes can be used to achieve an ablation having a good fit with a target hyperopia shape.

For example, a least square fitting approach can be used to analyze the data. In some cases, it is possible to obtain a target and a simulated target, and compare the two targets with a minimum root mean square error approach, to evaluate a good fit. In some cases, simulated annealing techniques such as those described in PCT Application No. PCT/US01/08337 (incorporated herein by reference) can be used.

Figure 13F:
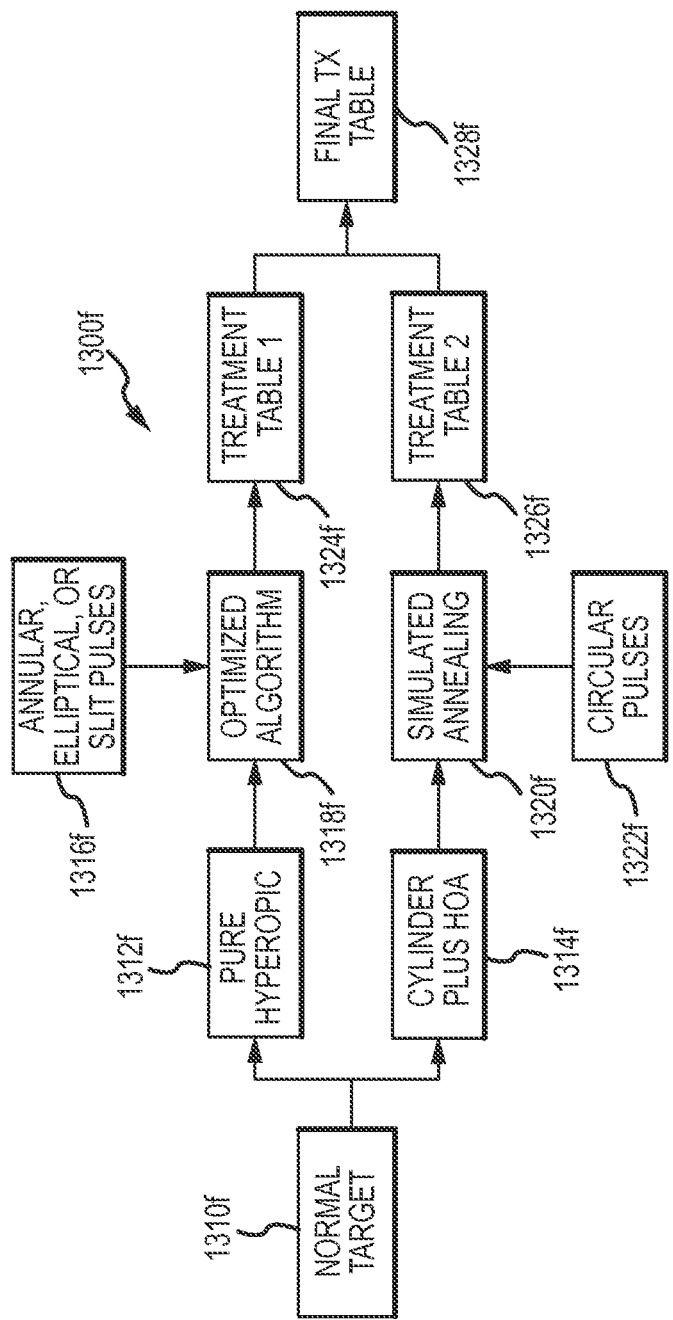

Results such as those obtained in FIGS. 13C to 13E can be achieved using a treatment table generation approach such as that described in FIG. 13F. As shown here, different aspects of the normal target can be separated into various modules for segmented treatment table development. For example, the original target or normal target 1310$f$ can be separated into two pieces, namely a hyperopic component 1312$f$, and a component 1314$f$ for cylinder and high order aberrations (HOA). The upper arm of the flow chart represents a process for generating Treatment Table 1324$f$, and the lower arm of the flow chart represents a process for generating Treatment Table 2 1326$f$. In the lower arm, a simulated annealing process 1320$f$, for example SALSA as discussed elsewhere herein, can be used for circular pulses 1322$f$ to generate Treatment Table 2 1326$f$ for addressing the cylinder and HOA component 1314$f$. In the upper arm, an optimized algorithm 1318$f$, such as maximum entropy, can be used for annular pulse shapes, elliptical pulse shapes, or slit pulse shapes 1316$f$ (e.g. corresponding to other basis data configurations) to generate Treatment Table 1 1324$f$.

Tables 1 and 2 can be combined to provide a final Treatment Table 1328$f$. With circular pulses 1322$f$, there can be three free parameters per pulse (e.g. iris size, x scanning location, and y scanning location). To determine one circular pulse involves identifying the size of the pulse, and the location of the pulse. For other pulse shapes 1316$f$ (e.g. annular, slit, and elliptical) such as those shown in FIGS. 4B to 4D, there can be four free parameters per pulse. Moreover, the basis data for the other shapes (e.g. annular, slit, and elliptical) may not be circularly symmetrical in the same way in which a circular pulse shape can be circularly symmetrical. When using the annular, elliptical, slit, or other pulse shapes, it is possible to proceed with an analytical approach, as compared with a numerical approach, when processing the hyperopic component, so as to obtain the corresponding hyperopic treatment table. Hence, the treatment table generation process 1300$f$ of FIG. 13F can employ an algorithm that is specific for annular, elliptical, or slit pulses for hyperopic treatment. Pure hyperopic ablation shape, such as for +1 D, +2.35 D, and the like, can be well defined, and algorithms other than simulated annealing can be used to derive an optimized or desired pulse sequence. In some cases, a least squares fitting may be used.

Figure 13G:
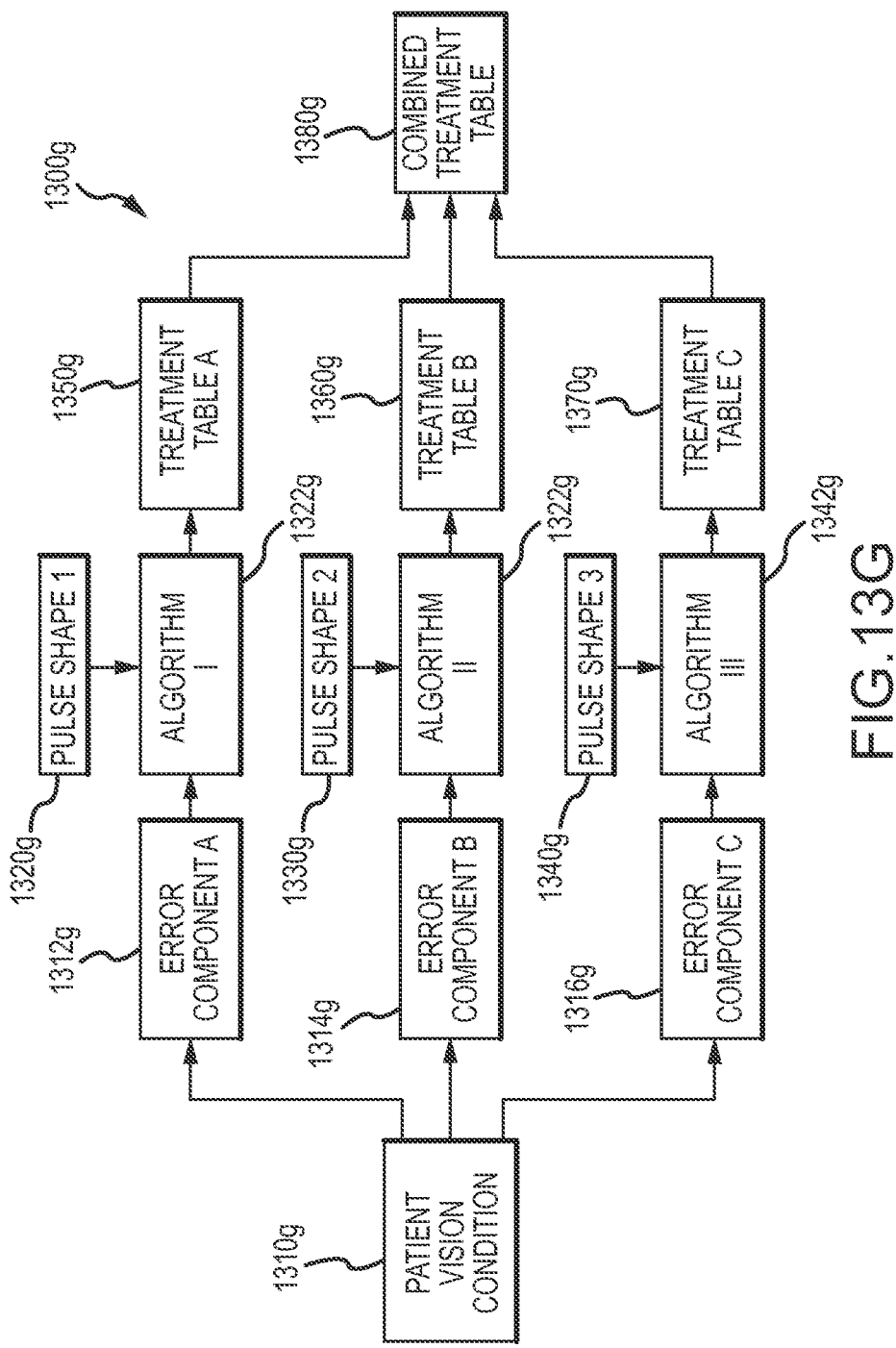

FIG. 13G depicts aspects of a treatment table generation process 1300$g$ according to embodiments of the present invention. As shown here, an original target or patient vision condition 1310$g$ can encompass one or more error components, for example such as pure hyperopia (e.g. sphere), cylinder, high order aberrations, or other refractive error modalities. The vision condition can be separated into individual error components, such as error component A 1312$g$, error component B 1314$g$, and error component C 1316$g$. Further, certain algorithms can be used to process those error components in association with certain pulse shapes, so as to obtain individual treatment tables. For example, algorithm I 1322$g$ can be used to process error component A 1312$g$ in association with pulse shape 1 1320$g$, so as to obtain treatment table A 1350$g$. Similarly, algorithm II 1332$g$ can be used to process error component B 1314$g$ in association with pulse shape 2 1330$g$, so as to obtain treatment table B 1360$g$. Relatedly, algorithm III 1342$g$ can be used to process error component C 1316$g$ in association with pulse shape 3 1340$g$, so as to obtain treatment table C 1370$g$. Any of a variety of algorithms or optimization techniques can be used to obtain the individual treatment tables. For example, some approaches may include least squares, maximum entropy, and the like. In this way, different algorithms can be used for different basis data configurations or pulse shapes. What is more, any of a variety of techniques can be used to combine treatment tables. As shown here, Tables A, B, and C can be combined to provide a final combined Treatment Table 1380$g$. In some cases, one individual treatment table can be appended to another treatment table. Hence, for example, a treatment table having 300 pulses can be appended to a treatment table having 500 pulses, so that the combined treatment table allows the system to effect the 500 pulses of the first table followed by the 300 pulses of the second table. In some instances, pulses of the individual tables can be sequenced according to certain rules or decision factors, such that there is an interweaving or specific ordering of the pulse sequences.

As with the representations shown in FIGS. 12A to 12C, the basis data represented in FIGS. 13A to 13C also indicates a smoothing or transition effect at the pulse peripheries.

It can be seen in FIG. 13A that the application of multiple annular pulses (top right panel) is well suited for use with a hyperopia treatment, although the central obscuration block may have an impact on efficiency. Similarly, the multiple ellipse pulses (bottom left panel) are well suited for use with a hyperopia treatment. The intermittent darker areas (resembling watermelon seeds) indicate portions of greater ablation depth. Hence, it may be desirable to supplement such a treatment with the application of smaller pulses to fill in the areas between and around the darker areas, so as to produce a more uniform ablation shape. The accumulation of multiple slit pulses (bottom right panel) may also be useful for a hyperopia treatment, although again, it may be desirable to supplement such a treatment with the application of smaller pulses to fill in the areas between and around the darker areas, so as to produce a more uniform ablation shape. A treatment involving the accumulation of multiple pulses of different shapes (e.g. using different iris types), such as that shown in FIG. 13B, may similarly be useful for a hyperopia treatment.

Embodiments of the present invention further encompass techniques that involve the application of a first pulse regimen (e.g. using a first mask shape) in combination with a second pulse regimen (e.g. using a second mask shape) so as to produce an ablation shape. In this way, it is possible to achieve a result such as that depicted in FIG. 13B. Such pulse regimens can be applied during the course of a treatment, in any desired sequence. In some instances, individual pulses or sets of pulses can be presorted in advance of a treatment procedure.

According to preliminary studies, by using various iris types, it may be possible to provide hyperopic ablation treatments that can be performed more quickly, while at the same time keeping the ablation smooth. In some instances, the smoothness can be evaluated based on a root mean square analysis (e.g. low RMS), or on a peak to valley analysis (e.g. low PV error). For example, annular, elliptical, or slit shapes can be used to decrease the amount of time involved for performing a hyperopia treatment.

As illustrated by FIGS. 12A to 13C, the implementation of annular, elliptical, and/or slit iris types can provide different ablation pulse shapes, and relatedly can be useful for generating hyperopic ablation treatment shapes. The basis data, which can refer to a single pulse ablation profile, can be used with a treatment solution engine to develop the treatment shape. In some cases, the treatment shape can be generated based on a simulated annealing least squares algorithm (SALSA).

The treatment table and basis data embodiments disclosed herein are well suited for use in a variety of vision correction modalities, including the STAR S4 IR™ Excimer Laser System with VSS Refractive™ technology (Variable Spot Scanning). In some cases, embodiments may encompass the use of existing single-spot energy profiles, or basis data, which are adjusted based on factors such as iris type and/or x,y scanning location. For example, shape-related masks can be used to redefine the boundary of the revised energy profile. Similarly, apodization functions can be used to reflect the smooth transition of the boundaries to account for practical implementation. When using the root mean squares (RMS) error, peak-to-valley (PV) error, and the ablation time as comparison metrics, it has been observed that an elliptical iris type can provide a highly accurate and efficient ablation shape for hyperopic and mixed astigmatic ablations. Use of noncircular ablation pulses can speed up a hyperopic treatment without a loss of fitting accuracy of the target shape.

Determination of Treatment Shape

In some embodiments, systems and methods may involve producing a treatment shape in a variety of steps. For example, an optical region shape can be determined, either by Munnerlyn equations or wavefront techniques. In some cases, aspects of the shape can be smoothed by pixel averaging, or by spatial averaging of depth.

Once the desired ablation shape has been determined, a next step is to define the parameters of the actual laser ablation required to administer the treatment ablation profile. A particularly useful way of determining these parameters is by using an ablation equation, such as the one shown below.

$$AblationShape = \sum_{n=1}^{TotalPulses} (PulseShape_n \otimes Position_n)$$

In brief, this equation is based on the principle that a treatment ablation is the sum of each of the individual laser pulses. This equation has been empirically verified on a variety of materials including plastic, and bovine, porcine, and human corneal tissue.

In this equation, the AblationShape variable represents the desired ablation shape. In this sense, it is a known variable. The target shape can be, for example, a simple sphere, an ellipse, a cylinder for treating myopia or hyperopia, or even a saddle for treating mixed astigmatism. The target shape can be any arbitrary shape, such as the map from a wavefront type device or any other topography system.

Figure 14:
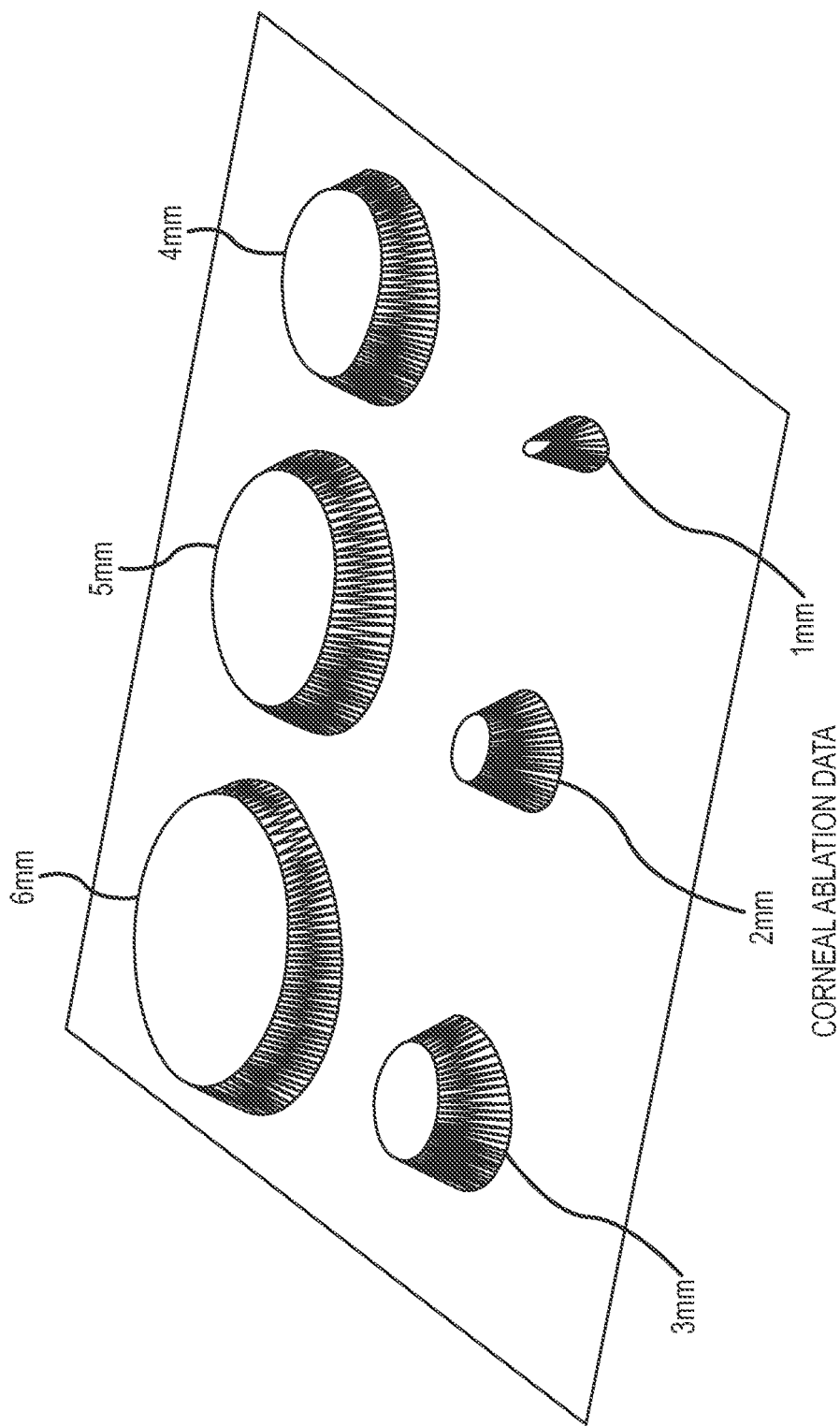
FIG. 14 depicts aspects of crater shapes corresponding to single laser pulses, according to embodiments of the present invention.

The PulseShape variable, which is also a known variable, represents the ablation shape of each laser pulse size to be used. The PulseShape typically varies for different ablated materials, such as plastic, animal cornea, or human cornea. The PulseShape also typically varies for each laser pulse diameter. Certain PulseShape features are described herein at FIG. 10. An example of this type of ablation data is also shown in FIG. 14. This figure shows different shapes of craters expected from a single laser pulse. There is a unique description for every unique pulse shape or size to be used. By systematically measuring the shape which each laser pulse ablates onto a specific target material, it is possible to generate such basis data for a variety of materials, such as tissue or plastic. For a given material, at a given diameter, the shape is generally consistent from laser system to laser system.

A fixed spot laser may have only one description, while a variable spot laser could have as many as desired. There is no requirement that the crater shape be flat, round, or symmetric. As long as it can be described mathematically or with an array of data, it can be incorporated in the equation.

In order to create the ablated surface, it is useful to determine the locations where each of the laser pulses will be applied. The Position variable, which represents the exact position of every laser pulse, is an unknown variable. Certain Position features are described herein at FIG. 10. The Position variable can be calculated by solving the ablation equation. Put another way, the output is a set of instructions for creating the target ablation shape using the laser pulses. This is sometimes called a treatment table. The treatment table consists of a list of individual pulses, each containing the size and offset, or position, to be used for that pulse. When the laser fires according to the instructions in the treatment table, the target shape will be created.

The target ablation shape is a theoretical construct; it is a mathematically perfect representation of a desired ablation outcome. Put another way, while the application of thousands of specifically placed brief laser pulses can create an actual ablation shape that approaches the ideal target ablation shape, in the end it is still an approximation thereof.

Therefore, solving for the Position variable can allow for the formulation of a corresponding ablation shape that approaches the target ablation shape as closely as possible. In this way each of the thousands of pulse positions are individually determined so as to minimize the difference between the ideal target ablation shape and the actual resulting ablation shape. In a system for ablating tissue using a scanning laser, a presently preferred computational technique for achieving this goal employs simulated annealing.

Other mathematical approaches include, for example, the SALSA Algorithm. SALSA is an acronym for Simulated Annealing Least Squares Algorithm. It is an algorithm that solves an equation having over 10,000 unknowns. The algorithm finds the best solution by selecting: the number of pulses, the size of each pulse, and the location of each pulse. It is an exact algorithm, and makes no statistical assumptions.

Simulated Annealing is a recent, proven method to solve otherwise intractable problems, and may be used to solve the ablation equation discussed above. This is more fully described in PCT Application No. PCT/US01/08337, filed Mar. 14, 2001, the entire disclose of which is incorporated herein by reference. See also W. H. Press et al., "Numerical Recipes in C" $2^{nd}$ Ed., Cambridge University Press, pp. 444-455 (1992). This approach is also further discussed in co-pending U.S. patent application Ser. No. 09/805,737, the entire disclosure of which is incorporated herein by reference.

Simulated annealing is a method used for minimizing (or maximizing) the parameters of a function. It is particularly suited to problems with very large, poorly behaved function spaces. Simulated annealing can be applied in the same way regardless of how many dimensions are present in the search space. It can be used to optimize any conditions that can be expressed numerically, and it does not require a derivative. It can also provide an accurate overall minimum despite local minima in the search space, for example.

As discussed elsewhere herein, for certain broad-beam lasers, the ablation time for hyperopia may be much longer than myopia due to the use of relatively smaller spots. In some cases, lengthy ablation procedures may result in corneal dehydration, and consequently, the clinical outcome may become sub-optimal. It has been observed that the US population consists of 35% hyperopic people, and 15% are hyperopic among laser treatment patients. It has been discovered that certain non-circular ablation pulse shapes (e.g. annular, elliptical, and slit) can be used to speed up laser treatment time for hyperopia.

Basis Data Adjustment

According to some embodiments, the development of basis data can be based on pre-operative and post-operative wavefront data obtained from an individual, optionally in combination with topography data obtained from the individual. For example, by using a low-pass filter or healing kernel, it is possible to predict the shape of the ablated corneal surface as it would be present immediately following the laser delivery. Embodiments of the present invention encompass techniques for determining a refinement for each of the pulse profiles in the basis data, based on a clinically treated eye, or alternatively based on a number of clinically treated eyes.

Figure 15:
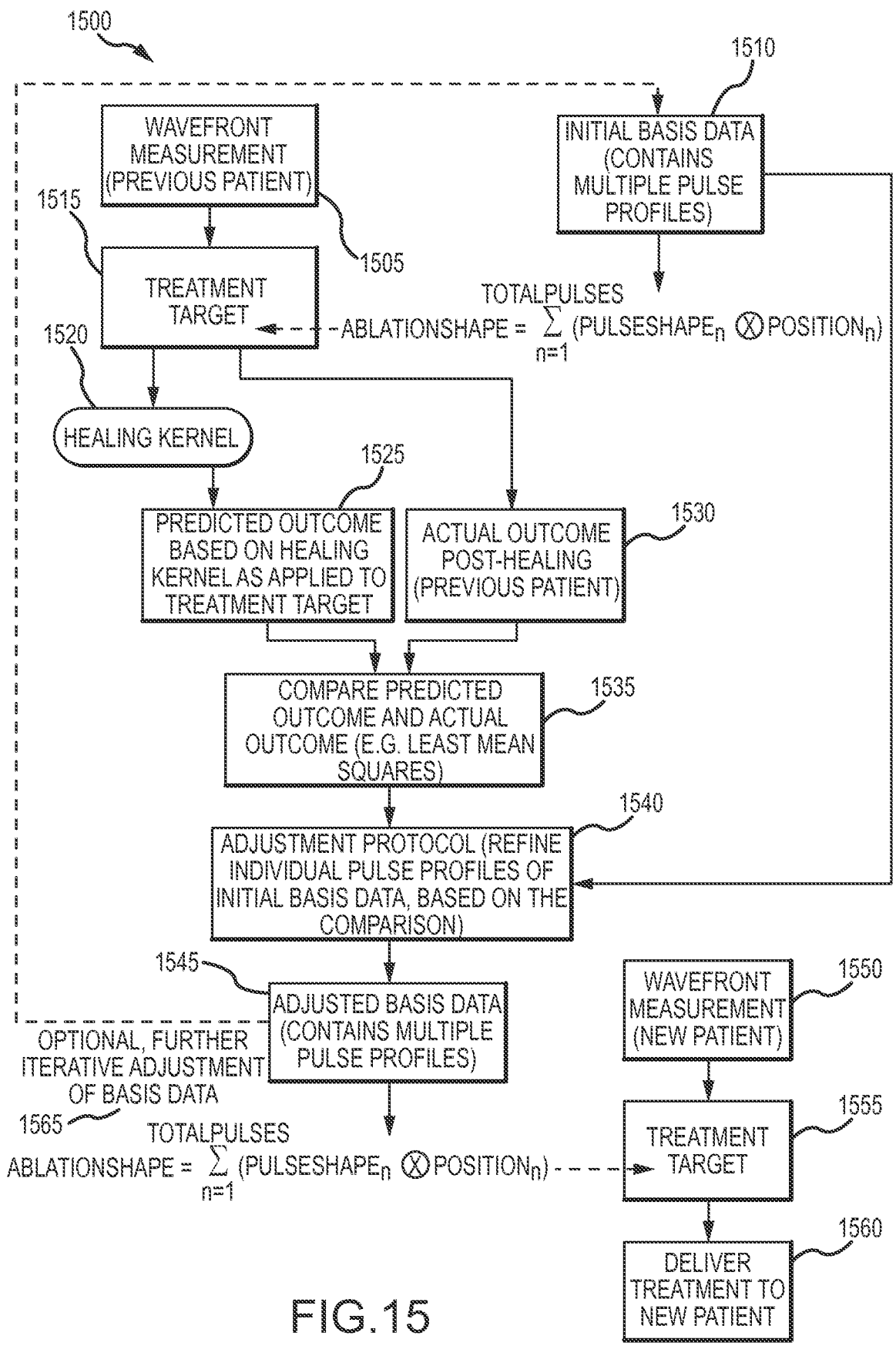
FIG. 15 depicts aspects of a basis data adjustment or development technique according to embodiments of the present invention.

FIG. 15 illustrates aspects of a laser basis data adjustment method 1500 according to embodiments of the present invention. As shown here, a treatment target 1515 for a patient can be determined based on a pre-operative wavefront measurement 1505 of the patient and an initial set of laser basis data 1510. In some cases, pre-operative measurement 1505 can be based on a wavefront measurement of the patient, a topography measurement of the patient, or both. In some cases, a topographic measurement can be converted to a wavefront representation. For example, suppose W(x,y) stands for the wavefront aberration (optical path difference, or OPD) of the entire eye and t(x,y) stands for the topographic height (tissue depth) of the same eye. Given n as the index of refraction for keratometry, it is possible to convert the topographic map into a wavefront map as T(x,y)=t(x,y)/(n−1). Now that both W(x,y) and T(x,y) are expressed in OPD, they can be combined with respect of the target surface S(x,y) as S(x,y)=(1−eta)*W(x,y)+eta*T(x,Y) where eta is a weighting function for topographic map. For example, if eta=1, it is possible to use a straight wavefront map. If eta=1, it is possible to use a straight topographic map. If eta is between 0 and 1, it is possible to use both of them. In some cases, it is possible to combine wavefront and topographic information as discussed in U.S. Pat. No. 8,585,687, the content of which is incorporated herein by reference. An actual post-healing outcome 1530 of a patient treated with the target 1515 can be acquired following the treatment. For example, the actual outcome 1530 can be acquired at about six months post-surgery. In this way, it is possible to obtaining an actual post-healing outcome 1530 of a patient treated with a treatment target ablation shape 1515, wherein the treatment target ablation shape is based on an initial set of laser basis data 1510 and a wavefront measurement 1505 obtained from the patient prior to treatment. As shown here, embodiments of the present invention encompass techniques for processing the treatment target 1515 with a healing kernel 1520, so as to determine a predicted outcome 1525. In some instances, treatment target 1515 is present as a wavefront representation when the healing kernel 1520 is applied. As noted above, topographic information can be converted to a wavefront representation. Aspects of exemplary healing kernel techniques, which may also be referred to as filters, are described in previously incorporated U.S. Patent Application Nos. 61/708,815 and 61/734,030 filed Oct. 2, 2012 and Dec. 6, 2012, respectively, and U.S. patent application Ser. Nos. 14/044,650 and 14/097,841 filed Oct. 2, 2013 and Dec. 5, 2013, respectively.

For example, a healing process or low pass filter process (or an optimized linear filter process) can be used to account for tissue changes following surgery, which may affect both high order and low order aberrations. Exemplary treatment target adjustment processes, which can account for healing effects, can involve deconvolution techniques, as discussed elsewhere herein. A healing process can be considered to be a convolution process. A deconvolution process is a reverse operation, which can be performed to undo the convolution, or reverse the healing effect. In addition to providing treatment plans or adjustments for obtaining post operative healed refractions that match with desired refractions, embodiments of the present invention also encompass techniques for lowering SA for both high and low order aberrations. According to some embodiments, an optimized linear filter can include low pass filtering, and/or filtering that is not low pass. For example, there can be other spatial frequency information that is not low pass.

Post-Operative Epithelial Smoothing and Spherical Aberration

As noted above, cornea remodeling following treatment with a refractive target shape can induce SA, for example due to smoothing of epithelium at the anterior surface of the eye. To develop techniques that compensate for such remodeling, it is helpful to simulate the post-operative epithelium smoothing process with a model. An exemplary healing kernel or filter technique may define the shape of a post-operative cornea surface as a convolution of an ablation target profile with a low-pass filter (LPF), as follows:

$$h_{post-op} = h_{pre-op} - K \otimes T \qquad \text{Equation 1}$$

where T is the ablation target profile. K=K(x,y) is the LPF kernel, which has the following Fourier transform:

$$K(k_x, k_y) = \frac{1}{1 + \sigma^2(k_x^2 + k_y^2)} \qquad \text{Equation 2}$$

K(x,y), the LPF kernel, can be considered as a spatial domain representation. The Fourier transform of K(x,y) (i.e. $K(k_x, k_y)$ or F[K]), can be considered as a frequency or Fourier domain representation.

According to some embodiments, the Fourier transform F[K], or $K(k_x, k_y)$, may be a squared Butterworth low-pass filter of the first order, which can be applied to the treatment target T in order to obtain the wavefront change due to corneal smoothing. In some instances, the Fourier transform of the LPF kernel can be defined by or based on a single diffusion coefficient σ, which has a unit of length.

In some cases, the post-operative epithelium smoothing process can be simulated by defining the shape of the post-operative cornea surface as a convolution of the ablation target profile with a low-pass filter (LPF) as follows (spatial domain):

$$h_{post-op} = h_{pre-op} - K(x,y) \otimes T(x,y) \qquad \text{Equation 3}$$

where h stands for the elevation maps, ⊗ denotes a convolution, T(x, y) is the ablation target profile and K(x, y) is a low pass filter (LPF) kernel, which has the following Fourier transform:

$$K(k_x, k_y) = \frac{1}{1 + \frac{\sigma^2(k_x^2 + k_y^2)}{(0.5 \, dL)^2}} \qquad \text{Equation 4}$$

Equation 4, which is in the Fourier domain, represents a squared Butterworth low-pass filter of the first order, which can be applied to the treatment target in order to obtain the wavefront change due to the corneal smoothing. It can be defined by a single diffusion coefficient σ, which has a unit of length. For some discrete case embodiments, the 101×101 mesh size can be dL=0.1 mm. Based on optimizations using data from certain clinical trials, a sigma of 0.35 mm was determined to best explain that observed data.

According to some embodiments, K(x, y) is in the spatial domain, and is a Fourier transform of $K(k_x, k_y)$. Here, $k_x$ and $k_y$ are Fourier domain or frequency domain variables. According to some embodiments, K(x, y) is an LPF kernel that can be exemplified by a 101×101 matrix or by a 3-D surface expressed in matrix form where x and y are spatial domain variables.

Accordingly, it is possible to obtain a predicted post-healing outcome 1525, where the predicted post-healing outcome 1525 is based on the treatment target ablation shape 1515 and a healing kernel 1520.

Exemplary methods also include comparing the predicted outcome 1525 and the actual outcome 1530 as shown in step 1535, for example by using a least mean squares approach. For instance, a comparison between the actual outcome and the predicted outcome can be performed with least squares fitting (LSF) or least mean squares (LMS) method. In some cases, the comparison can be performed based on both the wavefront data and the topographic data. In some cases, comparison of the wavefront data to topographic data can be performed using an adequate scaling adjustment for the refractive index. For example, the predicted post-operative wavefront can be compared to the actual topographic data, when the topographic data is converted to wavefront maps in optical path difference (OPD). Methods may also include generating an adjusted set of laser basis data as indicated by adjustment protocol 1540, where the adjusted set of laser basis data is based on the initial set of laser basis data 1510 and the comparison 1535 between the actual post-healing outcome and the predicted post-healing outcome. The adjusted set of laser basis data can be used in refractive ophthalmologic ablation surgery. For example, as shown here, a wavefront measurement 1550 for a patient can be obtained, and a treatment target 1555 for the patient can be determined based on the adjusted basis data 1545 and the wavefront measurement 1550. In some cases, pre-operative measurement 1550 can be based on a wavefront measurement of the patient, a topography measurement of the patient, or both. Exemplary techniques for converting topographic information to wavefront representations or for combining wavefront and topographic information are discussed elsewhere herein. The treatment target can then be delivered to the patient as shown in treatment step 1560.

According to some embodiments, laser basis data can be characterized for particular lasers or operating conditions, by taking into account localized environmental variables such as temperature, humidity, airflow, and aspiration. Adjustment of a laser basis data may involve changing the cross-section or side view of a laser profile or pulse. In some instances, the terms "tissue basis" or "basis" and "cross-section" may be used interchangeably. Use of a general basis data framework can allows the implementation of any of a variety of ablation profiles, such as circular ablation profiles, annular ablation profiles, and the like. Embodiments of the present invention encompass various approaches for revising or generating basis data. In some cases, simulations and other techniques can be used to determine desirable annular ratios as well as the separation of annular and circular pulse sizes. Bench work can be performed using calibration plastics for various annular shapes, for example with laser systems as disclosed herein. Verification work can be done with eye ablation for verification. Shapes may be revised based on a controlled clinical study with 10 to 20 eyes, for example. Basis data files and algorithms can be revised or developed to include spots having various shapes.

Figure 16:
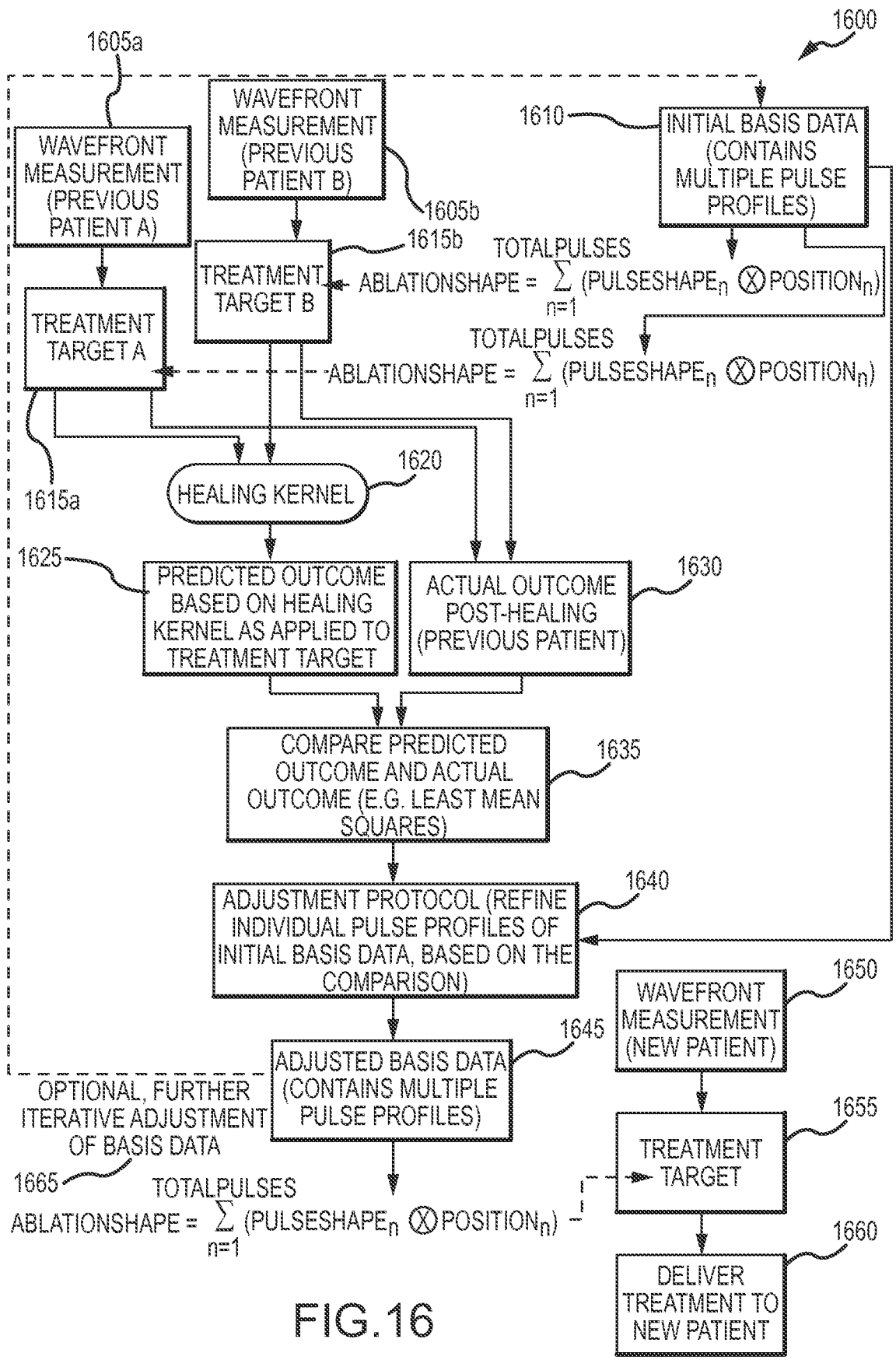
FIG. 16 depicts aspects of a basis data adjustment or development technique according to embodiments of the present invention.

FIG. 16 illustrates aspects of a laser basis data adjustment method 1600 according to embodiments of the present invention. As shown here, a treatment target 1615a for a patient A can be determined based on a pre-operative wavefront measurement 1605a of the patient A and an initial set of laser basis data 1610. Similarly, a treatment target 1615b for a patient B can be determined based on a pre-operative wavefront measurement 1605b of the patient B and the initial set of laser basis data 1610. In some cases, a pre-operative measurement 1605a, 1605b can be based on a wavefront measurement of the patient, a topography measurement of the patient, or both. Exemplary techniques for converting topographic information to wavefront representations or for combining wavefront and topographic information are discussed elsewhere herein. For each of the treatment targets 1615a, 1615b, an actual post-healing outcome 1630 of the patient treated with the target (e.g. patient A treated with target A, or patient B treated with target B) be acquired following the treatment. In this way, it is possible to obtaining an actual post-healing outcome 1630 of a patient treated with a treatment target ablation shape, wherein the treatment target ablation shape is based on an initial set of laser basis data and a wavefront measurement obtained from the patient prior to treatment.

As shown here, embodiments of the present invention encompass techniques for processing a treatment target (e.g. 1615a or 1615b) with a healing kernel 1620, so as to determine a predicted outcome 1625. In some instances, treatment target 1615a, 1615b is present as a wavefront representation when the healing kernel 1520 is applied. Exemplary techniques for converting topographic information to wavefront representations or for combining wavefront and topographic information are discussed elsewhere herein. Aspects of exemplary healing kernel techniques, which may also be referred to as filters, are described in previously incorporated U.S. Patent Application Nos. 61/708,815 and 61/734,030 filed Oct. 2, 2012 and Dec. 6, 2012, respectively. In this way, it is possible to obtain a predicted post-healing outcome 1625, where the predicted post-healing outcome 1625 is based on the treatment target ablation shape (e.g. 1615a or 1615b) and a healing kernel 1620. Based on a comparison between a single treatment version as depicted in FIG. 15 and a multiple treatment target version as depicted in FIG. 16, it can be seen that it is possible to use multiple patient/data sets to generate statistics that cannot be obtained when only one patient/data set is available. Exemplary methods also include comparing the predicted outcome 1625 and the actual outcome 1630 as shown in step 1635, for example by using a least mean squares approach. Methods may also include generating an adjusted set of laser basis data as indicated by adjustment protocol 1640, where the adjusted set of laser basis data is based on the initial set of laser basis data 1610 and the comparison 1635 between the actual post-healing outcome and the predicted post-healing outcome. The adjusted set of laser basis data can be used in refractive ophthalmologic ablation surgery. For example, as shown here, a wavefront measurement 1650 for a patient can be obtained, and a treatment target 1655 for the patient can be determined based on the adjusted basis data 1645 and the wavefront measurement 1650. In some cases, pre-operative measurement 1650 can be based on a wavefront measurement of the patient, a topography measurement of the patient, or both. Exemplary techniques for converting topographic information to wavefront representations or for combining wavefront and topographic information are discussed elsewhere herein. The treatment target can then be delivered to the patient as shown in treatment step 1660. Hence, it is possible to provide treatment for a patient that is based on basis data corresponding to a population of previously treated individuals. Such approaches can remove or reduce bias in a treatment system, or alleviate or account for systematic deviations that may be present in the system. Fixed basis data treatments based on this approach can be used for a single patient or for a group of patients.

Figure 17:
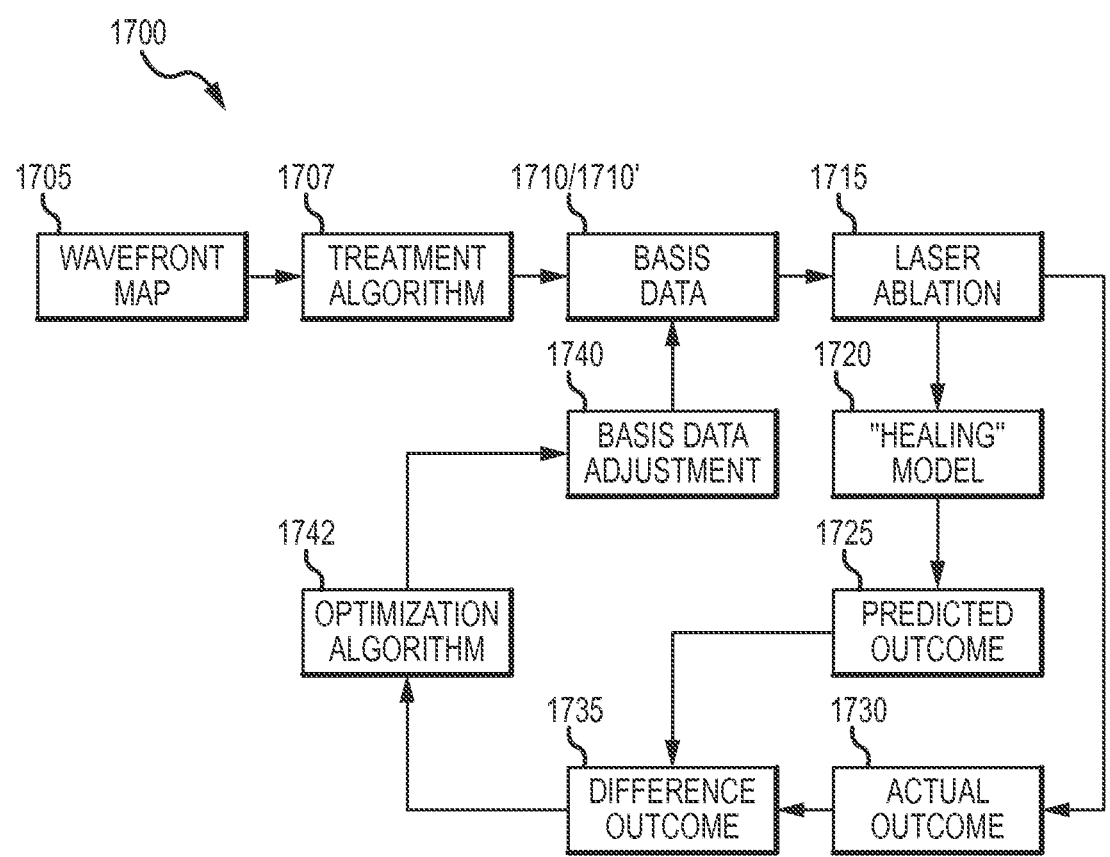
FIG. 17 depicts aspects of a basis data adjustment or development technique according to embodiments of the present invention.

FIG. 17 illustrates aspects of a laser basis data adjustment method 1700 according to embodiments of the present invention. As shown here, a treatment target or laser ablation 1715 for a patient can be determined based on a pre-operative wavefront measurement or map 1705 of the patient, optionally in combination with a treatment algorithm 1707, and an initial set of laser basis data 1710. An actual post-healing outcome 1730 of a patient treated with the laser ablation target 1715 can be acquired following the treatment. In this way, it is possible to obtaining an actual post-healing outcome 1730 of a patient treated with a treatment target ablation shape 1715, wherein the treatment target ablation shape is based on an initial set of laser basis data 1710 and a wavefront measurement 1705 obtained from the patient prior to treatment. In some cases, pre-operative measurement 1705 can be based on a wavefront measurement of the patient, a topography measurement of the patient, or both. Exemplary techniques for converting topographic information to wavefront representations or for combining wavefront and topographic information are discussed elsewhere herein. As shown here, embodiments of the present invention encompass techniques for processing the treatment target 1715 with a healing kernel or model 1720, so as to determine a predicted outcome 1725. In some instances, laser treatment target 1715 is present as a wavefront representation when the healing kernel 1720 is applied. Aspects of exemplary healing kernel techniques, which may also be referred to as filters, are described in previously incorporated U.S. Patent Application Nos. 61/708,815 and 61/734,030 filed Oct. 2, 2012 and Dec. 6, 2012, respectively. In this way, it is possible to obtain a predicted post-healing outcome 1725, where the predicted post-healing outcome 1725 is based on the treatment target ablation shape 1715 and a healing kernel 1720. Exemplary methods also include comparing the predicted outcome 1725 and the actual outcome 1730 as shown in step 1735, for example by using a least mean squares approach, so as to obtain a difference outcome 1735 representing the difference between the predicted and actual outcomes. Methods may also include generating an adjusted set of laser basis data 1710' using a basis data adjustment protocol 1740 and optimization algorithm 1742, where the adjusted set of laser basis data 1710' is based on the initial set of laser basis data 1710 and the comparison 1735 between the actual post-healing outcome and the predicted post-healing outcome. The adjusted set of laser basis data 1710' can be used in refractive ophthalmologic ablation surgery. For example, as depicted in FIGS. 15 and 16, a wavefront measurement for a patient can be obtained, and a treatment target for the patient can be determined based on the adjusted basis data and the wavefront measurement. The treatment target can then be delivered to the patient.

According to some embodiments, an exemplary method for generating laser basis data for use in refractive ophthalmologic ablation surgery can include obtaining an actual post-healing outcome of a patient treated with a treatment target ablation shape, where the treatment target ablation shape is based on an initial set of laser basis data and a wavefront measurement obtained from the patient prior to treatment. Further, the method may include obtaining a predicted post-healing outcome, where the predicted post-healing outcome is based on the treatment target ablation shape and a healing kernel. The method may also include comparing the actual post-healing outcome and the predicted post-healing outcome, and generating an adjusted set of laser basis data. The adjusted set of laser basis data can be based on the initial set of laser basis data and the comparison between the actual post-healing outcome and the predicted post-healing outcome.

Optical Coherence Tomography (OCT)

According to some embodiments, the development of basis data can be based on measurements of corneal depth which are performed in real time. In this way, it is possible to obtain an estimate or measure of the profile associated with each individual laser pulse. Further, when all laser pulses are delivered, additional developments can be implemented so as to refine the pulse profile of the basis data, with the use of instantaneous depth data recorded from the optical coherence tomography (OCT) system.

Figure 18:
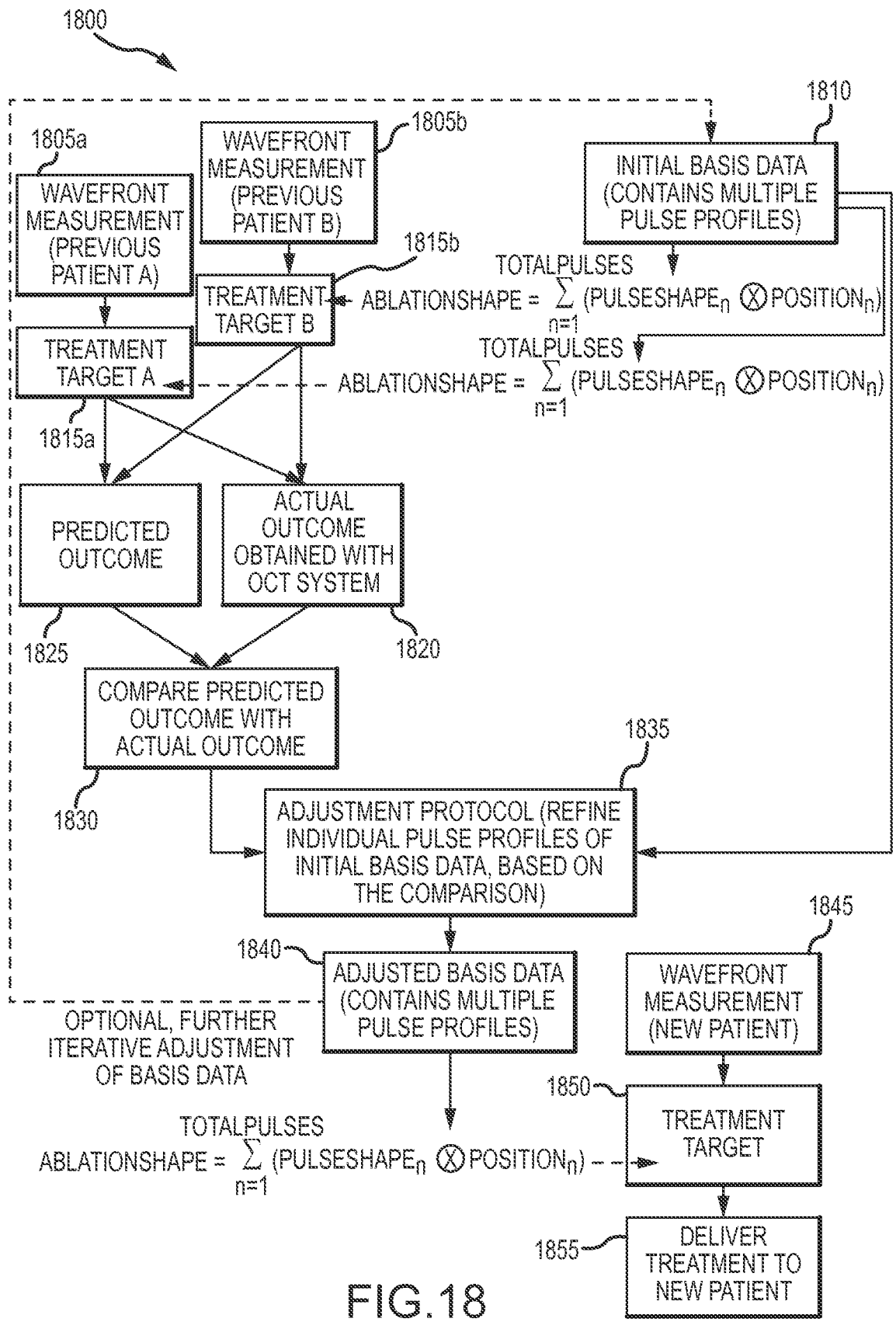
FIG. 18 depicts aspects of a basis data adjustment or development technique according to embodiments of the present invention.

FIG. 18 illustrates aspects of a laser basis data adjustment method 1800 according to embodiments of the present invention. As shown here, a treatment target 1815a for a patient A can be determined based on a pre-operative wavefront measurement 1805a of the patient A and an initial set of laser basis data 1810. Similarly, a treatment target 1815b for a patient B can be determined based on a pre-operative wavefront measurement 1805b of the patient B and the initial set of laser basis data 1810. In some cases, pre-operative measurement 1805a, 1805b can be based on a wavefront measurement of the patient, a topography measurement of the patient, or both. Exemplary techniques for converting topographic information to wavefront representations or for combining wavefront and topographic information are discussed elsewhere herein. For each of the treatment targets 1815a, 1815b, an actual surgical outcome 1820 of the patient treated with the target (e.g. patient A treated with target A, or patient B treated with target B) be acquired following the treatment. In this way, it is possible to obtaining an actual surgical outcome 1820 of a patient treated with a treatment target ablation shape, where the treatment target ablation shape is based on an initial set of laser basis data 1810 and a wavefront measurement obtained from the patient prior to treatment.

Similarly, it is possible to determine or generate a predicted surgery outcome 1825 for patient A or patient B, where the predicted surgery outcome 1825 is based on the treatment target (e.g. treatment target A or treatment target B, respectively). As shown here, the method can also include comparing the predicted surgery outcome 1825 with the actual surgery outcome 1820 for the individual (e.g. patient A or patient B), where the actual surgery outcome 1820 is based on an optical coherence tomography analysis of an eye of the individual (e.g. patient A or patient B) treated with the treatment target (e.g. target A or target B). Typically, the predicted outcome 1825 is present in a wavefront representation when comparing to the actual outcome 1820.

As depicted in FIG. 18, methods may also include determining, for example via a processing module having a tangible medium embodying machine-readable code, a treatment or adjusted basis data 1840 for use in a laser ablation vision procedure. In some cases, the adjusted basis data 1840 can be determined by implementing an adjustment protocol 1835. The treatment basis data 1840 can be based on the initial basis data 1810 and the comparison 1830 between the predicted surgery outcome 1825 and the actual surgery outcome 1820 for the individual. The treatment basis data 1840 can include a set of pulse profiles that differs from the set of pulse profiles of the initial basis data 1810. In some cases, methods can include determining a patient treatment target 1850 for the patient, where the patient treatment target 1850 is based on the treatment basis data 1840 and a wavefront measurement 1845 for the patient. In some cases, pre-operative measurement 1845 can be based on a wavefront measurement of the patient, a topography measurement of the patient, or both. Exemplary techniques for converting topographic information to wavefront representations or for combining wavefront and topographic information are discussed elsewhere herein. In some cases, methods include delivering the patient treatment target 1850 to the patient, as indicated in step 1855. In some cases, the step 1830 of comparing the predicted surgery outcome 1825 with the actual surgery outcome 1820 is based on a least mean squares comparison. Throughout the instant application, the terms least squares fitting (LSF) and least means squares (LMS) can be used interchangeably.

According to some embodiments, methods can include inputting multiple treatment targets for respective individuals. For example, methods may include inputting a second treatment target 1815b for a second individual, where the second treatment target 1815b is based on a wavefront measurement 1805b for the second individual and the initial basis data 1810. Relatedly, methods may include generating a predicted surgery outcome for the second individual, where the predicted surgery outcome based on the second treatment target. Further, methods may include comparing the predicted surgery outcome with an actual surgery outcome for the second individual, where the actual surgery outcome is based on an optical coherence tomography analysis of an eye of the second individual treated with the second treatment target. What is more, methods may include determining, for example via a processing module comprising a tangible medium embodying machine-readable code, the treatment basis data for use in the laser ablation vision procedure. The treatment basis data can be based on the initial basis data and the comparison between the predicted surgery outcome and the actual surgery outcome for the second individual.

Figure 18A:
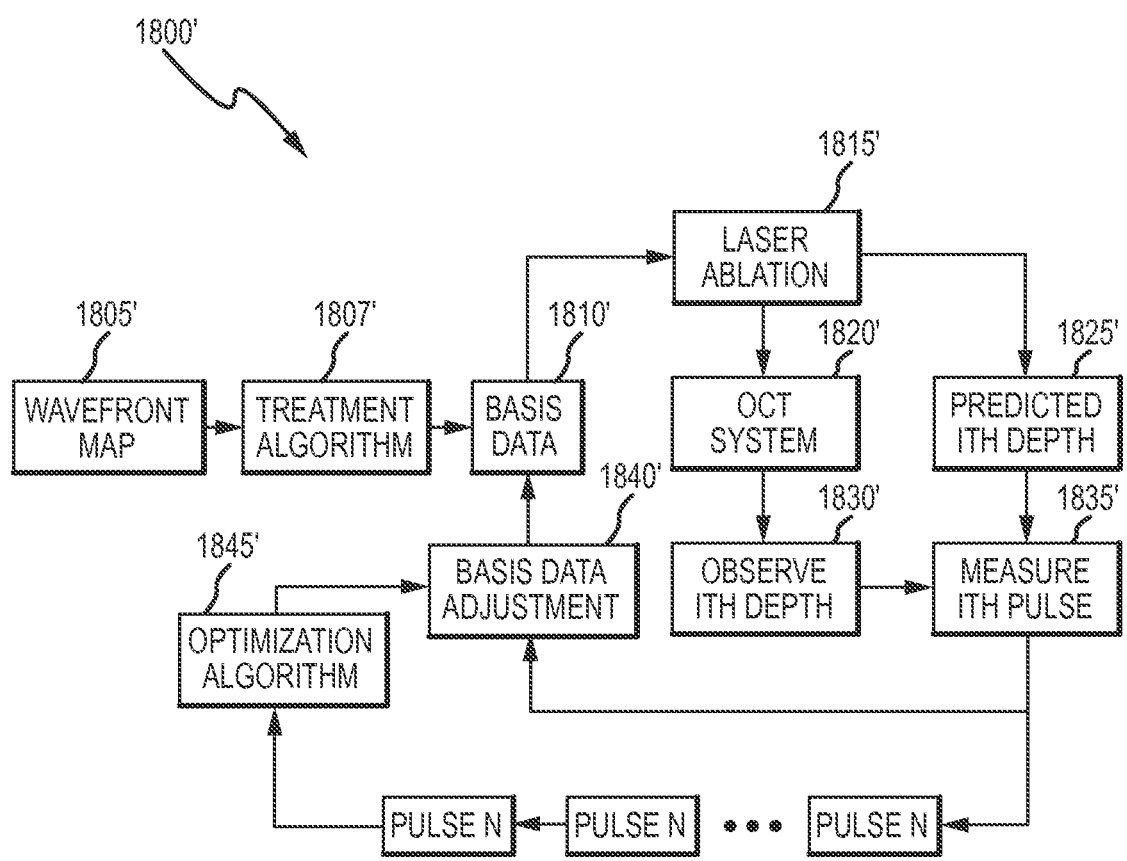
FIG. 18A depicts aspects of a basis data adjustment or development technique according to embodiments of the present invention.

FIG. 18A illustrates aspects of a laser basis data adjustment method 1800' according to embodiments of the present invention. As shown here, a treatment target or laser ablation 1815' for a patient can be determined based on a pre-operative wavefront measurement or map 1805' of the patient, optionally in combination with a treatment algorithm 1807', and an initial set of laser basis data 1810'. The basis data can include a set of pulse profiles. In some cases, the laser ablation or treatment target 1815' can be based on a wavefront measurement for a patient and a basis data, such as an initial basis data. In some cases, pre-operative measurement 1805' can be based on a wavefront measurement of the patient, a topography measurement of the patient, or both. Exemplary techniques for converting topographic information to wavefront representations or for combining wavefront and topographic information are discussed elsewhere herein. An actual or observed outcome 1830' of a patient treated with the laser ablation target 1815' can be acquired during or following the treatment. For example, it is possible to obtain or observe an $i^{th}$ depth outcome 1830' (e.g associated with an $i^{th}$ pulse) using an OCT system 1820'. Similarly, a predicted outcome 1825' can be determined based on the laser ablation target 1815'. For example, the predicted outcome can be a predicted $i^{th}$ depth 1825' (e.g associated with an $i^{th}$ pulse). As shown here, the method can also include measuring the $i^h$ pulse, as indicated in step 1835'. In some instances, step 1835' involves comparing the observed depth or profile 1830' of the pulse (or a set of pulses) with the predicted depth or profile 1825' of the pulse (or set of pulses). Based on the comparison, it is possible to implement a basis data adjustment operation 1840', so as to obtain an adjusted basis data. In some cases, it is possible to determine the adjusted basis data, for example via a processing module having a tangible medium embodying machine-readable code, where the adjusted basis data is based on the initial basis data and the comparison between the predicted surgery outcome and the actual surgery outcome for the patient. Often, the adjusted basis data includes a set of pulse profiles that differs from the set of pulse profiles of the initial basis data. In some cases, it is possible to implement an optimization algorithm 1845', so as to obtain a more accurate set of basis data. For example, in some cases, the basis data can be characterized by three parameters: the width, the depth, and the height of the central island. Setting these parameters as free parameters, a multi-dimensional optimization algorithm, such as a simulated annealing, a downhill simplex, or a simple least mean square, can be used to obtain the values of these free parameters yielding a smallest error. This optimization can be applied to a single treatment. This optimization can also be applied to multiple treatments for an improved outcome. According to some embodiments, the application to multiple treatments would not be in a closed-loop situation, but in a post-processing step, i.e., optimization with prior data set to obtain an improved basis data set to treat new patients.

Figure 18B:
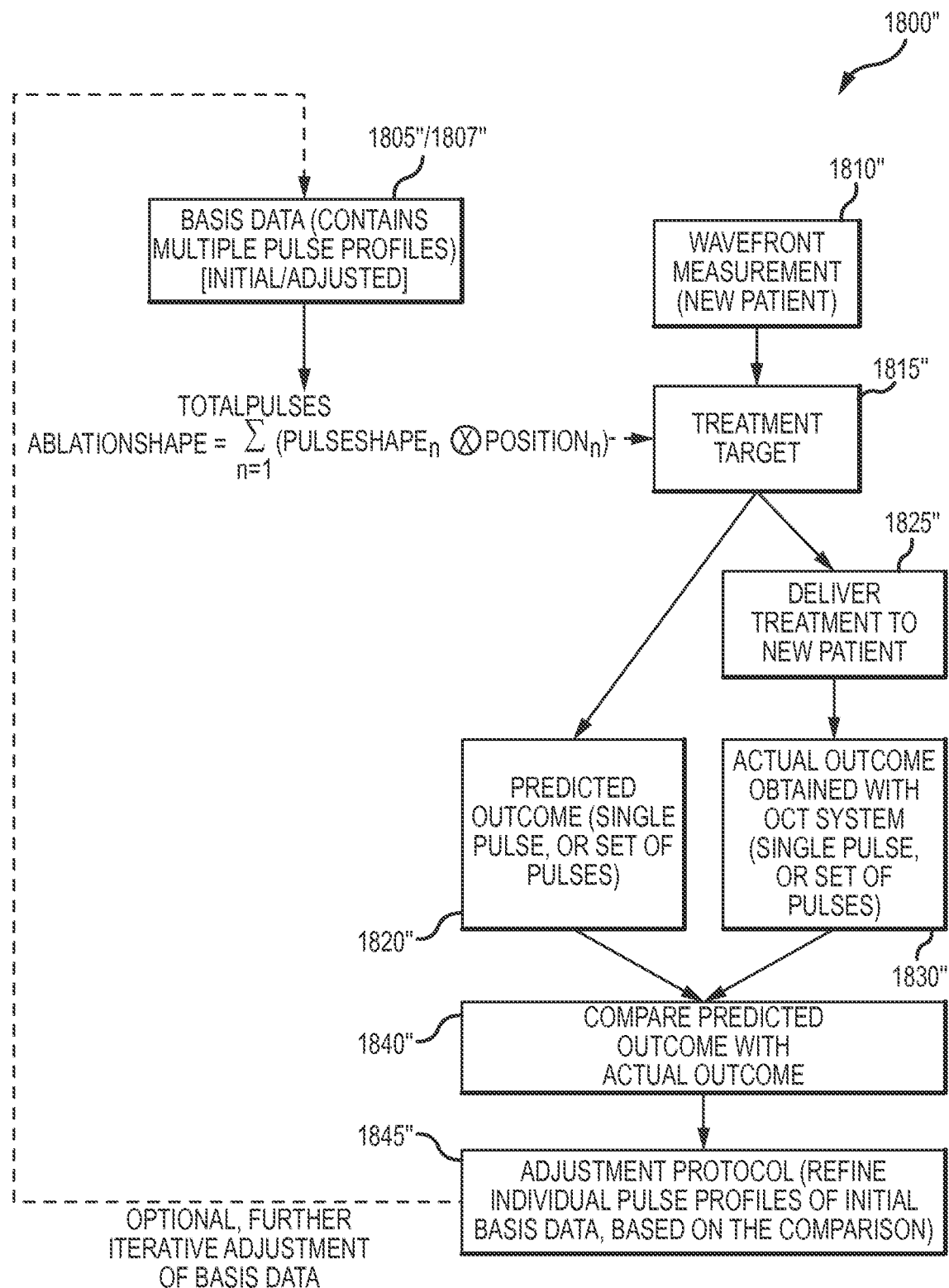
FIG. 18B depicts aspects of a basis data adjustment or development technique according to embodiments of the present invention.

FIG. 18B depicts aspects of a method 1800" of determining an adjusted basis data for use in a laser ablation vision procedure for a patient, according to embodiments of the present invention. As shown here, the method may include inputting an initial basis data 1805", where the initial basis data includes a set of pulse profiles. The method can also include inputting a treatment target 1815" for the patient. The treatment target 1815" can be based on a wavefront measurement 1810" for the patient and the initial basis data 1805". In some cases, pre-operative measurement 1810" can be based on a wavefront measurement of the patient, a topography measurement of the patient, or both. Exemplary techniques for converting topographic information to wavefront representations or for combining wavefront and topographic information are discussed elsewhere herein. Methods can also include generating a predicted surgery outcome 1820" for the patient. The predicted surgery outcome 1820" can be based on the treatment target 1815". In some cases, the predicted outcome 1820" corresponds to a single ablation pulse. In some cases, the predicted outcome 1820" corresponds to a set of ablation pulses. Methods can also include comparing the predicted surgery outcome 1820" with an actual surgery outcome 1830" for the patient. Typically, the predicted outcome 1820" is present in a wavefront representation when comparing to the actual outcome 1830". The actual surgery outcome 1830" can be based on an optical coherence tomography analysis of an eye of the patient, where the eye has been treated with the treatment target 1815" as part of a laser ablation vision procedure as depicted in step 1825". In some cases, the actual outcome 1830" corresponds to a single ablation pulse. In some cases, the actual outcome 1320" corresponds to a set of ablation pulses. As depicted here, methods can also include comparing the predicted outcome 1820" with the actual outcome 1830" as indicated by step 1840". According to some embodiments, the comparison can be made on a real-time or instantaneous basis. For example, it is possible to compare a measured pulse effect with a predicted pulse effect during the course of delivery of an ablation treatment. In some cases, the comparison can be made between the measured effect of a set of pulses and the predicted effect of a set of pulses. In some instances, if the difference between the measured effect and the predicted effect exceeds a certain threshold or is outside of a certain tolerance or allowable fluctuation (e.g. based on a statistically significant deviation), it is possible to implement a basis data adjustment protocol as discussed elsewhere herein. Such instantaneous or real-time measurements and adjustments can be performed during the course of an ablation treatment, so as to provide a customized treatment for the patient. In this sense, the basis data can be adjusted for the particular patient thus providing an individualized treatment. Accordingly, the treatment can accommodate unique variations presented by the patient as compared to a population or average of individuals. In some cases, such customization or basis data adjustment can be performed on an eye-by-eye basis. That is, one eye of a patient can be treated according to a first basis data adjustment protocol specific for that eye and the other eye of a patient can be treated according to a second basis data adjustment protocol specific for that eye.

In some cases, it is possible to implement an adjustment protocol 1845", so as to obtain an adjusted basis data. In some instances, adjustment protocols can include refining one or more individual pulse profiles or an initial or existing basis data, based on the comparison 1840" between the predicted and actual outcomes. For example, methods may include determining, via a processing module comprising a tangible medium embodying machine-readable code, an adjusted basis data 1807", wherein the adjusted basis data 1807" is based on the initial basis data 1805" and the comparison 1840" between the predicted surgery outcome and the actual surgery outcome for the patient. In some cases, the adjusted basis data 1807" includes a set of pulse profiles that differs from the set of pulse profiles of the initial basis data 1805". In some cases, methods can include determining an adjusted patient treatment target for the patient, where the adjusted patient treatment target is based on the adjusted basis data 1807" and the wavefront measurement 1810" for the patient. In some cases, methods include delivering the adjusted patient treatment target to the patient. In some cases, the step 1840" of comparing the predicted surgery outcome with the actual surgery outcome for the patient is based on a least mean squares comparison.

Adjusted Basis Data Profiles

Figure 19A:
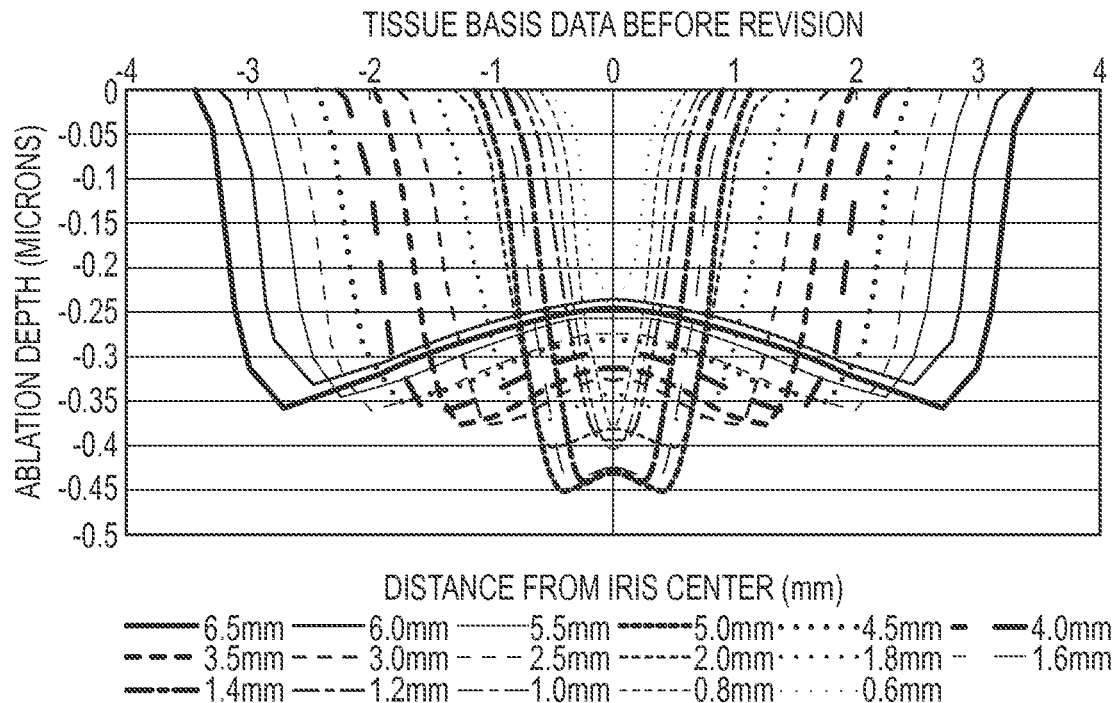
FIGS. 19A and 19B depicts aspects of pre-revision and post-revision basis data according to embodiments of the present invention.
Figure 19B:
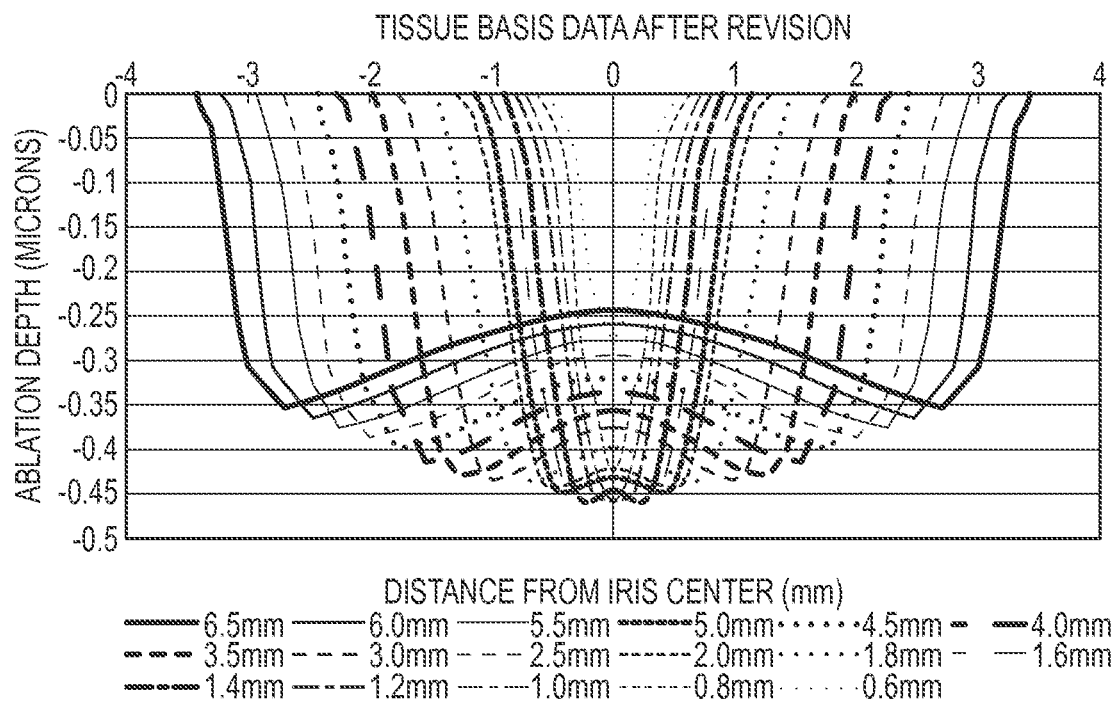
Figure 20A:
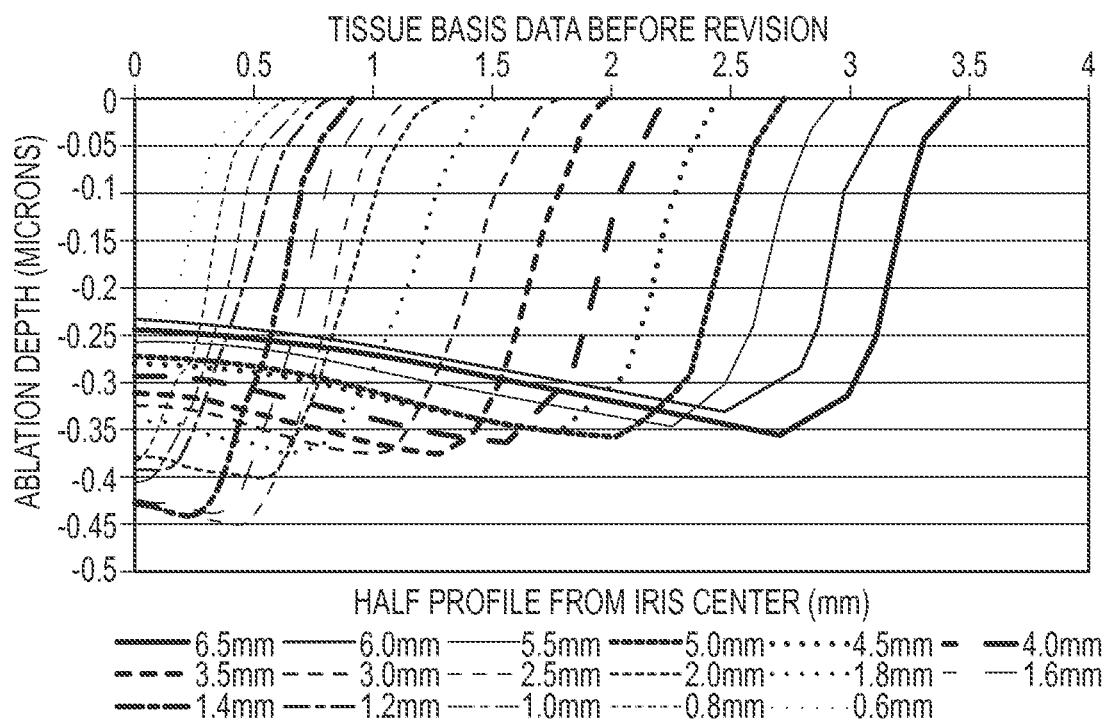
FIGS. 20A and 20B depicts aspects of pre-revision and post-revision basis data according to embodiments of the present invention.
Figure 20B:
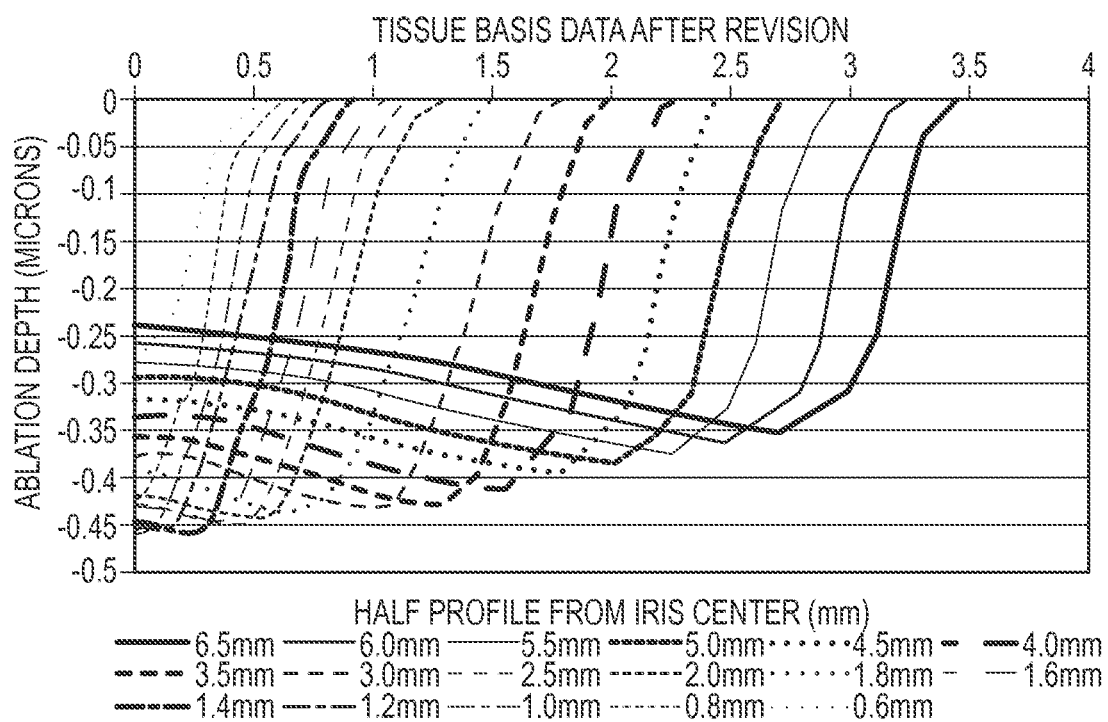

FIG. 19A depicts tissue basis data profiles before the implementation of an adjustment or revision process, and FIG. 19B depicts tissue basis data profiles following the implementation of an adjustment or revision process. FIGS. 20A and 20B depicts portions of the profiles shown in FIGS. 19A and 19B, respectively. As illustrated in these figures, the original basis data, for example as shown in FIG. 19A, exhibits somewhat random depth and width of each diameter. The randomness of the depth and width of the original set of basis data, which can correspond to data directly obtained from measurements of ablation profiles of porcine and human eyes, exhibits measurement errors, among other errors. In contrast, the revised basis data, as shown in FIG. 19B, shows a smooth transition for all diameters in terms of depth, width, and central island.

According to some embodiments, a scaling operation can be applied to the revised basis data. In some cases, the revision of the basis data to achieve improved smoothness in terms of width and depth may not guarantee the accurate representation as a whole for the actual ablation. In some cases, use of a set of basis data to achieve an actual clinical outcome can be supplemented by applying a uniform scaling factor such that the clinical outcome meets the expectation. For example, if an overcorrection is found, a scaling factor smaller than 1 can be applied. If an undercorrection is found, a scaling factor larger than 1 can be applied.

Figure 21:
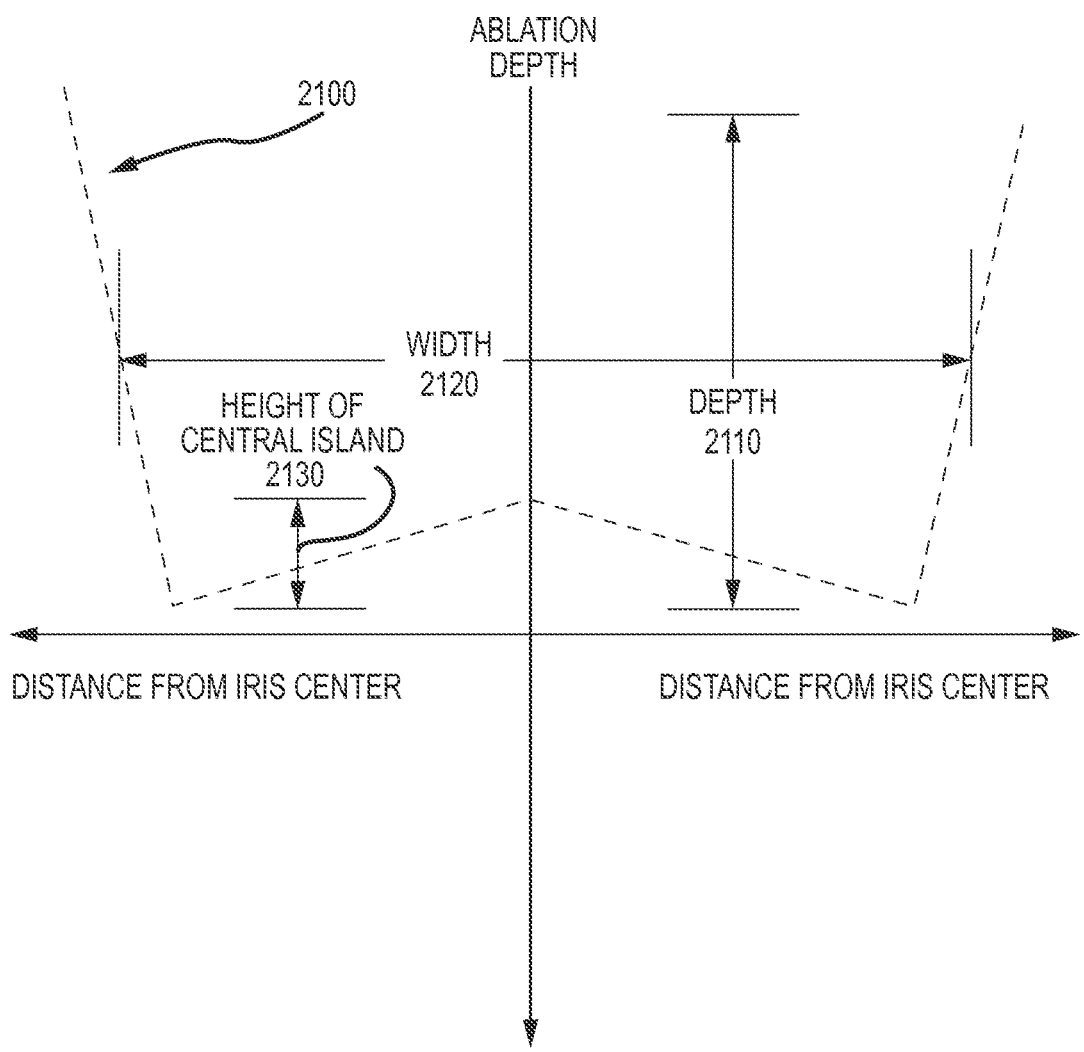
FIG. 21 depicts aspects of basis data parameters according to embodiments of the present invention.

As noted elsewhere herein, basis data can be characterized by various parameters, such as width, depth, and height of the central island. FIG. 21 depicts an exemplary basis data profile 2100 according to embodiments of the present invention. As shown here, the profile 2100 has a depth 2110, a width 2120, and a central island height 2130. In some instances, the width 2120 can be mechanically influenced. For example, the width 2120 can be determined based on an aperture width or diameter of a pulse delivery device. In some cases, the maximum pulse profile width can correspond to an energy distribution associated with the pulse, and the profile width 2120 can be associated with an aperture width or diameter that is less than the maximum energy width. In some instances, the depth 2110 and height of the central island 2130 can be determined based on an energy distribution associated with a pulse.

The methods and apparatuses of the present invention may be provided in one or more kits for such use. The kits may comprise a system for profiling an optical surface, such as an optical surface of an eye, and instructions for use. Optionally, such kits may further include any of the other system components described in relation to the present invention and any other materials or items relevant to the present invention. The instructions for use can set forth any of the methods as described above.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

All patents, patent publications, patent applications, journal articles, books, technical references, and the like discussed in the instant disclosure are incorporated herein by reference in their entirety for all purposes.

While the above provides a full and complete disclosure of the preferred embodiments of the present invention, various modifications, alternate constructions and equivalents may be employed as desired. Therefore, the above description and illustrations should not be construed as limiting the invention, which can be defined by the appended claims.

What is claimed is:

1. A method of determining an adjusted basis data that improves an accuracy of a laser ablation vision procedure performed on a patient, the method comprising:
    inputting an initial basis data, the initial basis data comprising a set of pulse profiles;
    determining a first treatment target ablation profile based on the initial basis data and measurements of a previous patient acquired by one or more sensors;
    deconvolving the first treatment target ablation profile with a low pass filter to generate a first predicted surgery outcome;
    determining an actual surgery outcome for the previous patient after an eye of the previous patient has healed, wherein the previous patient has previously received the laser ablation vision procedure based on the initial basis data;
    comparing the first predicted surgery outcome with the actual surgery outcome based on a least mean squares comparison of an optical path difference (OPD) to generate a comparison result;
    updating the initial basis data based on the comparison result to form adjusted basis data, wherein the adjusted basis data comprises a second set of pulse profiles that differs from the set of pulse profiles from the initial basis data; and
    controlling a laser ablation system to deliver the laser ablation vision procedure to the patient based on the adjusted basis data.

2. The method according to claim 1, further comprising:
    determining a post-surgery outcome for the patient after the eye of the patient has healed; and
    storing the post-surgery outcome as a second actual surgery outcome that is used in a subsequent laser ablation vision procedure.

3. The method according to claim 1, wherein the adjusted basis data comprises multiple pulses of different shapes.

4. A system for determining an adjusted basis data that improves an accuracy of a laser ablation vision procedure performed on a patient, the system comprising:
    a memory that stores an initial basis data for a plurality of patients, the initial basis data comprising a set of pulse profiles;
    an input that receives measurements of a previous patient from one or more sensors, wherein the measurements includes at least one of a wavefront measurement and a topography measurement;
    a processor communicatively coupled to memory and the input, wherein the processor:
        retrieves, from the memory, the initial basis data for the previous patient,
        determines a first treatment target ablation profile based on the measurements from the one or more sensors and the initial basis data,
        deconvolves the first treatment target ablation profile with a low pass filter to generate a first predicted surgery outcome,
        determines, using the memory, an actual surgery outcome for the previous patient after an eye of the previous patient has healed, wherein the previous patient has received the laser ablation vision procedure based on the initial basis data;
        compares the first predicted surgery outcome with the actual surgery outcome based on a least mean squares comparison optical path difference (OPD) to generate a comparison result;
        updates the initial basis data based on the comparison result to form adjusted basis data, wherein the adjusted basis data comprises a second set of pulse profiles that differs from the set of pulse profiles of the initial basis data; and
        controls a laser ablation system to deliver the laser ablation vision procedure to the patient based on the adjusted basis data.

5. The system according to claim 4, wherein the processor further:
    determines a post-surgery outcome for the patient after the eye of the patient has healed; and
    stores, in the memory, the post-surgery outcome as a second actual surgery outcome that is used in a subsequent laser ablation vision procedure.

* * * * *